United States Patent
Welch et al.

(10) Patent No.: US 7,453,076 B2
(45) Date of Patent: Nov. 18, 2008

(54) BI-POLAR TREATMENT FACILITY FOR TREATING TARGET CELLS WITH BOTH POSITIVE AND NEGATIVE IONS

(75) Inventors: Larry Welch, Santa Barbara, CA (US); Ray Winn, Las Vegas, NV (US)

(73) Assignee: Nanolife Sciences, Inc., Santa Barbara, CA (US)

( * ) Notice: Subject to any disclaimer, the term of this patent is extended or adjusted under 35 U.S.C. 154(b) by 18 days.

(21) Appl. No.: 11/690,565

(22) Filed: Mar. 23, 2007

(65) Prior Publication Data

US 2008/0234531 A1    Sep. 25, 2008

(51) Int. Cl.
*A61N 5/00* (2006.01)
*G21G 5/00* (2006.01)

(52) U.S. Cl. ............... 250/492.3; 250/396 R; 250/310; 250/396 ML; 250/398; 250/397; 250/492.1; 250/394; 250/493.1; 315/501; 315/502; 315/5.41; 378/65; 378/137; 31/62; 600/1; 600/427

(58) Field of Classification Search ............. 250/396 R, 250/310, 396 ML, 398, 397, 492.3, 492.1, 250/394, 493.1; 315/501, 502, 5.41; 378/65, 378/137; 376/127, 156; 313/62; 600/1, 600/427
See application file for complete search history.

(56) References Cited

U.S. PATENT DOCUMENTS

| | | | | |
|---|---|---|---|---|
| 5,017,789 A | * | 5/1991 | Young et al. | 250/396 ML |
| 5,339,812 A | | 8/1994 | Hardy et al. | |
| 5,895,926 A | * | 4/1999 | Britton et al. | 250/492.3 |
| 5,977,554 A | * | 11/1999 | Smith et al. | 250/493.1 |
| 2004/0162457 A1 | * | 8/2004 | Maggiore et al. | 600/1 |

* cited by examiner

*Primary Examiner*—Jack I. Berman
*Assistant Examiner*—Meenakshi S Sahu
(74) *Attorney, Agent, or Firm*—Baker & McKenzie LLP

(57) ABSTRACT

A system for treating target cells with both positive and negative ions comprises a bi-polar beam delivery system configured to create and deliver both positive ion beams and negative ion beams. The bi-polar beam delivery system comprises a bi-polar accelerator configured to accelerate positive and negative ions in the same direction making such a bi-polar beam delivery system practical.

32 Claims, 29 Drawing Sheets

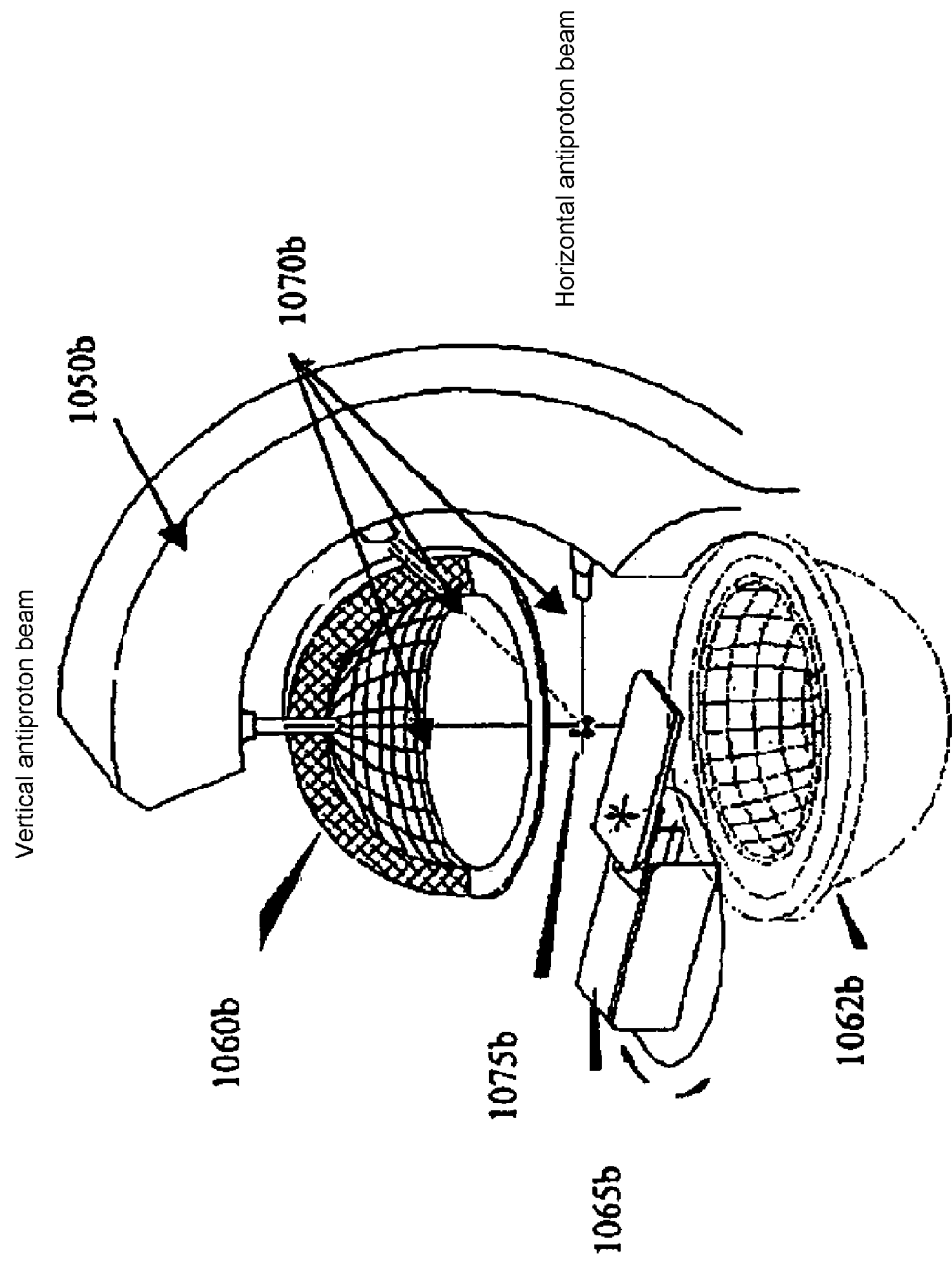

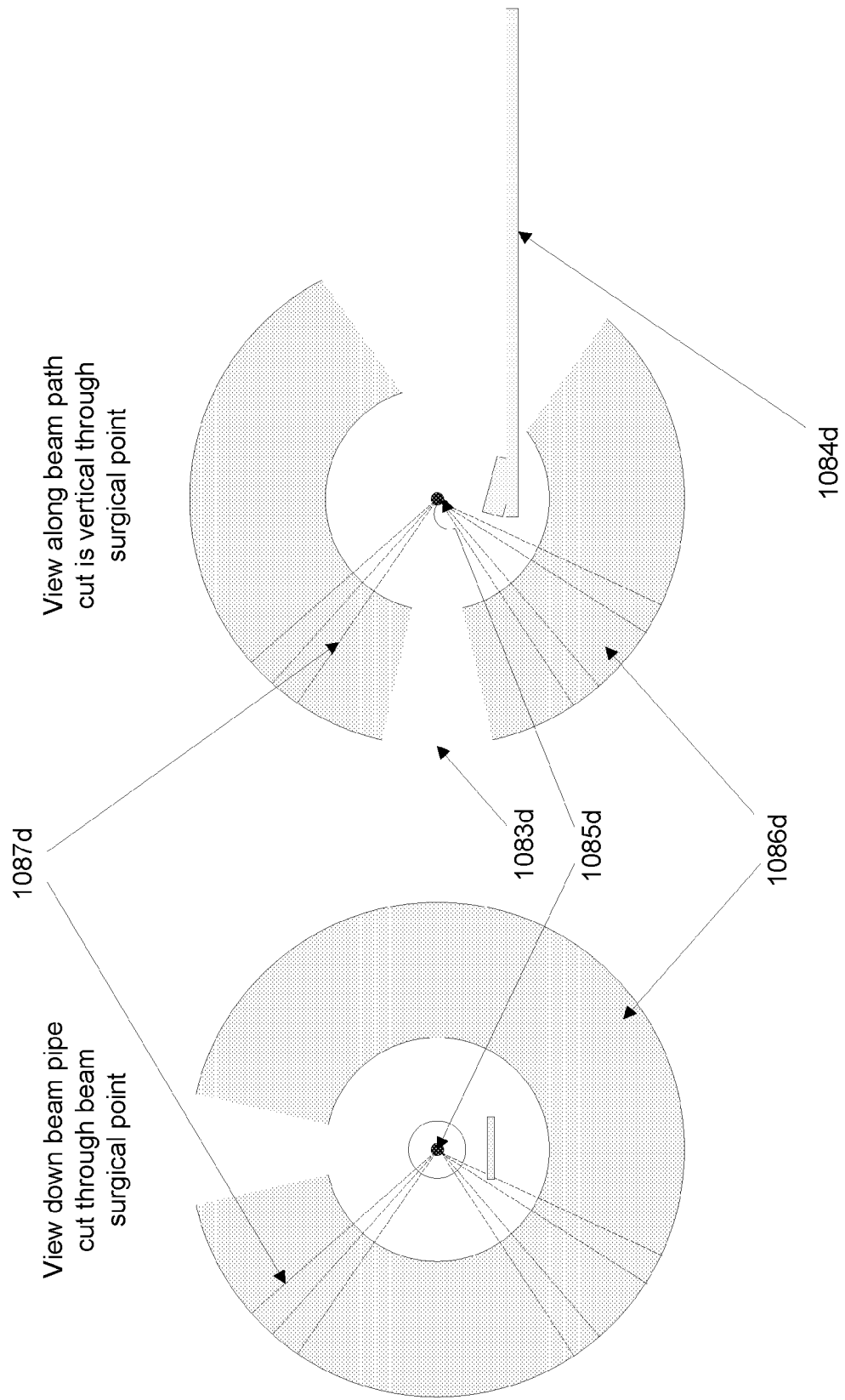

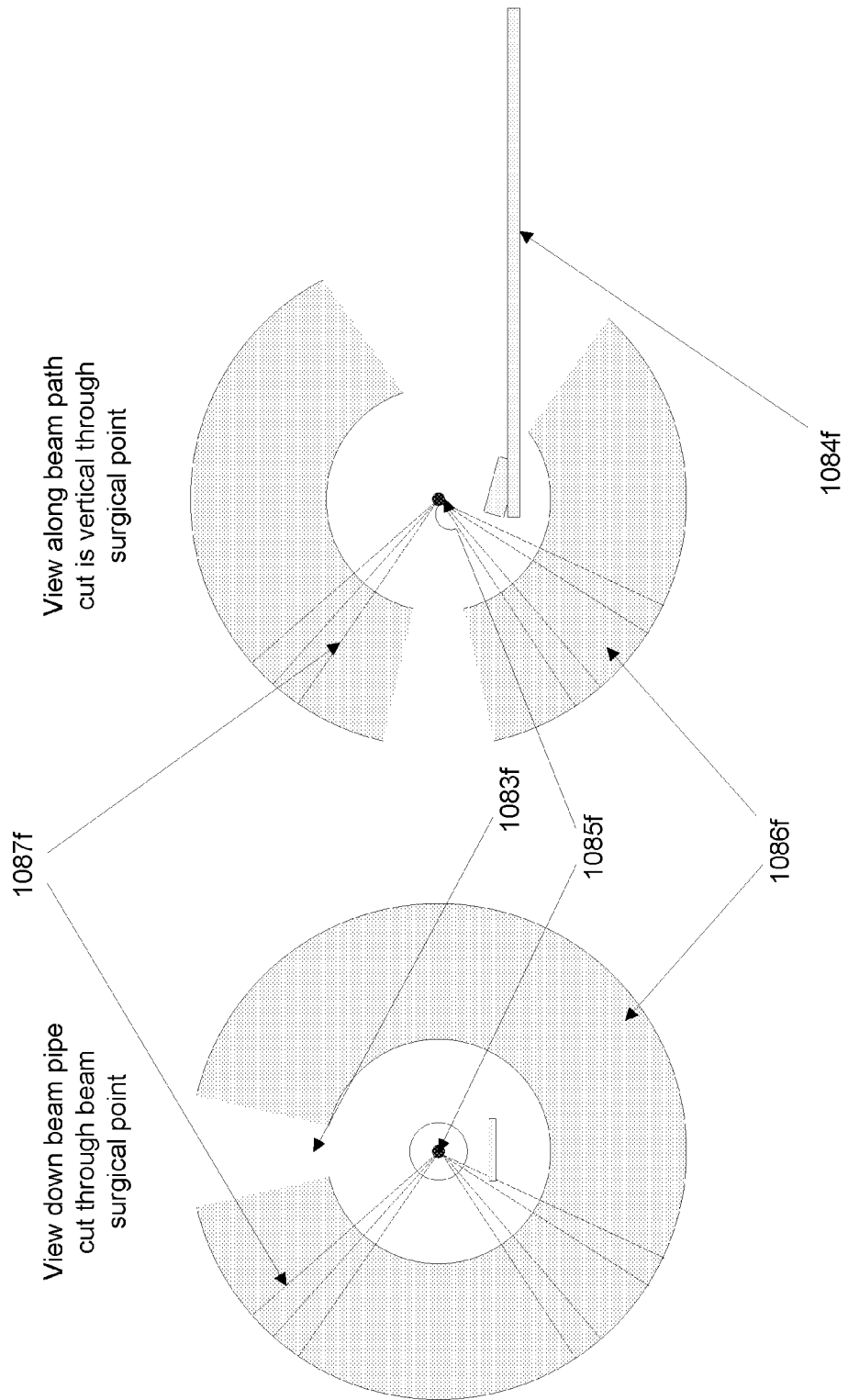

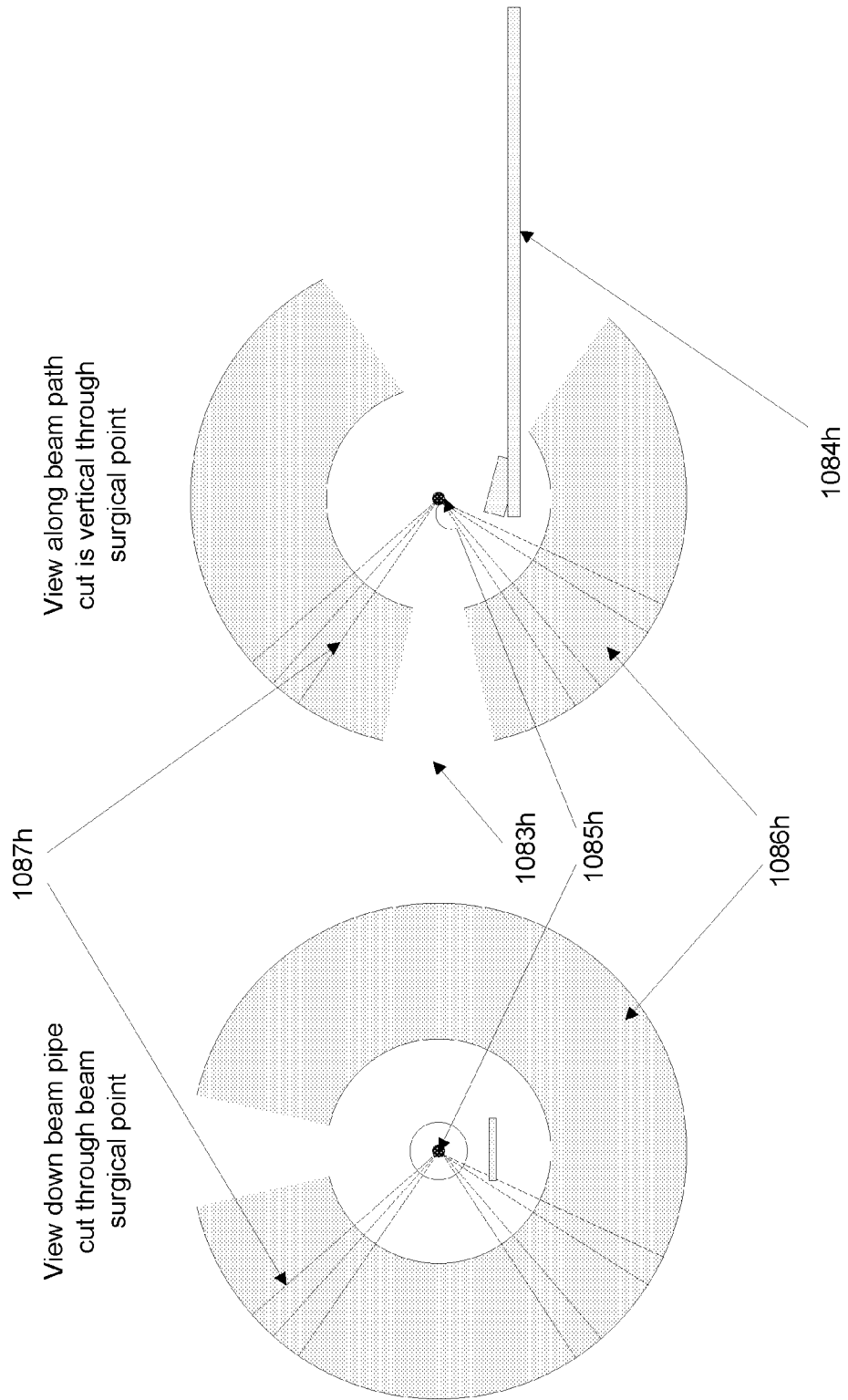

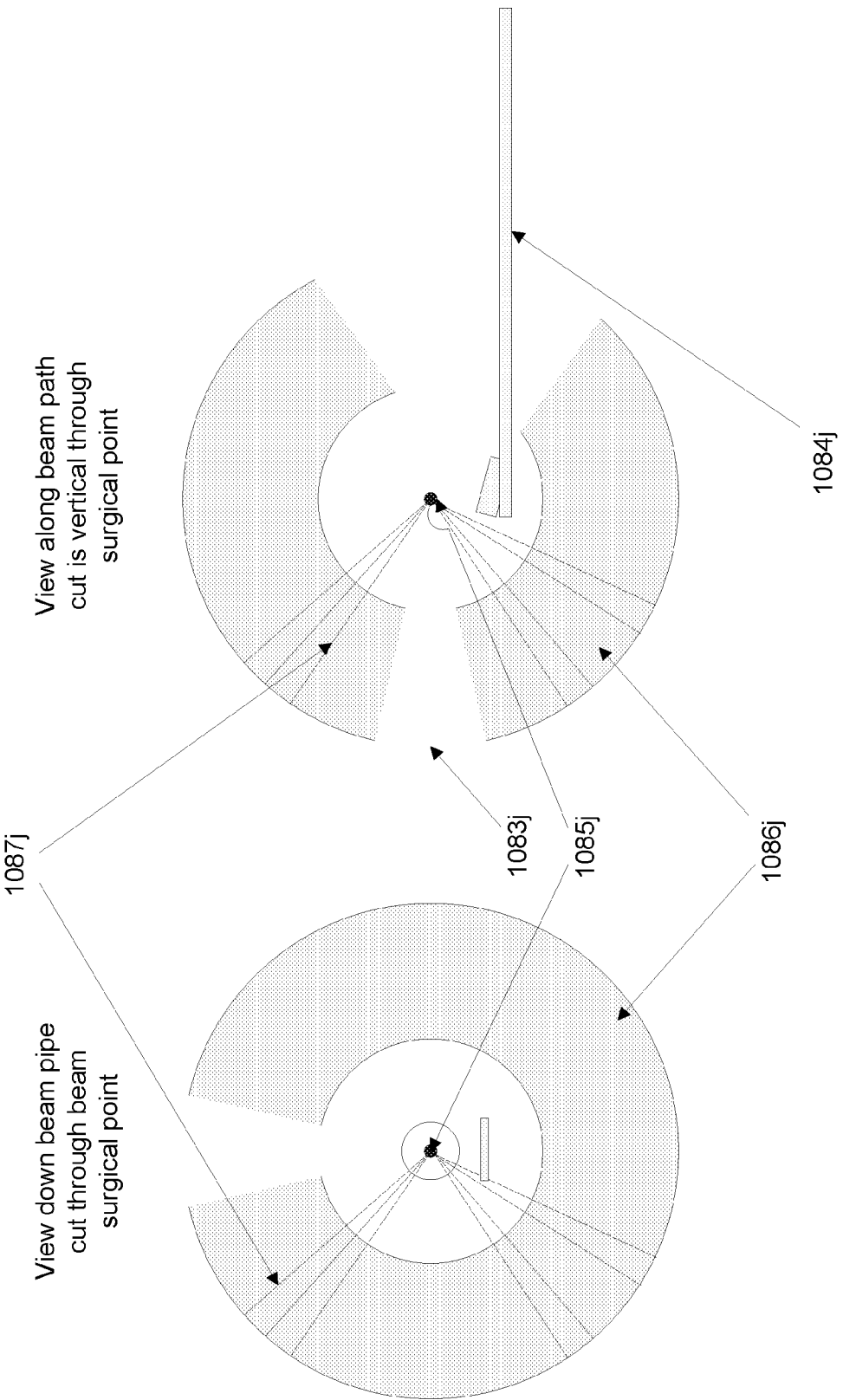

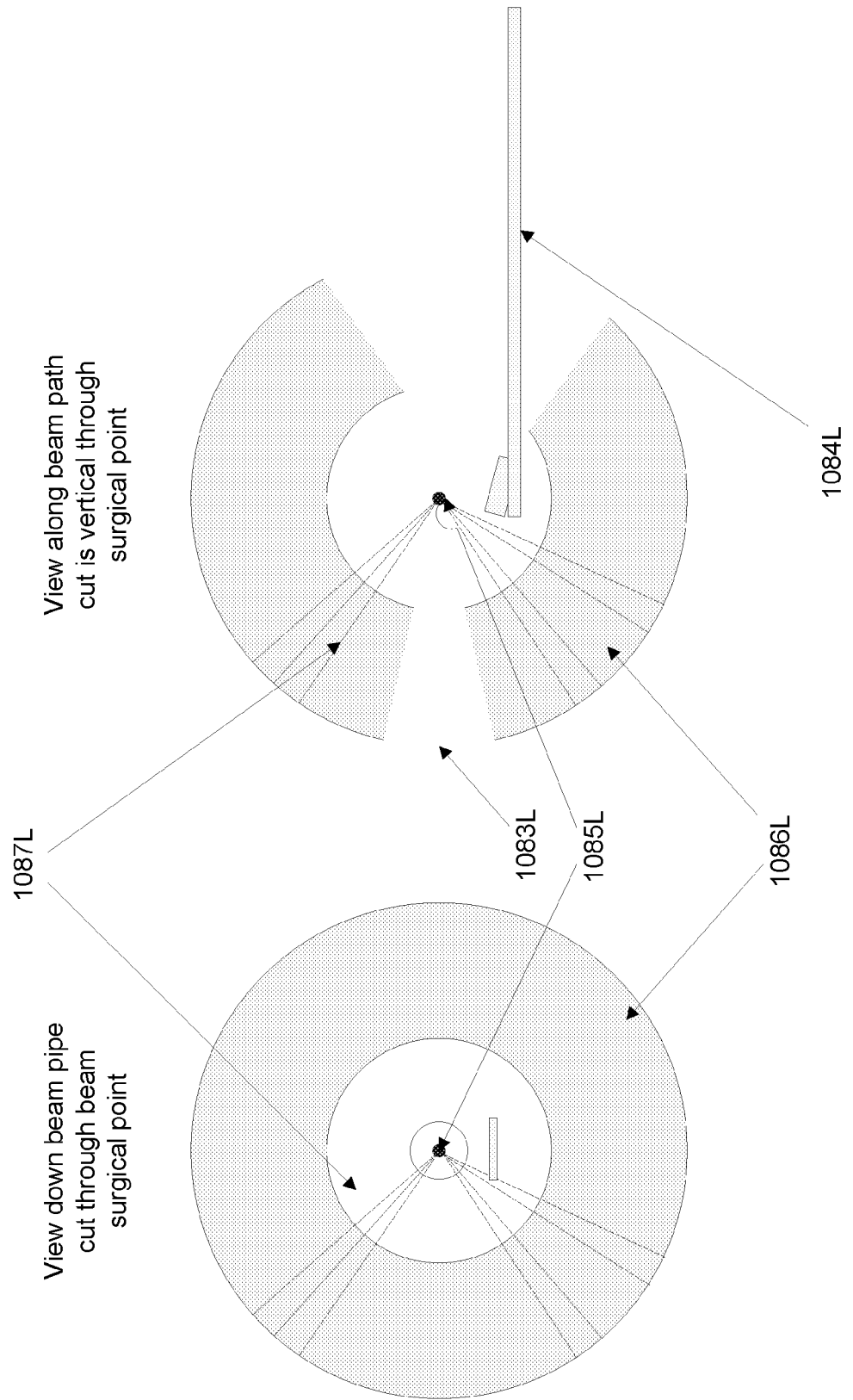

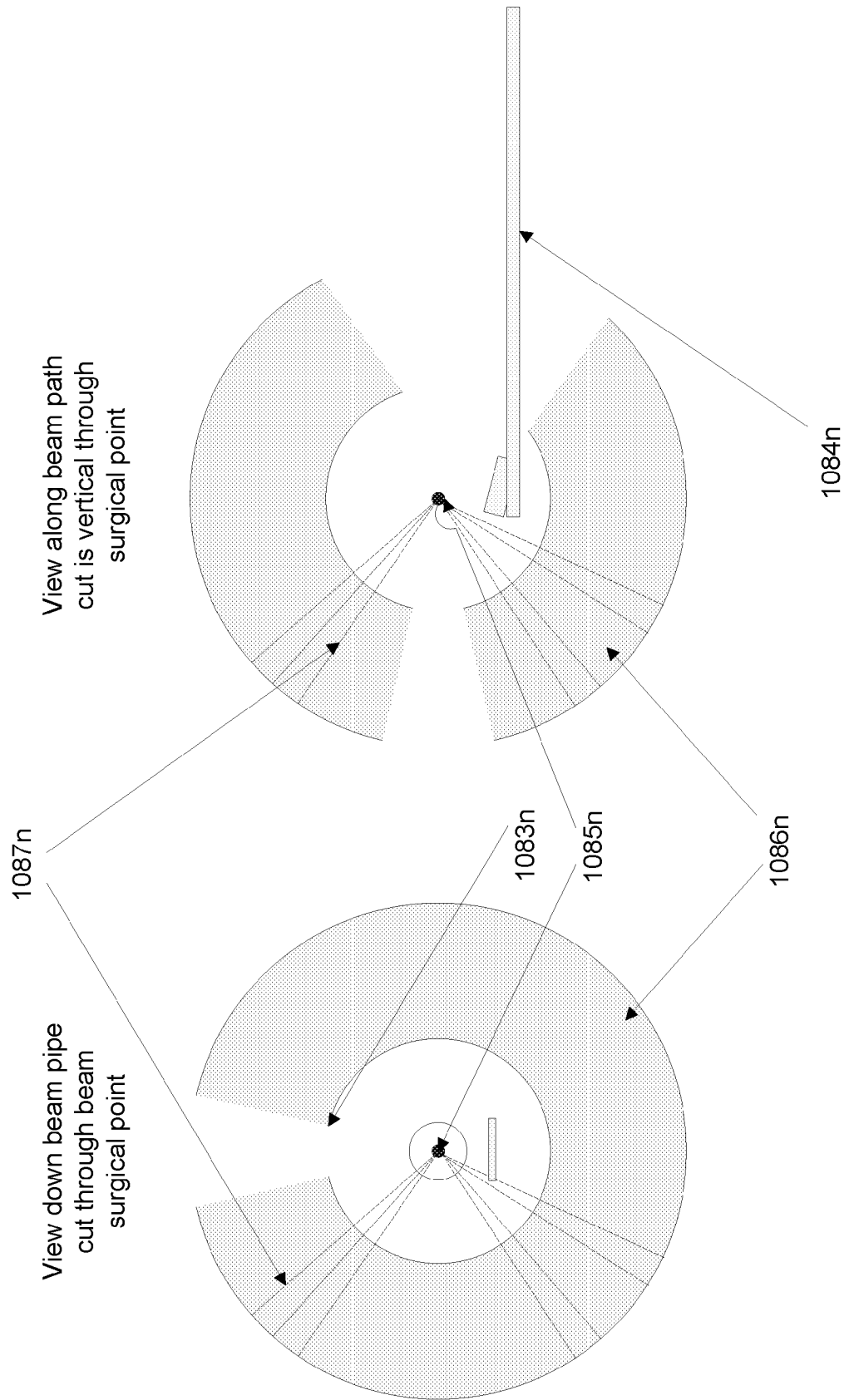

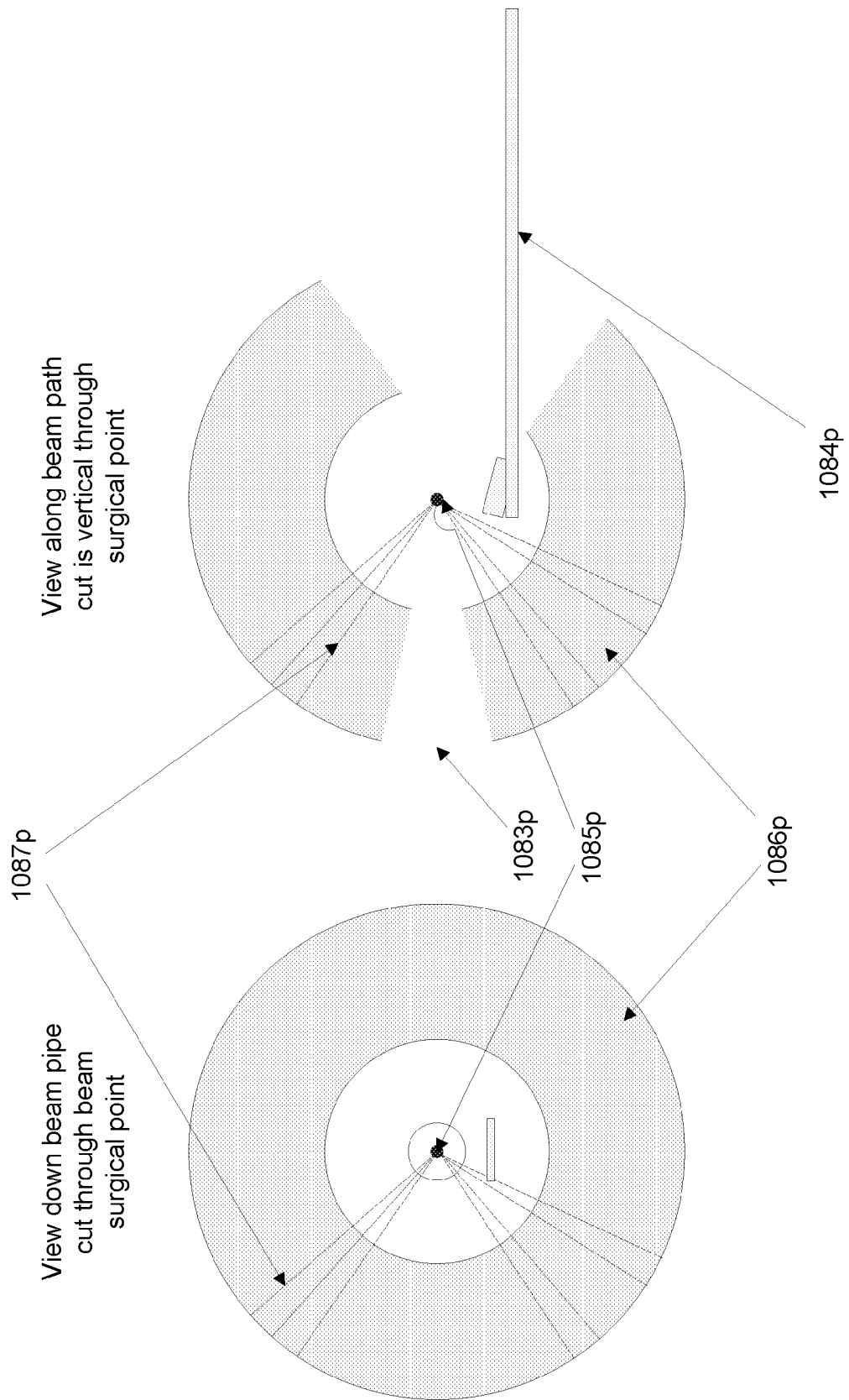

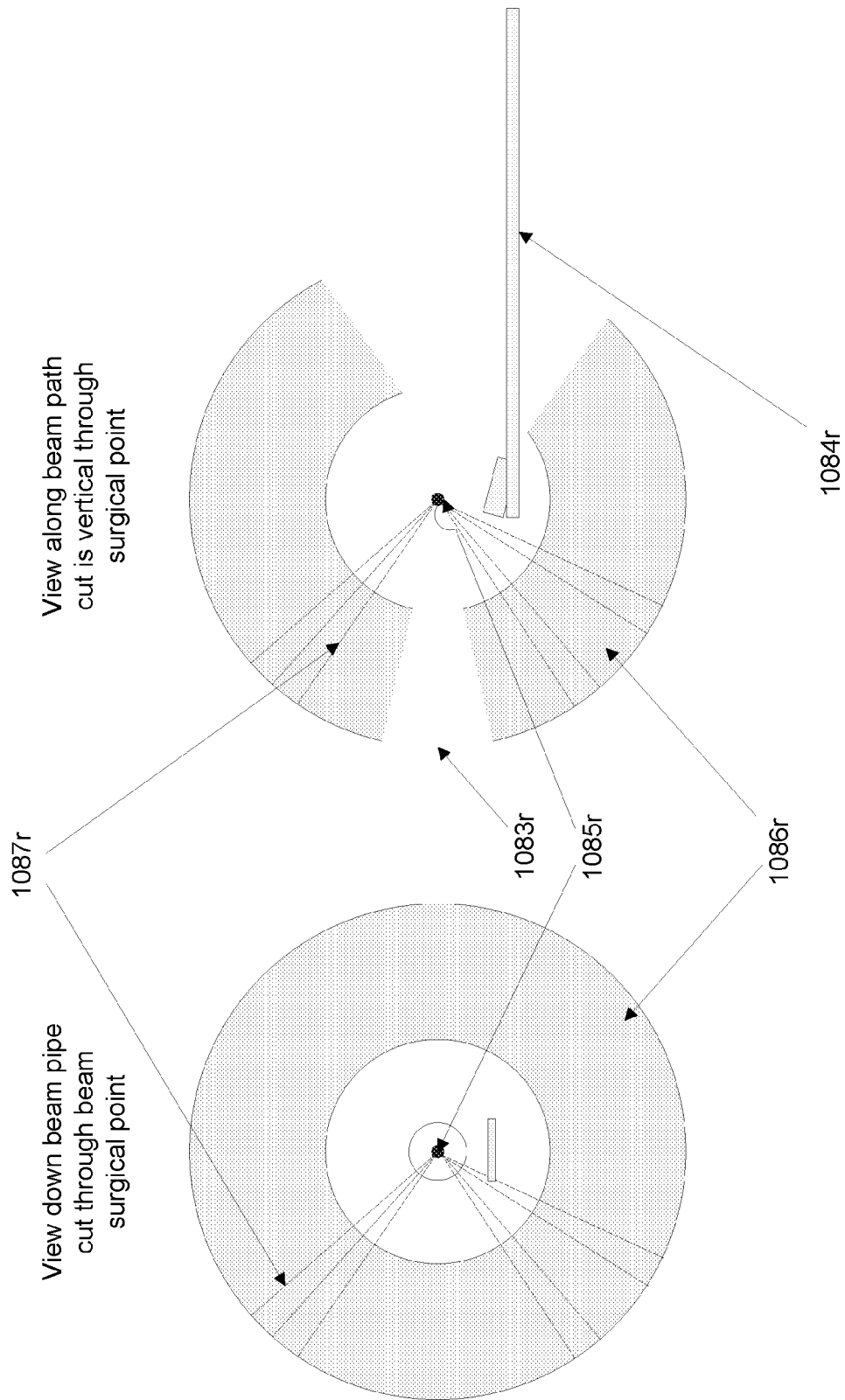

One Embodiment of a Conventional Therapy Station
Integrated with an Antiproton Treatment Protocol Station

BI-POLAR TREATMENT FACILITY FOR TREATING TARGET CELLS WITH BOTH POSITIVE AND NEGATIVE IONS

RELATED APPLICATIONS INFORMATION

This application is related to U.S. patent application Ser. No. 10/479,272, filed Aug. 29, 2002, entitled "Antiproton Production and Delivery for Imaging and Termination of Undesirable Cells," which is incorporated herein by reference in its entirety.

BACKGROUND

1. Field of the Invention

The invention relates to the use of radiation to treat medical conditions and, more specifically, to devices, procedures, and systems that controllably deliver antiprotons into a patient for the targeted termination of undesirable cells, such as cancerous cells, within the patient.

2. Background of the Invention

Numerous medical conditions are caused by the existence and/or proliferation of unwanted or undesirable cells within a patient. Such conditions include cardiovascular ailments, such as atrial fibrillation and in-stent restenosis of coronary arteries, arteriovenous vascular malformations (AVMs), cardiac arrhythmias, Parkinson's disease, orthopedic ailments, such as post-op ossification, degenerative and inflammatory arthritis and bone spurs, wet macular degeneration, endocrine disorders, such as insulinomas and pituitary adenomas, herniated or inflamed discs, ovary-related conditions, Graves opthalmoplegia, dermatological ailments, such as furunclosis, telangiectasia, Kaposi's sarcoma, genito-urinary conditions, and cancer.

More specifically, cancer is caused by the altered regulation of cell proliferation, resulting in the abnormal and deadly formation of cancer cells and spread of tumors. Cells are the basic building blocks and fundamental functioning units of animals, such as human beings. Each cell is composed of a nucleus, which contains chromosomes, surrounded by cytoplasm contained within a cell membrane. Most cells divide by a process called mitosis. While normal cells have functioning restraints that limit the timing and extent of cell division, cancerous cells do not have such functioning restraints and keep dividing to an extent beyond that which is necessary for proper cell repair or replacement. This cell proliferation eventually produces a detectable lump or mass herein referred to as a tumor. If not successfully treated, it can kill the animal host.

Cancer that initiates in a single cell, and causes a tumor localized in a specific region, can spread to other parts of the body by direct extension or through the blood stream or lymphatic vessels, which drain the tumor-bearing areas of the body and converge into regional sites containing nests of lymph nodes. The ability of cancer cells to invade into adjacent tissue and spread to distant sites (metastasize) is dependent upon having access to a blood supply. As such, tumors larger than 2 mm have a network of blood vessels growing into them, which can be highly fragile and susceptible to breakage.

Several general categories of cancer exist. Carcinomas are cancers arising from epithelial (squamous cell carcinoma) or secretory surfaces (adenocarcinomas); sarcomas are cancers arising within supporting structures such as bone, muscle, cartilage, fat or fibrous tissue; hematological malignancies are cancers arising from blood cell elements such as leukemia lymphoma and myeloma. Other cancers include brain cancers, nerve cancers, melanomas, and germ cell cancers (testicular and ovarian cancers). Carcinomas are the most common types of cancers and include lung, breast, prostate, gastrointestinal, skin, cervix, oral, kidney and bladder cancer. The most frequently diagnosed cancer in men is prostate cancer; in women it is breast cancer. The lifetime risk of a person developing cancer is about 2 in 5 with the risk of death from cancer being about 1 in 5.

Diagnosing cancer often involves the detection of an unusual mass within the body, usually through some imaging process such as X-ray, Magnetic Resonance Imaging (MRI), or Computed Tomography (CT) scanning, followed by the surgical removal of a specimen of that mass (biopsy) and examination by a pathologist who examines the specimen to determine if it is cancer and, if so, the type of cancer. Positron Emission Tomography (PET) can be used to non-invasively detect abnormally high glucose metabolic activity in tissue areas and thereby assist in the detection of some cancers. The cancer is then assigned a stage that refers to the extent of the cancer. Each cancer has a staging protocol designated by organ. Conventionally, Stage I indicates the existence of a detectable tumor under a specified size, depending on cancer type. Stage II indicates that the cancer has spread into adjacent tissue or lymph nodes. Stage III indicates that the cancer has spread beyond its own region or has grown to a minimum size qualifying it for Stage III status, and Stage IV indicates that the cancer involves another organ(s) at a distant site. Stages are typically assigned by physical examination, radiographic imaging, clinical laboratory data, or sometimes by exploratory surgery.

Once diagnosed and identified in terms of characteristics, location, and stage, the cancer is treated using one, or a combination of several, methods, including surgery, chemotherapy, and radiation. Other less commonly used treatment approaches do exist, including immunotherapy. The cancer is treated with one or several basic goals in mind: cure, prevention of spread, prolongation of survival, and/or palliation (symptom relief).

Surgery is currently a preferred treatment approach where the cancer is localized, in an early stage, and present in only one place. Preferably, the cancer is within a substantial margin of normal tissue and can be excised without unacceptable morbidity or incurring the risk of death. Moreover, for surgery to be successful, the cancer should have little potential to spread to other parts of the body. Surgery needs to be followed up by diagnostic imaging to determine if the cancer has been removed and, in many cases, subsequent adjuvant radiation and/or chemotherapy is administered.

Chemotherapy, usually employing medicines that are toxic to cancer cells, is given by injection into the blood stream or by pill. With certain limitations, the chemotherapeutic agents travel to all parts of the body and can treat cancer in any location by interfering with cell division. Although affecting cancer cells to a greater extent, chemotherapeutic agents do interfere with normal cell division as well, causing severe side effects and adverse health consequences to patients, such as kidney failure, severe diarrheas, or respiratory problems. Certain agents are highly toxic to the heart, reproductive organs, and/or nerves. Almost all are toxic to the bone marrow, which is responsible for the production of the white and the red blood cells and platelets. Because white blood cells such as granulocytes, monocytes and lymphocytes, are primarily responsible for fighting infections and platelets are essential for clotting, chemotherapeutic agents often cause patients to be highly susceptible to infections and spontaneous bleeding. Other side effects include nausea and ulcerations. The course of chemotherapy requires a number of dosage cycles to attack cancer cells, permit healthy cells to recover, and then again attack the target cancer cells. Depending on the patient's response, a decision is made to either stop treatment or continue with some sort of maintenance dosage.

Radiation therapy is the exposing of cancerous cells to ionizing radiation with the objective of terminating those cells over one or several division cycles. Conventionally, radiation is delivered by sending an energy beam, typically x-rays, through a pathway containing healthy tissue and into the target cancerous region. Because energy is being driven through healthy tissue, medical practitioners must determine the best way to deliver sufficient energy to kill a plurality of cancerous cells without generating unacceptable levels of collateral damage to adjacent normal tissue. Several factors should be taken into account, including, for example: 1) the energy deposition profile, which determines what amount of energy a particular radiation beam, having a particular energy level, will deliver to the pathway relative to the target cancer cells, 2) the amount of energy needed to terminate cancerous cells, which determines the threshold level of energy that needs to be delivered to the target site and, consequently, what amount of collateral damage may have to be tolerated in order to do so, and 3) the size, shape, and location of the tumor, which is used to calculate the requisite radiation dosage and determine the appropriate configurations by which radiation beams can be delivered to the target site.

Conventional radiation therapies are frequently unable to deliver sufficiently high levels of radiation to a target region without generating unacceptably high levels of collateral damage. The most common radiation therapy, x-ray (or photon), has a linear energy transfer (LET) profile that varies with depth. The LET of photon radiation increases initially and then decreases with depth, often depositing more energy in intervening tissue than in the target tumor site for deeply buried targets. Photons also continue traveling through the body, once they pass the target region, further depositing energy in healthy tissue. Photons are therefore unable to precisely target a tumor region without endangering surrounding normal tissues.

As such, x-ray radiation treatment sequentially delivers small doses of radiation (fractions) capable of terminating cancerous cells without inflicting too much damage on normal cells. Dividing cells are more susceptible to radiation damage; non-dividing (i.e. resting cells) are less susceptible. X-ray radiation is very often delivered using multiple fields that are required to avoid repeatedly exposing a single healthy tissue pathway to lethal radiation. For example, a typical treatment regimen may require 20-25 exposures in which 200 RADS (Radiation Adsorbed Dose) are delivered per day, 5 days per week for 5 weeks, resulting in a total dose of 5,000 RADS, or 50 Grays, where several of those exposures occur through different pathways having the same target region, an isocenter, in common. Frequent radiation treatments (fractionation of dose) need to occur over a large portion of the replication cycle of a particular cancer, explaining the basis for why a series of treatments over several weeks is required to treat cancer with photon radiation therapy. It should be noted that, even with treatment fractionation and using multiple dose delivery pathways, the collateral damage causes substantial adverse health consequences, from nausea and pain to the permanent disruption of mucosal linings surfaces and adjacent supporting structures.

Proton therapy is another form of radiation therapy currently being used to treat cancer. Relative to other conventional approaches, protons have improved physical properties for radiation therapy because, as a radiation source, they are amenable to control, and thus the radiation oncologist can more precisely shape dose distribution inside a patient's body. Therefore, the dose delivered by a proton beam may be better localized in space relative to conventional radiation therapies, both in the lateral direction and in depth, causing more destruction at a target site with correspondingly less collateral damage.

As shown in FIG. 1, where the target tumor site is at a depth of 25 cm, a mono-energetic proton beam 110 deposits the same energy dosage as a beam of photon energy 105 at the target point. However, the collateral damage, represented by the difference 115, 120 in the areas under the curves between the energy dosages of the two respective beams 110, 105 (measured in areas outside the target region 125), is far greater for the photon beam 105. As a result, the proton beam 110 delivers the same termination power at the tumor site with correspondingly less collateral damage.

A substantial amount of investment has been made in researching proton therapies and building and deploying a proton therapy infrastructure, including proton accelerators, proton delivery devices, such as proton gantries, and specialized medical facilities. Despite this substantial investment, proton therapy still has several significant disadvantages. Most significantly, while the energy deposition profile in proton radiation represents an improvement over conventional approaches, it still does not deliver sufficient amount of termination power at a tumor site relative to the collateral damage it causes.

Another cancer therapy, heavy ion therapy, uses a heavy ion, namely an atom (e.g., a carbon atom) that has been stripped of its electrons, to deliver cancer cell terminating energy to a target region. Like proton beam therapy, heavy ion therapy has the ability to deposit energy directly into the cancerous tumor in three dimensions, hence the dose delivered by the heavy ion beam may also be better localized in space relative to conventional radiation therapies both in lateral direction and in depth. Heavy ions deposit more energy into a tumor than do protons and hence have more cancer cell killing capability than do protons. Heavy ions do have the capability of killing resting cells, but while the killing power deposited on the tumor for ion therapy is dramatically greater, the collateral damage to healthy intervening tissue (that issue between the skin surface and the tumor) is likewise greater even greater collateral damage than for conventional radiation. In fact, collateral damage inflicted by heavy ion therapy can be even greater than the direct damage to the tumor with proton therapy. Additionally, in certain heavy ion therapy applications, treatment imaging is enabled by the fragmentation of the heavy ion, such as $^{12}C$, as it approaches a patient in-beam and as it strikes cells while traveling through a patient. The heavy ion fragments into isotopes that may be imaged through conventional PET detection, that being $^{11}C$ in the case of $^{12}C$ heavy ion therapy. This imaging process is not, however, real-time in that imaging is delayed until the radioisotope decays and is substantially complicated by the migration of the isotope within the tumor

SUMMARY

A system for treating target cells with both positive and negative ions comprises a bi-polar beam delivery system configured to create and deliver both positive ion beams and negative ion beams. The bi-polar beam delivery system comprises a bi-polar accelerator configured to accelerate positive and negative ions in the same direction making such a bi-polar beam delivery system practical.

In one aspect, the bi-polar accelerator comprises arced sections, possibly several straight sections, and a plurality of bending magnets configured to direct the positive and negative ions around the arced sections.

In another aspect, the bi-polar beam delivery system also comprises a configurable power supply coupled with the plurality of bending magnets, the configurable power supply configured to supply a reversible current to the bending magnets so as to reverse the polarity of the magnetic field generated by the bending magnets as required to accelerate both positive and negative ions in the same direction.

These and other features, aspects, and embodiments of the invention are described below in the section entitled "Detailed Description."

BRIEF DESCRIPTION OF THE DRAWINGS

Features, aspects, and embodiments of the inventions are described in conjunction with the attached drawings, in which:

FIG. 10b is a diagram illustrating an example antiproton delivery device combined with a detector array in accordance with another embodiment;

FIG. 10c is a diagram illustrating an example detector array that can be used in the delivery devices of FIGS. 10a and 10b, taken from a beam pipe perspective, using PbWO$_4$ as a calorimeter element and applied to brain imaging;

FIG. 10d is a diagram illustrating a side view of the detector array of FIG. 10c as applied to brain imaging;

FIG. 10e is a diagram illustrating an example detector array that can be used in the delivery devices of FIGS. 10a and 10b, taken from a beam pipe perspective, using PbWO$_4$ as a calorimeter element and applied to torso imaging;

FIG. 10f is a diagram illustrating a side view of the detector array of FIG. 10e as applied to torso imaging;

FIG. 10g is a diagram illustrating an example detector array that can be used in the delivery devices of FIGS. 10a and 10b, taken from a beam pipe perspective, using CsI(Tl) as a calorimeter element and applied to brain imaging;

FIG. 10h is a diagram illustrating a side view of the detector array of FIG. 10g as applied brain imaging;

FIG. 10i is a diagram illustrating an example detector array that can be used in the delivery devices of FIGS. 10a and 10b, taken from a beam pipe perspective, using CsI(Tl) as a calorimeter element and applied to torso imaging;

FIG. 10j is a diagram illustrating a side view of the detector array of FIG. 10i as applied to torso imaging;

FIG. 10k is a diagram illustrating an example detector array that can be used in the delivery devices of FIGS. 10a and 10b, taken from a beam pipe perspective, using Ir as a calorimeter element and applied to brain imaging;

FIG. 10l is a diagram illustrating a side view of the detector array of FIG. 10k as applied to brain imaging;

FIG. 10m is a diagram illustrating an example detector array that can be used in the delivery devices of FIGS. 10a and 10b, taken from a beam pipe perspective, using Ir as a calorimeter element and applied to torso imaging;

FIG. 10n is a diagram illustrating a side view of the detector array of FIG. 10m as applied to torso imaging;

FIG. 10o is a diagram illustrating an example detector array that can be used in the delivery devices of FIGS. 10a and 10b, taken from a beam pipe perspective, using W as a calorimeter element and applied to brain imaging;

FIG. 10p is a diagram illustrating a side view of the detector array of FIG. 10o as applied to brain imaging;

FIG. 10q is a diagram illustrating an example detector array that can be used in the delivery devices of FIGS. 10a and 10b, taken from a beam pipe perspective, using W as a calorimeter element and applied to torso imaging;

FIG. 10r is a diagram illustrating a side view of the detector array of FIG. 10q as applied to torso imaging;

DETAILED DESCRIPTION

The embodiments disclosed herein are related to methods and systems for the use of antiprotons for the termination of cells, including, but not limited to use for the treatment of medical conditions caused by existing or proliferating unwanted or undesirable cells, such as cancer, and the accompanying devices, systems, and processes to conduct such treatments. Such conditions include cardiovascular ailments, such as atial fibrillation and in-stent restenosis of coronary arteries, arteriovenous vascular malformations (AVMs), cardiac arrhythmias, Parkinson's disease, orthopedic ailments, such as post-op ossification, degenerative and inflammatory arthritis and bone spurs, wet macular degeneration, endocrine disorders, such as insulinomas and pituitary adenomas, herniated or inflamed discs, ovary-related conditions, Graves opthalmoplegia, dermatological ailments, such as furunclosis, telangiectasia, Kaposi's sarcoma, genito-urinary conditions, and cancer. While the detailed description provided herein primarily discusses the application of certain example systems and methods to the termination of cancerous cells, one of ordinary skill in the art will appreciate that the methods and systems can be applied to the termination of any type of unwanted or undesirable cell. The specific use of cancer in the present description should not be interpreted to limit the application of the methods and systems to the treatment of cancer. Furthermore, unwanted and undesirable shall be used interchangeably to describe the cells which are the preferred targets of the antiprotons as described herein.

Antiprotons have been identified as a preferential radiation source for the treatment of cancer for several reasons. First, as discussed herein, antiproton production and distribution are now technically and economically feasible, making antiprotons a viable radiation source for medical treatments.

Second, as antiprotons travel through a substance, such as human tissue, they transfer energy in a manner similar to other charged particles. As with protons, antiprotons lose kinetic energy as they pass through a substance, causing collateral damage to the healthy tissue pathway. The theory of energy loss for a charged particle can be described by the following equation, where the stopping power (dE/dx) in MeV is approximated using $\rho$ (g/cm$^3$) as the density of the medium, $\beta$ is the velocity (v/c) of the moving particle, $f(\beta) = \ln(2 mc^2 \beta^2/(1-(\beta^2))) = \beta^2$, m is the mass of the electron (0.51 MeV/c2), and $Z_i$, $A_i$, $C_i$ and $I_i$ (MeV) are the atomic number, weight, concentration, and excitation potential of the $i^{th}$ element, respectively.

$$-\frac{1}{\rho}\frac{dE}{dX} = \frac{0.30708}{\beta^2} \cdot \sum \frac{Z_i \cdot C_i}{A_i} \{f(\beta) - \ln I_i\}$$

Figure 1:
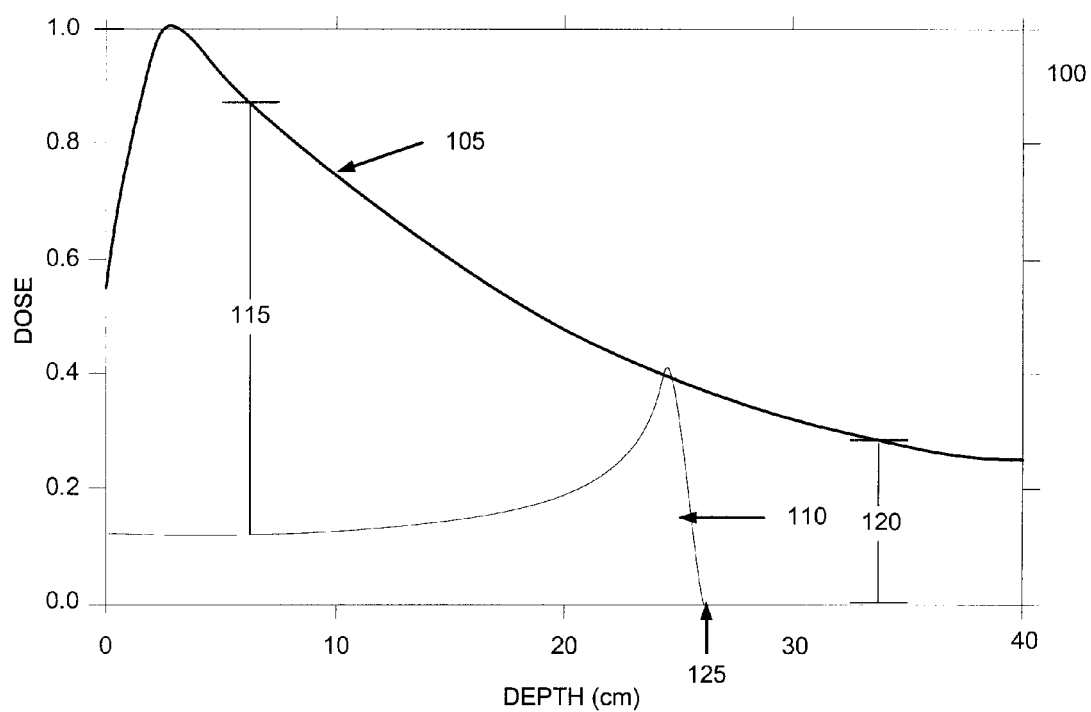
FIG. 1 is a graph illustrating the energy deposition as compared to depth for conventional radiation therapies.

As the velocity of a charged particle decreases, the stopping power increases rapidly because of the inverse proportional dependence on particle velocity ($\beta^2$). The result is a very large energy deposition toward the end point which, in the case of cancer therapy, is in the tumor itself. The large final energy deposition causes a sharp Bragg Peak, as shown in FIG. 1 for proton therapy.

Figure 1A:
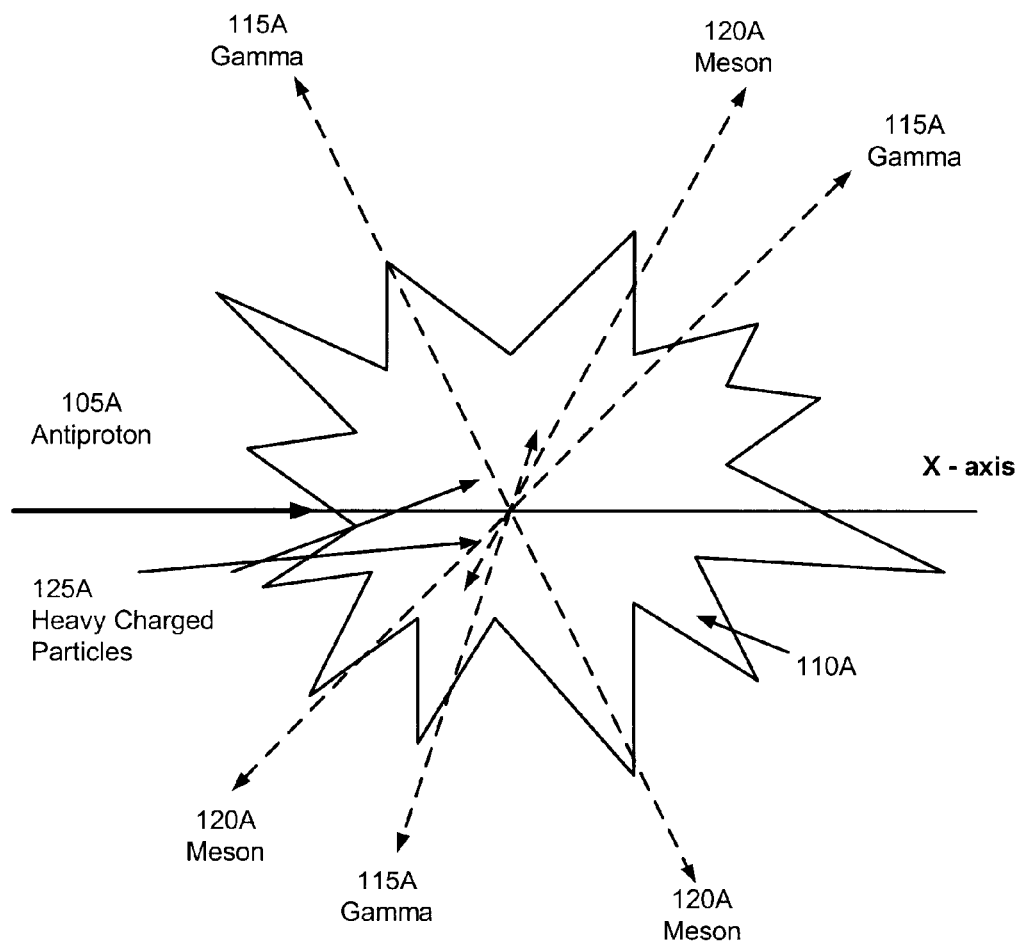
FIG. 1a is a diagram illustrating a typical antiproton annihilation event.

Unlike protons, however, antiprotons undergo a highly energetic annihilation event, releasing a plurality of charged and neutral particles and causing a much greater amount of damage in the target region, once they slow down in the target area and become captured in a nucleus or as they pass through the target area. Referring to FIG. 1a, when an antiproton 105a comes to rest with a nucleus, it generates an annihilation event 110A, in which several by-products are generated, including gamma radiation 115A, mesons (both charged and neutral pions) 120A, and heavy charged particles 125A. The heavy charged particles are highly destructive to nuclei adjacent to the annihilation site and, therefore, propagate the damage incurred from the initial antiproton annihilation to adjacent cells, thereby terminating more cells in the course of a single antiproton exposure. This unique annihilation event allows for the targeted, localized delivery of larger amounts of cell-terminating radiation with substantially similar amounts of collateral damage, thereby permitting cancer treatment regimens that do not require fractionated treatment protocols. The nature of this annihilation event is an important element in the proper determination of dosage and to the real-time imaging process, as later discussed herein.

Figure 2:
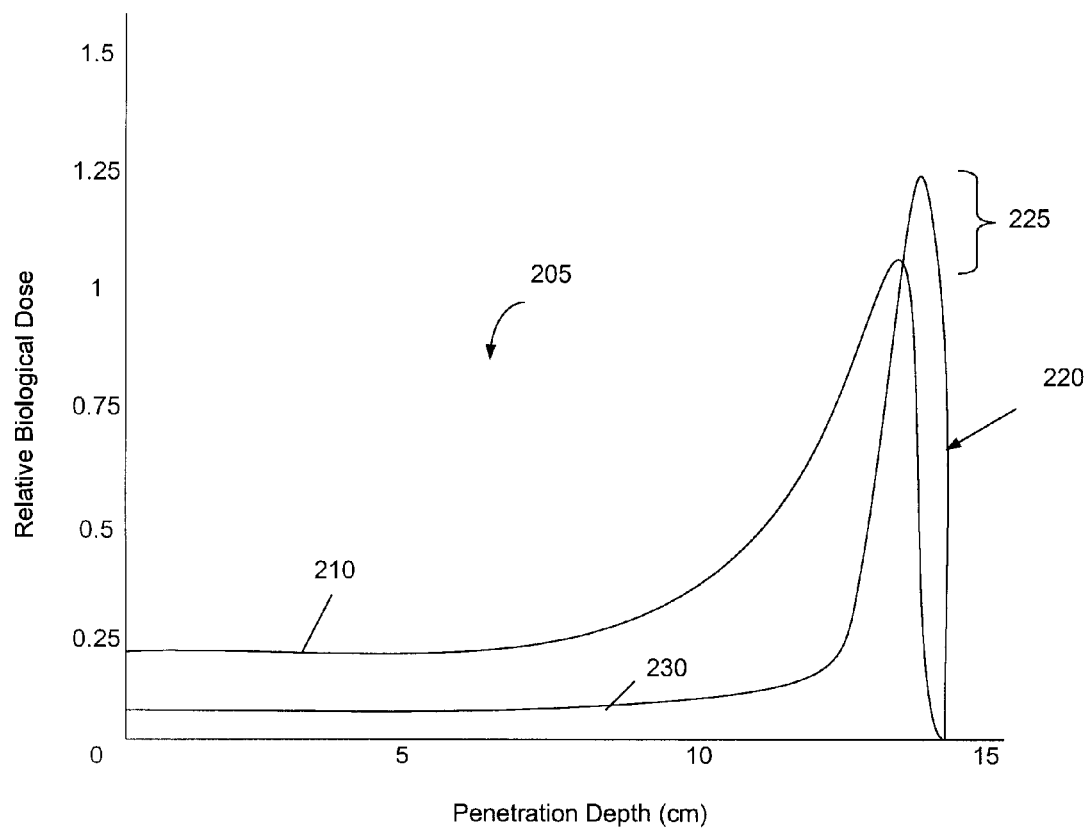
FIG. 2 is a graph illustrating the energy deposition as compared to depth for conventional radiation therapies as compared to antiproton therapy performed in accordance with one embodiment.

Referring to FIG. 2, the relative doses (arbitrary units) of various radiation sources are shown in relation to depth of energy deposition in tissue. A target tumor site 203 is identified at a particular depth, such as 11-12 cm. A mono-energetic proton beam 210 delivers a relative biological dose of 1, as compared to a beam of photon energy 205, which delivers a relative biological dose of approximately 0.65. An antiproton beam 220 substantially overlays with the proton beam 210, but has a greater relative dose at greater than 1.2, the difference being represented by 225. Despite the greater relative dose, the antiproton beam 220 has substantially similar amounts of collateral damage compared to the proton beam 210 and far less collateral damage compared to the photon beam 205, the collateral damage being caused by the deposition of energy over the region 230 between the skin surface and tumor site. As a result, the antiproton beam 220 delivers the greater termination power at the tumor site 203 with correspondingly less collateral damage (the difference in collateral damage determined by taking the difference between the integrated areas under beam curve 210 and beam curve 220 calculated over region 230). From a different perspective, for the same collateral damage, the antiproton beam can deliver far greater termination power at the tumor site relative to proton and photon radiation sources.

Figure 3:
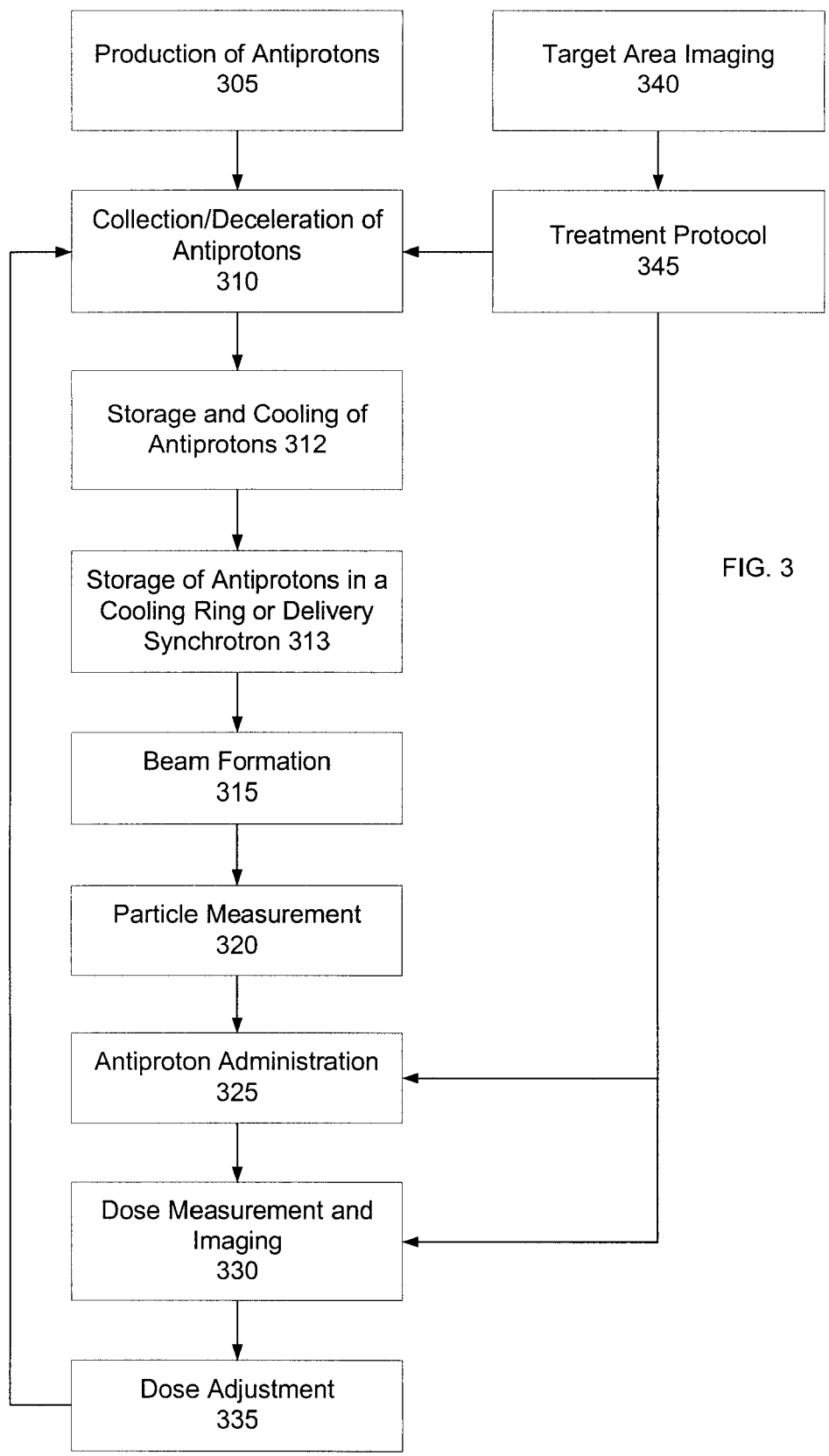
FIG. 3 is a flowchart illustrating an example method for performing antiproton therapy in accordance with one embodiment.

One example embodiment, as diagrammed in FIG. 3, comprises the production of antiprotons 305, the collection and then deceleration of antiprotons to a desired energy level 310, the storage and cooling of antiprotons 312, the storage of antiprotons in a cooling ring or delivery synchrotron 313, the formation of antiprotons into an administrable beam 315, the measurement of antiprotons to determine the actual number being delivered 320, the delivery of that measured beam via an antiproton delivery and imaging device to a prepared patent 325, optionally though preferably the dose measurement and imaging of the resultant radiation event and comparison of that image to previously recorded images of the target area 330, and, optionally, though preferably, the adjustment of dosage characteristics to insure the impacted area, as imaged, aligns with the desired target area 335. Prior to the delivery step, a patient had been prepared, optionally, though preferably, by imaging the target area 340 using imaging technologies, to confirm the size, location, and configurational characteristics of the target tumor, and determining an appropriate treatment regimen in light of the tumor characteristics 345. A patient is then securely positioned relative to the antiproton delivery and image device. The treatment regimen data informs the extent of deceleration 310 (i.e. the predetermined delivery energy of the antiprotons useful for treatment), antiproton delivery methodology 325, and the dose measurement and imaging of the resultant radiation event and comparison of that image to previously recorded images of the target area 330.

Figure 4:
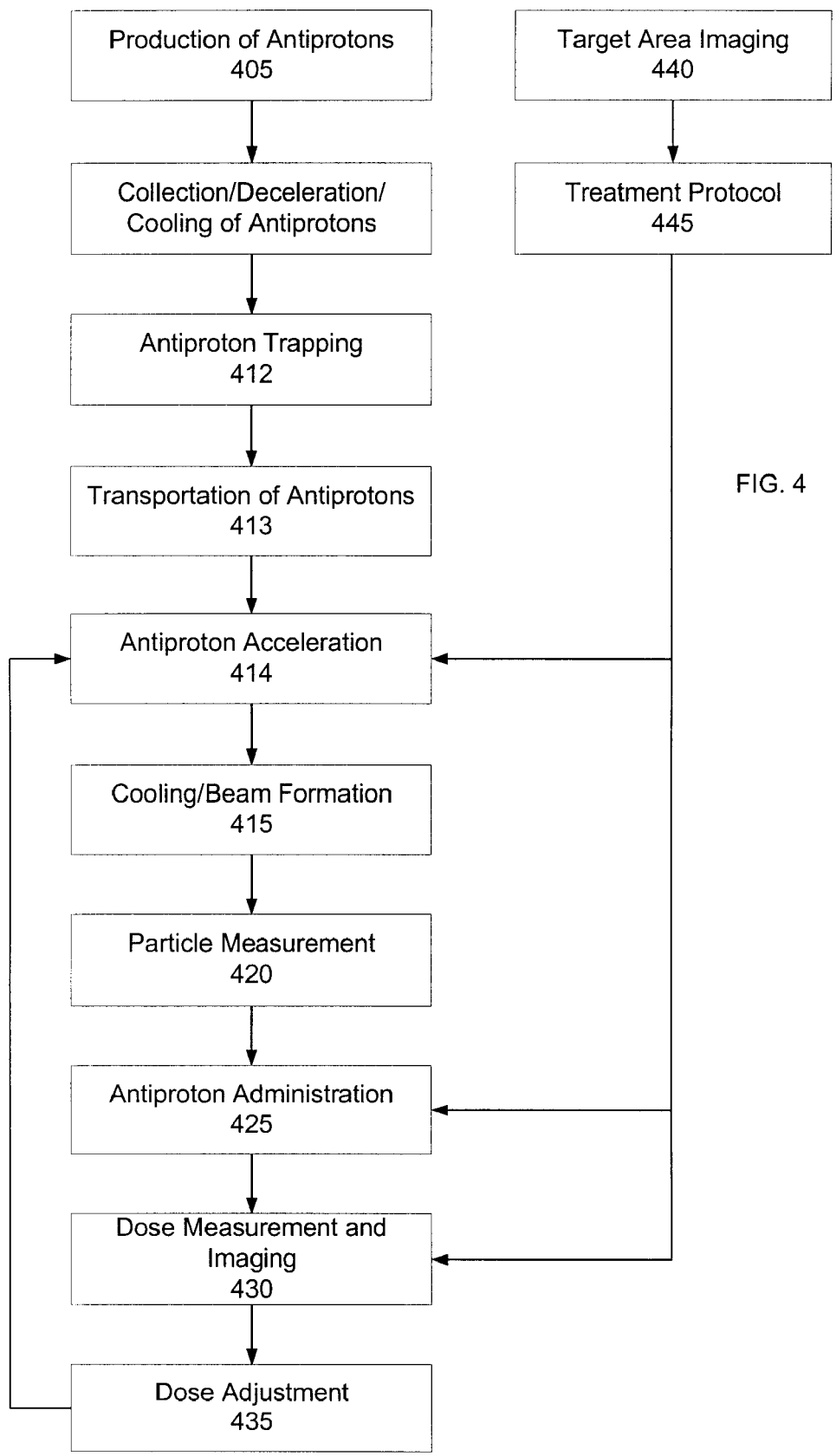
FIG. 4 is a flowchart illustrating an example method for performing antiproton therapy in accordance with another embodiment.

Another embodiment, as diagrammed in FIG. 4, comprises the production of antiprotons 405, the collection, deceleration and cooling of antiprotons 410, the trapping of cooled and slowed antiprotons into a trap device 412, the transport of the trap device to a medical facility 413, the reception and acceleration (i.e. to a suitable energy) of antiprotons at the medical facility 414, the cooling and formation of antiprotons into an administrable beam 415, the measurement of antiprotons to determine the actual number being delivered 420, the delivery of that measured beam via an antiproton delivery and imaging device to a prepared patient 425, optionally though preferably the dose measurement and imaging of the resultant radiation event and comparison of that image to previously recorded images of the target area 430, and, optionally though preferably, the adjustment of dosage characteristics to insure the impacted area, as imaged, aligns with the desired target area 435. Prior to the delivery step, a patient had been prepared, optionally though preferably, by imaging the target area 440 using imaging technologies, to confirm the size, location, and configurational characteristics of the target tumor, and determining an appropriate treatment regimen in light of the tumor characteristics 445. A patient is then securely positioned relative to the antiproton delivery and image device. The treatment regimen data informs the extent of antiproton acceleration (i.e. the delivery energy of the antiprotons needed for treatment) 414, antiproton delivery methodology 425, and the dose measurement and imaging of the resultant radiation event and comparison of that image to previously recorded images of the target area 430.

These embodiments, along with other embodiments, shall be discussed in greater detail in each of the subsequent sections.

1. Antiproton Production

Antiprotons for use in the systems and methods disclosed herein can be generated by any method. The antiproton generation process is described herein using a circular accelerator, such as the one found at Fermi National Laboratory in Batavia, Ill. It should be noted, however, that the Fermi accelerator has been designed to generate antiprotons having far greater energies than that which are generally preferred for use in connection with the systems and methods disclosed herein. Although such antiprotons may be effectively altered to suit the methods, as discussed below. Different accelerators, such as a circular accelerator that accelerates particles to energies lower than those achieved by Fermi National Accelerator Laboratory, can also be effectively used in the context of the methods and systems described herein.

Figure 5:
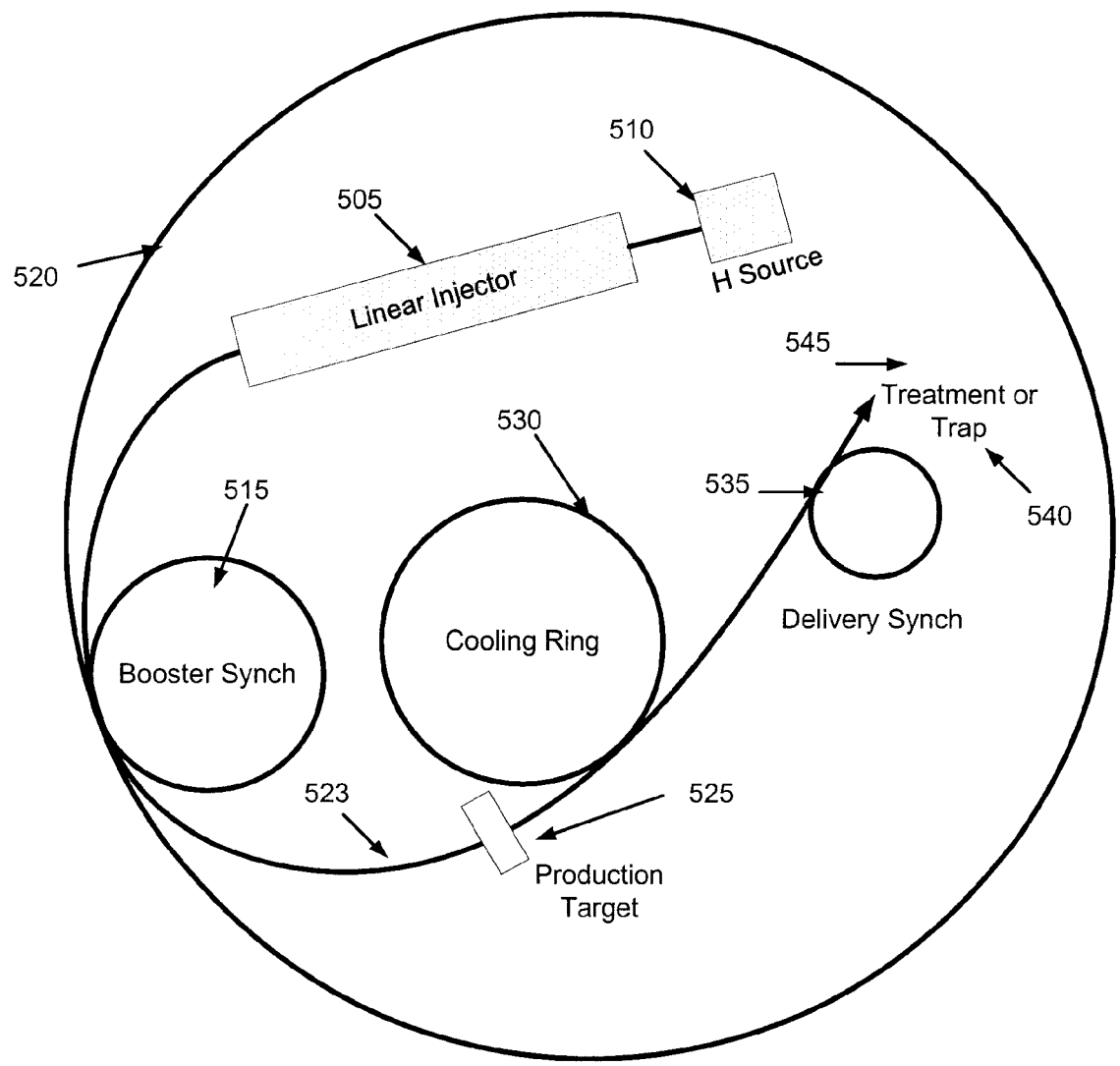
FIG. 5 is a diagram illustrating an example antiproton production facility.

In one example embodiment, antiproton production comprises a six-stage process, culminating in the deceleration of antiprotons for medical application or storage and trapping, as discussed in the subsequent sections. Referring now to FIG. 5, a device (not shown), an exemplary embodiment of which is a Cockroft-Walton is used to add electrons to hydrogen atoms delivered from a source 510, resulting in negative ions consisting of two electrons and one proton. The device applies a positive voltage to the negative ions, thereby accelerating them. In one embodiment, the negative ions are accelerated to an energy of approximately 750 keV.

In the embodiment of FIG. 5, the negative ions are transferred from the Cockroft-Walton device and enter into a linear accelerator (or a Linear Injector) 505, referred to as a Linac, which comprises a plurality of tanks filled with tubes spaced varying distances apart. An electric field is applied to the tubes, repeatedly reversing in direction, causing the negative ions to alternately hide in tubes when the electric field, as applied, will slow them down, and emerge into gaps between the tubes when the field is of a direction that accelerates them. The Linac 505 further increases the energy of the ions to approximately 400 MeV. The negative ions are passed through a carbon foil, thereby removing the electrons and leaving protons, which are then passed into a booster synchrotron 515. The booster synchrotron 515 is a circular accelerator, a rapid cycling synchrotron that forces the positively charged particles to travel in a circular path through the application of magnetic fields. Through each revolution, the protons experience the repeated application of accelerating electric fields and therefore increase in energy. In one embodiment, the booster 515 raises the energy level of protons to about 8 GeV, cycles approximately 12 times in rapid succession, and introduces about 12 proton packets (pulses) into the main accelerator ring 520, which is a synchrotron that further accelerates the protons to about 150 GeV. In the embodiment, the accelerator 520 is approximately four miles in circumference with a tunnel ten feet in diameter and housing approximately 1,000 copper-coiled magnets to bend and focus the protons. In another embodiment, the booster 515 introduces proton packets into a 14 GeV main accelerator ring 520.

Figure 6:
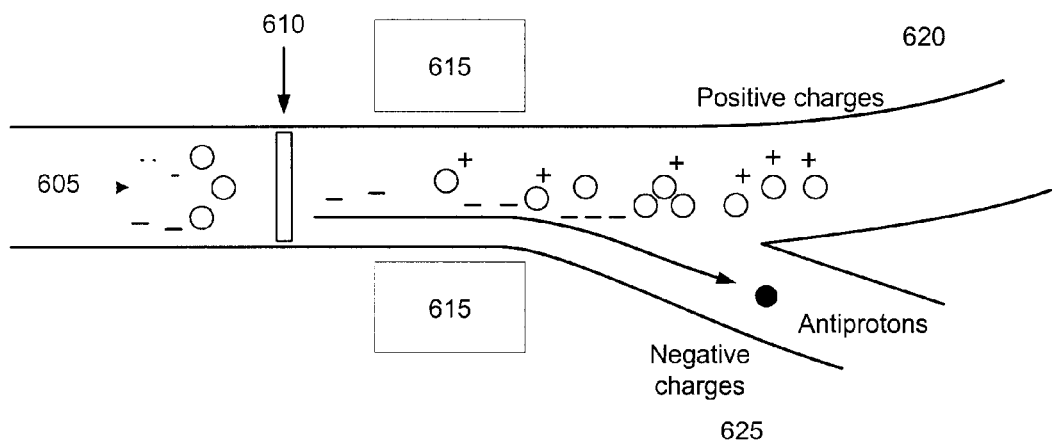
FIG. 6 is a diagram illustrating antiproton generation using the facility of FIG. 5.

In this embodiment, antiprotons are produced by extracting bunches of approximately 120 GeV protons from this synchrotron ring 520, transporting them via a beamline 523 to a production target 525, and focusing them on the target 525. In other embodiments, the protons can be at other energies as would be recognized by those skilled in the art. The proton collisions with the target 525 produce a number of particles, including antiprotons. The produced antiprotons are selected, as shown in FIG. 6, and transported to a ring 530 where they are debunched and then cooled, e.g., by a process referred to as stochastic cooling.

In this context, beam cooling is the technique where both the physical size and energy spread of a particle beam circulating in a cooling/storage ring are reduced with little accompanying beam loss, as further discussed below. Subsequently, the antiprotons are transferred to another ring 535 for deceleration or acceleration to appropriate energies for delivery to a specialized antiproton trap 540, to a treatment system 545 or for accumulation and/or storage.

Antiprotons are created by the interaction of high-energy protons with nuclei in the target area. Referring now to FIG. 6, a schematic diagram of antiproton production is provided. Protons 605 having an energy level are focused on, and impact, a target 610. The target is preferably comprised of a metallic material that is relatively easy to remove heat from, such as copper, nickel, or iridium. In approximately one collision per million, an antiproton-proton pair is formed. In one operation, approximately 10 trillion protons impinge on the target per minute, generating 10 million antiprotons. Using magnets 615, antiprotons are separated from the positively charged protons and directed toward a system and process for cooling the antiproton beam.

As previously stated, antiprotons can be created in a number of different ways. In another embodiment, protons are accelerated in a linear accelerator, a booster, and then a synchrotron up to about 27 GeV. The protons are focused onto a target, such as the materials mentioned above, and, in the interaction of the protons with the target nuclei, produce many particle-antiparticle pairs, including proton-antiproton pairs.

One of ordinary skill in the art will appreciate that the systems and methods described herein is not limited to the above-described antiproton generation methods. For example, other methods and systems for generating negative hydrogen ions, not simply a Cockroft-Walton device may be used. Additionally, while specific energy levels have been described, other methods can be effectively performed by generating antiprotons from protons accelerated to any appropriate range, such as approximately 12 GeV/c, 11 GeV/c, 10 GeV/c, 13 GeV/c, among other values. In certain embodiment, a circular accelerator with a smaller circumference is used to generate protons and antiprotons at lower energy levels, thereby allowing for a more cost-effective antiproton production method.

The process of producing antiprotons results in a plurality of antiprotons moving at high momentum, with varying energies (referred to as energy spreads) and directions (referred to as transverse oscillations). To commercially deploy antiprotons, however, such energy spreads and transverse oscillations are preferably reduced. The term "cooling" refers to the reduction of the beam's transverse dimensions and energy spread.

Electric fields are preferably applied to antiprotons, as they travel through a vacuum pipe ring structure. Within the radio frequency cavities, as antiprotons decelerate, the size of their transverse oscillations increase. If not managed properly, a substantial number of antiprotons can be lost in this process. Among the cooling methods that may be used to avoid excessive antiproton loss are stochastic cooling and electron cooling. Electron cooling uses an electron beam merged with the antiproton beam to act as a heat exchanger and is more effective at low energy. In stochastic cooling, the beam is positionally sampled by a monitor and an error signal generated in a monitor is fed back, via a corrector, to the beam sample that created it. This process eventually centers the sample's characteristics towards an average value, after a large number of passages through the apparatus.

In certain embodiments, generated antiprotons are decelerated to an energy level suitable for the particular medical treatment methodology being employed. More specifically, where a medical facility is located proximate to the antiproton generation location, generated antiprotons are preferably slowed from their generation energies to a medically beneficial energy level, such as between 1 MeV and 300 MeV, preferably around 250 MeV, and delivered directly to a patient, as further discussed below. To do so, a deceleration, cooling, and collection process is performed. Antiprotons are decelerated to a low energy level, for example between 1.5 and 3 GeV/c, or alternatively, they are generated at that energy. In one embodiment, the deceleration process is performed using the aforementioned cooling techniques in a separate, dedicated deceleration ring. In another embodiment, this first deceleration step is unnecessary because a low-energy antiproton production method is used and consequently generates low energy antiprotons, such as in the 1.5-3 GeV/c range. It should be noted that the 1.5-3 GeV/c energy range is not meant to be restrictive of the low energy range.

Once in the 1.5 GeV/c range, antiprotons are collected and further decelerated to a medically beneficial energy level, such as about 250 MeV. In one example embodiment, this collection and second deceleration stage is conducted by employing the aforementioned cooling and deceleration techniques in a dedicated cooling and deceleration ring. The antiprotons can be stored either in the cooling ring or in the delivery synchrotron. As discussed below, the antiprotons, once a medically beneficial energy level, are introduced via a beam line to a patient, a controlled, adjustable energy level, through a number of alternative antiproton delivery devices.

Alternatively, where a medical facility is not proximate to an antiproton production location, preferably antiprotons are produced, stored, and transported to facility sites. Antiprotons are therefore similarly decelerated down to an appropriate level, after which the antiprotons are squeezed out in groups, referred to as bunches, and ejected through the application of a kicker magnet which leads the ejected antiprotons through a separate line into an accumulator, collector, or some other storage device.

A person familiar with high-energy physics will understand how to produce, collect, cool, decelerate and extract antiprotons through the application of vacuums pumps, magnets, radiofrequency cavities, high voltage instruments and electronic circuits. Antiprotons circulate inside vacuum pipes in order to avoid contact with matter with which they annihilate. The vacuum should be as high as possible and therefore several vacuum pumps, which extract air, are placed around the pipe. The magnets used include dipoles, which serve to change the direction of antiproton movement and insure they stay within the circular track, and quadrupoles, which are used as lenses or focusing magnets to insure that antiproton beam size is smaller than the vacuum pipe size. Electric fields are used to modify antiproton energy levels and are provided for by radio-frequency cavities that produce high voltages synchronized with the rotation of antiprotons around the ring.

Antiprotons may either be stored in a ring for future use or in traps for distribution to antiproton medical facilities. In one embodiment, antiprotons are stored in traps, such as those disclosed in U.S. Pat. Nos. 6,160,263 and 5,977,554 which are incorporated herein by reference. The trapped antiprotons are inserted into a linear accelerator or synchrotron, accelerated to appropriate energy levels, and then formed into a beam for use in treatment. Operationally, the trap is attached to an inlet port that interfaces with a Linac or RFQ. The electric field used to trap the voltage is decreased while an attracting field is generated in the accelerator, causing the antiprotons to drift into the accelerator structure. Antiprotons therefore drift from the trap at very low energies, on the order of about 10-20 KeV. Once the antiprotons are positioned inside the accelerator, they are accelerated to an appropriate energy level. The delivery synchrotron is preferably designed to be stable at 1 MeV-300 MeV energy levels and will result in antiprotons being delivered at certain minimum energies, which can be accelerated by using a small Linac or an RFQ. An exemplary cyclotron will preferably be designed for the production of an antiproton beam, i.e. 1.5 mAproton current at 590 MeV.

Whether obtaining the antiprotons from a decelerator attached to the main antiproton production source or obtaining antiprotons from a trapped state and accelerating them, a main antiproton beam is generated. The beam is stored and conditioned in a delivery synchrotron. The stored antiprotons can then be adjusted to an appropriate energy level while in the delivery synchrotron. Adjustment of the energy can be readily achieved such as by using the rapid-cycling energy characteristic of the delivery synchrotron or by using a set of carbon or copper degrader blocks, or a combination of the two methods. In a combination mode, the energy of the beam can be adjusted by changing the arrangement of the degrader blocks to provide variable degrader thicknesses to the beam and by tuning the beam line to the appropriate delivery momentum. In one example embodiment, no degrader blocks are used to adjust the beam energy, as the degrader processes may produce spurious particle emissions such as undesired neutrons. Spurious particle emission is generally avoided if the delivery synchrotron is adjusted to provide particles of the desired target energy level directly. A calculated number of antiprotons at the correct energy is then split off the stored beam using an electrostatic splitter for delivery to a patient.

For medical applications, the target energy level may vary between about 1 MeV and 300 MeV, preferably about 250 MeV and including 5 MeV, 10 MeV, 15 MeV, 20 MeV, 25 MeV, 30 MeV, 35 MeV, 40 MeV, 45 MeV, 50 MeV, 55 MeV, 60 MeV, 65 MeV, 70 MeV, 75 MeV, 80 MeV, 85 MeV, 90 MeV, 95 MeV, 100 MeV, 105 MeV, 110 MeV, 115 MeV, 120 MeV, 125 MeV, 130 MeV, 135 MeV, 140 MeV, 145 MeV, 150 MeV, 155 MeV, 160 MeV, 165 MeV, 170 MeV, 175 MeV, 180

MeV, 185 MeV, 190 MeV, 195 MeV, 200 MeV, 205 MeV, 210 MeV, 220 MeV, 225 MeV, 230 MeV, 235 MeV, 240 MeV, 245 MeV, 250 MeV, 255 MeV, 260 MeV, 265 MeV, 270 MeV, 275 MeV, 280 MeV, 285 MeV, 290 MeV, 295 MeV, and 300 MeV. The specific energy used at any time depends upon the particle penetration depth for the specific treatment being performed. The particle beam is preferably analyzed in momentum and phase space using beam profile monitors to insure the resultant beam is appropriately shaped and is substantially monochromatic in order to couple the beam into the delivery device. The delivery synchrotron can provide substantially monochromatic particles directly by the intrinsic nature of the synchrotron acceleration process. The shape characteristic of the particle beam can be adjustable by means of a pair of magnetic quadrupole focusing elements positioned along the delivery beam pipe. In treatments requiring high spatial resolution, the beam will be focused into a small spot size using the magnetic quadrupole focusing elements. Other treatments can use a broader, less highly focused beam. A continuous range of beam geometries between broad and sharply focused can be achieved using the magnetic quadrupole focusing elements, without affecting the monochromatic nature of the beam. The beam is then introduced into a beam line, a vacuum pipe, that is directed into the antiproton radiating and imaging device.

2. Antiproton Radiating and Imaging Device

Figure 7:
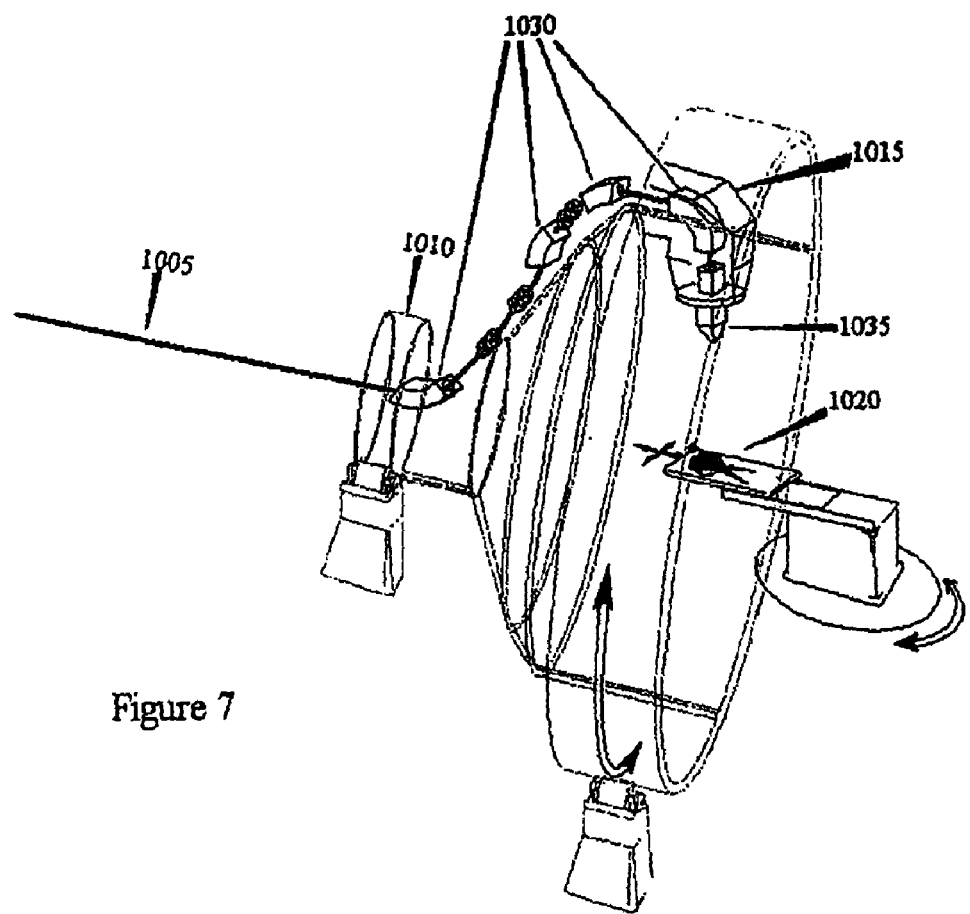
FIG. 7 is a diagram illustrating an example antiproton delivery device configured in accordance with one embodiment.

The beam line is directed through an antiproton radiating and imaging device in order to administer antiproton radiation to a patient. In one embodiment, a gantry is used to deliver antiprotons to a patient, or a proton therapy gantry is retrofitted to accept and deliver antiprotons instead of protons. Referring to FIG. 7, an antiproton gantry is shown. The antiproton gantry comprises a delivery pipe 1005 passing through a shielded support structure 1010 and into a gantry head 1015 through which the antiprotons are directed into a patient 1020. Although not required, the delivery pipe 1005 bends as it extends out from an accelerator (not shown), through the structure 1010, and into the gantry head 1015 through the application of magnets 1030. More specifically, in the illustrated embodiment, the antiproton beam (not shown) enters into the structure 1010 via the vacuum pipe 1005 and is deflected by two 35 degrees bending magnets 1030 that are parallel to the rotation axis of the gantry head 1015. Once in the gantry head 1015, the beam is directed, through the use of a magnet 1030, through a nozzle 1035 having a monitor and range shifter system (not shown), and into the patient 1020. In addition to the plurality of magnets 1030, there are preferably also focusing quadrupole magnets (not shown).

Preferably the support structure 1010 is designed to provide maximum rigidity to the beam line. The weight of the entire gantry generally is dominated by the bending magnets 1030 and appropriate balancing weights should be provided in the structure 1010 to insure the gantry does not fall, tip, or otherwise become unstable.

Figure 8:
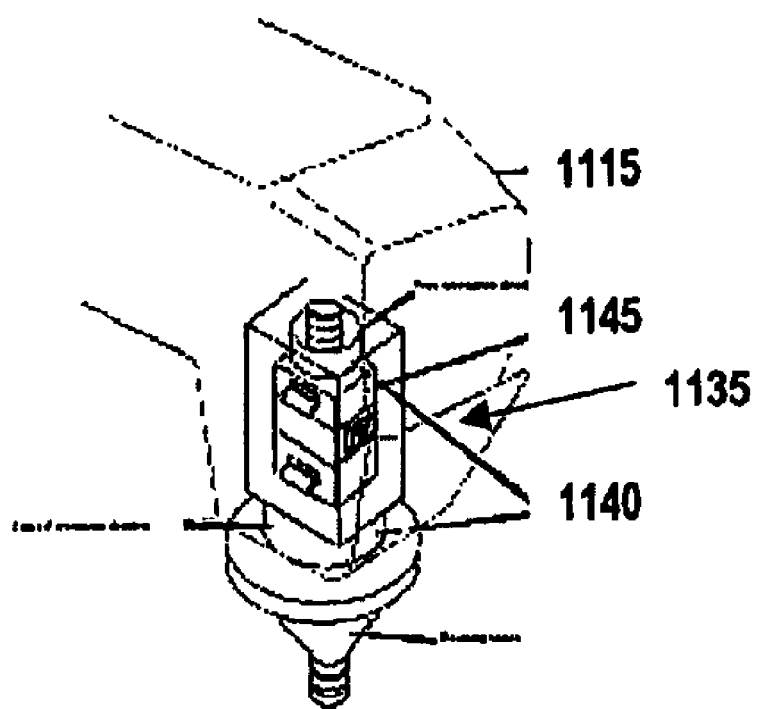
FIG. 8 is a diagram illustrating a closer view of a nozzle assembly that can be included in the delivery device of FIG. 7.

Operationally, the antiproton beam is deposited in the patient as a sequence of sequential, directed applications. Referring to FIG. 8, the number of antiprotons delivered in a single, directed application is measured by the beam monitor system 1140 positioned in the nozzle 1135. In one embodiment, the beam monitoring system comprises two monitoring subsystems providing two independent beam flux measurements. The first subsystem comprises two parallel plane ionization chambers. The first chamber covers the size of the full swept beam. The external high-voltage planes are preferably made of thin Mylar foils, approximately 25 microns, coated with aluminum. The signal plane in the middle of the chamber is generally open to air and operates at about 2 kV. The gap between the signal and high voltage foils is approximately 5 mm on each side of the signal plane, allowing for a fast collection time of less than 100 microseconds. The second chamber is a similar ionization chamber with a larger gap, i.e. 1 cm, and a lower electric field, i.e. 2 kV of applied voltage. The reaction time of the second monitor is slower. The second subsystem comprises of a position sensitive monitor made of kapton foils coated with 4 mm wide aluminum strips. The ionization charge created in the gap of the chamber is collected on the different strips, providing the information on the position and shape of the antiproton beam.

In certain embodiments, This information is monitored continuously during treatment by reading the content of scalers at the end of each spot. Preferably, two strip planes are used, one for the direction perpendicular to the sweeper displacement and the other parallel to it. It should be further noted that other methods and systems can be used to monitor the beam. For example, measuring antiproton delivery rates can be achieved by calculating the difference between how many antiprotons are left in a storage device, cooling ring, or other source after a pulse of antiprotons has been delivered to the synchrotron relative to how many antiprotons were present in the source prior to the pulse.

Once the target number of antiprotons has been reached, the beam is switched off using a fast kicker-magnet (not shown) located in the beam line ahead of the gantry head 1115. In one embodiment, the fast kicker magnet is a 20 cm long, laminated C-magnet with a 5 cm pole gap, and the vacuum chamber is an elliptical pipe comprised of a material capable of enabling the generation and maintenance of a sufficiently high vacuum level. The lamination of the magnet and the material of the beam pipe are chosen to avoid eddy current effects during switching of the kicker magnet. In one embodiment, Ferrite Philips 8C11 may be used for the yoke of the kicker magnet to minimize eddy currents and aid compatibility with the ultra-high vacuum environment. The kicker magnet is operated at 50 amps to deflect the beam in the vertical direction. With this device, the beam can be switched on and off in less than 50 microseconds.

The depth of the dose deposition is measured by a range shifter system 1145. The range shifter is placed in the nozzle, behind the monitoring system, and, in one embodiment, consists of 40 degrader plates, which cover the full swept beam. Pneumatic valves can be used to move individual plates into the beam path. The mechanical movement of the beam takes approximately 30 ms per plate. Using a single command, removing all plates from the beam path can occur in approximately 200 ms. Of the 40 plates, 36 are made of polyethylene and have a thickness equal to an antiproton range of 4.7 mm in water. One plate has only half that thickness to allow for a more precise depth scanning at low energy. Three plates are made of thin lead foil and can be used to enlarge the spot size, if desired. The projected dead time contribution from the range shifter system is 35-40 seconds, 30 seconds to move plates into the beam path and 5-10 seconds to remove the full stack. Additional devices can be used to contour the beam, including specially designed metal alloys. These devices may be used at the outlet of the nozzle (not shown) and can conform the beam to the cross-sectional size and shape of the target area within the patient.

In some embodiments, a beam is formed and delivered without the use of degraders or other devices to physically contour the beam. The inclusion of barriers, structures, or other materials within the beam line can cause the unwanted generation of particles, such as pions, neutrons and gamma rays, that will dose the patient without any beneficial medical purpose. To vary dosage levels, it can be preferred, depending on the embodiment, to use a variable energy synchrotron whose energy level can be modified as needed to deliver antiprotons to the requisite depth.

Figure 9:
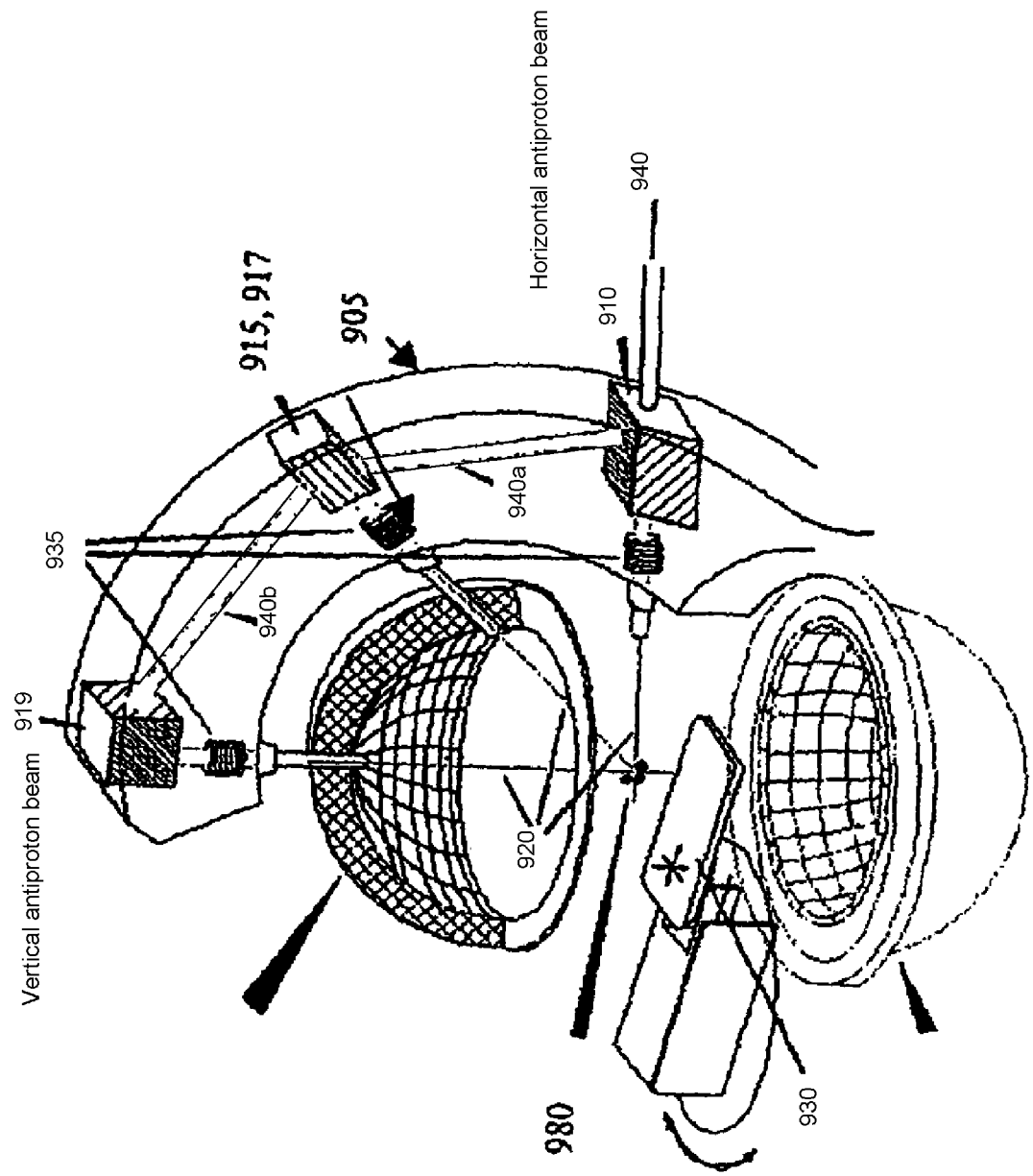
FIG. 9 is a diagram illustrating an example antiproton delivery device configured in accordance with another embodiment.

In another embodiment, shown in FIG. 9, a delivery pipe 940 is directed through a series of magnets 919, 915, 917, 910 and positioned relative to a patient table 930. The delivery pipe 940 bends as it extends out from an accelerator (not shown), through a shielded support structure 905, and into the plurality of delivery heads 935 through the application of magnets 919, 910, 917, 915. Operationally, the fixed delivery mechanism can deliver an antiproton beam 920 from multiple directions without requiring a rotatable gantry. The present embodiment can therefore direct multiple antiproton beams 920 to target a single isocenter without requiring the more complex gantry structure. While the present embodiment is shown having three delivery points from which fixed beams 920 are emitted in the direction of the patient table 930, one of ordinary skill in the art will appreciate that, using the appropriate number and type of bending magnets, the beam line can be designed to deliver any number of fixed beam configurations directed toward the patient table.

More specifically, in the illustrated embodiment, the antiproton beam (not shown) enters into the structure 905 via the vacuum pipe 940. The vacuum pipe extends through one 135 degree bending magnet 910, present in line with the delivery pipe 940, and into a nozzle head 935. When activated by a control system (not shown), the bending magnet 910 operates to redirect the antiproton beam into a second vacuum pipe section 940a, into a first 90 degree bending magnet 915, and through a second nozzle head 935, if the 90 degree bending magnet 915 is activated by a control system (not shown). If the 90 degree bending magnet 915 is unactivated, a first 45 degree bending magnet 917 is activated to redirect the antiproton beam into and through a third vacuum pipe section 940b, into a second 135 degree bending magnet 919, and through a third nozzle head 935. The first 45 degree bending magnet 917 and first 90 degree bending magnet 915 are shown in FIG. 9 as being co-located in the same area. Preferably the support structure 905 is designed to provide maximum rigidity to the beam line. The weight of the entire gantry is generally dominated by the bending magnets 919, 910, 915, 917 and appropriate balancing weights should be provided in the structure 905 to insure the gantry does not fall, tip, or otherwise become unstable.

Operationally, the antiproton beam is deposited in the patient preferably as a sequence of sequential pulses, directed from one, or a combination of several, delivery points defined by nozzles 935. For example, in operation, the 135 degree bending magnet 910 can be inactivated by a control system (not shown) to allow an antiproton beam to travel into and through a nozzle head 935 having a monitor and range shifter system (not shown), and into the patient (not shown). Where a second beam impingement path is desired, e.g. through a second delivery point, the 135 degree bending magnet 910 can be activated by a control system (not shown) to allow an antiproton beam to be redirected into the first 90 degree bending magnet and, if activated, through a nozzle head 935 having a monitor and range shifter system (not shown) and into the patient (not shown). Where a third beam impingement path is desired, the first 45 degree bending magnet 917 can be activated by a control system (not shown) to allow an antiproton beam to be redirected into the second 135 degree bending magnet and, if activated, through a nozzle head 935 having a monitor and range shifter system (not shown) and into the patient (not shown). A beam impingement path is the pathway through the patient that is traveled by an antiproton beam to reach a target region.

As previously discussed, the number of antiprotons delivered in a single, directed application is preferably measured by a beam monitor system positioned in the nozzle 935. In one embodiment, the beam monitoring system comprises two monitoring subsystems providing two independent beam flux measurements. The two monitoring subsystems are substantially similar to those described in relation to the gantry configuration. Similarly, other methods and systems can be used to monitor the beam. Once the target number of antiprotons has been delivered into a patient through a delivery point, the beam is switched off preferably using a fast kicker-magnet (not shown) located in the beam line 940. The fast kicker magnet and associated support structures are substantially similar to those described in relation to the gantry configuration.

While a range shifter system and other additional devices can be used to control and contour the beam, as discussed in relation to the gantry configuration, in certain embodiments a beam is formed and delivered without the use of degraders or other devices to physically contour the beam. The inclusion of barriers, structures, or other materials within the beam line can cause the unwanted generation of particles, such as pions, neutrons and gamma rays, that will dose the patient without any beneficial medical purpose. To vary dosage levels, it is preferred to use a variable energy synchrotron whose energy level can be modified as needed to deliver antiprotons to the requisite depth.

In both the gantry and fixed beam configurations, the patient table can be fixed or moveable. Where moveable, the patient table can be moved linearly along all three coordinate planes, x, y, and z, and rotationally across one or more coordinate planes, as needed. In one example embodiment, the patient table comprises an elongated rectangular bedding, preferably of sufficient firmness to maintain the patient on an even plane surface, that is affixed to a table frame that preferably has at least four legs connected, at their bases, to wheels. The frame is preferably a metallic structure capable of being tilted to modify the planar position of the bedding without requiring the concurrent repositioning of the patient. One of ordinary skill in the art will appreciate that numerous table designs can be with in various embodiments, including the one described by U.S. Pat. No. 6,152,599 incorporated herein by reference, without departing from the scope of the invention.

As further discussed below, a plurality of variables are monitored and modified to insure that the proper dosage is being delivered to the proper area within the patient. The position and quantity of each dose is determined by the application of an antiproton treatment protocol and cancer diagnostic procedure pursuant to one example embodiment. Through the diagnosis and protocol procedures, dose distributions of various shapes, from uniform to complex, can be constructed and delivered by modifying the beam impingement path and location on the patient, the number of antiprotons delivered, and the energy of the antiprotons. The antiproton beam, as delivered, is rapidly focused on the target area using magnetic fields in the form of a highly directed pencil beam positioned in three-dimensional space to insure the dose distribution substantially matches the distribution determined theoretically by Bragg Peak calculations.

In one embodiment, the gantry head can be rotated circumferentially relative to the patient to allow for the radial movement of the nozzle around the patient. The radial movement preferably covers a 180 degree arc above the patient table.

Additionally, the patient table can preferably be rotated, both vertically and horizontally, to establish an appropriate beam delivery angle relative to the gantry head. In operation, singular doses can be delivered, through specific tissue pathways, and then terminated. If necessary, the gantry head and/or patient table can then be moved to position the patient for a subsequent exposure to an antiproton beam via a different tissue pathway. The patient table is preferably not repeatedly rotated in the course of a treatment to reposition a patient in order to avoid creating discomfort to the patient and because such table adjustments often use far greater time and technician assistance.

Where a target volume is being treated for which multiple doses delivered adjacent to one another may be needed it is preferred to use a sweeper magnet to move the beam, thereby speeding up adjustment time and obtaining greater precision relative to mechanical reconfigurations. One example sweeper magnet is a 40 cm long H-type laminated magnet with a 5 cm pole gap having a vacuum pipe made of insulator material to avoid eddy effects. Using this type of sweeper effect, the beam spot can be moved by about 10 cm. The current in the coils can be chosen at any desired value, preferably in the range of +/−500 amps, which corresponds to a magnetic field range of +/−0.8 Tesla. The sweeper magnet is used to perform the most frequent displacements of the antiproton beam. For adjacent irradiations requiring only a small change of current in the sweeper magnet, the time required to switch the beam off and adjust position should be below about 5 ms. For example, where a treatment requires 10,000 adjacent spots delivered to a single target area, total dead time may be limited to under one minute.

In another embodiment, the dose distributions of various shapes, from uniform to complex, can be constructed and delivered by transmitting a beam of antiprotons from a plurality of different delivery points fixed in space. Referring back to FIG. 9, a single isocenter 980, for example a tumor located in the brain of a patient, can be targeted via three different beam pathways using the three delivery points. Additionally, the patient table can be rotated, both vertically and horizontally, to establish an appropriate beam delivery angle relative to the delivery points. In operation, singular doses can be delivered, through specific tissue pathways, and then terminated. The patient table is preferably not repeatedly rotated in the course of a treatment.

In certain antiproton device configurations, an operator workstation comprising a data processor, data storage device, and display is in data communication with the delivery synchrotron, magnets, and delivery structures, such as the motorized drive gears attached to the gantry head and/or to the base of the patient table. The workstation is programmed to implement the antiproton treatment protocol developed for the patient. An operator initiates the workstation and indicates, through an interface, that the patent is positioned in an initial reference position. By positioning the patient in an initial reference position, the workstation can be informed as to where the patient sits in space and, therefore, move the gantry head and/or patient table into the proper position relative to the patient, for delivering the antiproton beam. Several methods may be used for positioning, including, but not limited to those which follow. The initial reference position can be established, for example, by placing the patient in a specific position relative to the table utilizing spine implanted radioopaque fiducials which may be implanted in the patient's spinal column permitting accurate repositioning of the patient to +/−1.7 mm. The initial reference position can also be established by placing the patient in a specific position relative to the patient table or by covering the patient with a sheet comprised of a grid of electronic contacts, each of said contacts being placed in a specific position relative to the patient's body. More specifically, in one embodiment, the grid of electronic contacts is interconnected by a conductive material and culminates in a single wire contact extending into a grid reader. The grid reader sends a signal into and through the contacts, receives responses from the contacts, reconstructs the grid structure in space, and transmits the grid configuration to the workstation. Operating on assumptions as to how that grid structure is positioned relative to the patient's body, the workstation can identify specific points on the patient's body.

Beginning with the patient in an initial reference position, the workstation transmits a signal to the motorized drive gears of the gantry head and/or patient table informing the drive gears to move the gantry head and/or patient table into a specific position based upon the angle and path by which an initial antiproton dose will be delivered into the patient. Where a fixed beam line configuration is being used, only the patient table is manipulated to achieve a specific position based upon the angle and path by which an initial antiproton dose will be delivered into the patient.

With the patient position positioned, the workstation transmits a signal to the beam monitor system informing it what amount of antiprotons are to be delivered and also transmits a signal to the range shifter system informing it of the dosage depth prior to activating the delivery synchrotron to accelerate (or decelerate) and deliver antiprotons of the desired energy level to the system. In one embodiment, the delivery system is activated and antiprotons are delivered to an appropriate depth and in an appropriate number, as measured and monitored by the range shifter and beam monitoring systems respectively. Preferably a plurality of procedures is used in parallel to monitor the quantity and depth of dose delivery. For example, a first procedure can comprise the workstation actively communicating scanning parameters to the ranger shifter and beam monitoring systems. Concurrently, a second procedure can be implemented in which the workstation passively monitors the activities of the ranger shifter and beam monitoring systems. Passive monitoring can be achieved by detecting the number and location of antiproton annihilations within the patient, as further discussed below, and deriving the associated energy level and number of antiprotons delivered. The data generated from the second procedure can be compared to the parameters of the first procedure to cross check the accuracy of the monitoring and shut down systems. If a discrepancy is identified, an automatic shutdown procedure can be effectuated, where the antiproton source is turned off, the fast kicker magnet is activated, and/or a solid beam shutter is deployed.

In another embodiment, the workstation transmits a signal to the beam monitoring system informing it what amount of antiprotons are to be delivered and also transmits a signal to the delivery synchrotron to accelerate and deliver antiprotons at a specific, predefined energy level, thereby eliminating the need for degraders, range-shifters or other such mechanism that may generate unwanted particles, such as pions, neutrons and gamma rays. In one embodiment, the delivery system is activated and antiprotons are delivered to an appropriate depth and in an appropriate number, as measured and monitored by the beam monitoring system. Similar parallel procedures as discussed above can be used to monitor the quantity and depth of dose delivery.

After the initial antiproton irradiation is completed, the parameters for the position of beam scan can be modified to enable the irradiation of an entire target area. Beam repositioning can be performed with the beam switched off. As previously discussed, beam repositioning can be effectuated by gantry head movement, table movement, or the use of a deflecting magnet (such as a sweeper magnet), depending on the antiproton delivery device being used.

In a gantry configuration, to insure beam focus on the designated target area, referred to as the isocenter, the shape of the poles of the 90 degrees bending magnet and of the sweeper magnet can be designed to produce a displacement of the swept beam which is substantially exactly parallel to its direction and to maintain the focusing of the beam at the isocentric plane independently of the setting of the sweeper magnet. The shape of the scanned beam can be sweeper invariant. The precision of the beam is measured at better than 1 mm for beam parallelism during scanning (independent of sweeper position), change of beam shape during scanning (independent of sweeper position), isocenter stability (independent of gantry angle), and beam position reproducibility after a change of the beam energy.

In addition to the above controls, for both the fixed beam and gantry configurations, certain embodiments additionally comprise a plurality of backup controls to shut down or otherwise block the undesired antiproton irradiation of a patient. Antiproton beams are automatically controlled by a fast kicker magnet. In case the kicker magnet fails to activate, another form of beam shut down should be immediately deployed, such as the switching off of the antiproton accelerator. Alternatively or in combination, a mechanical beam shutter can be used to block the patient from antiproton exposure.

Figure 10A:
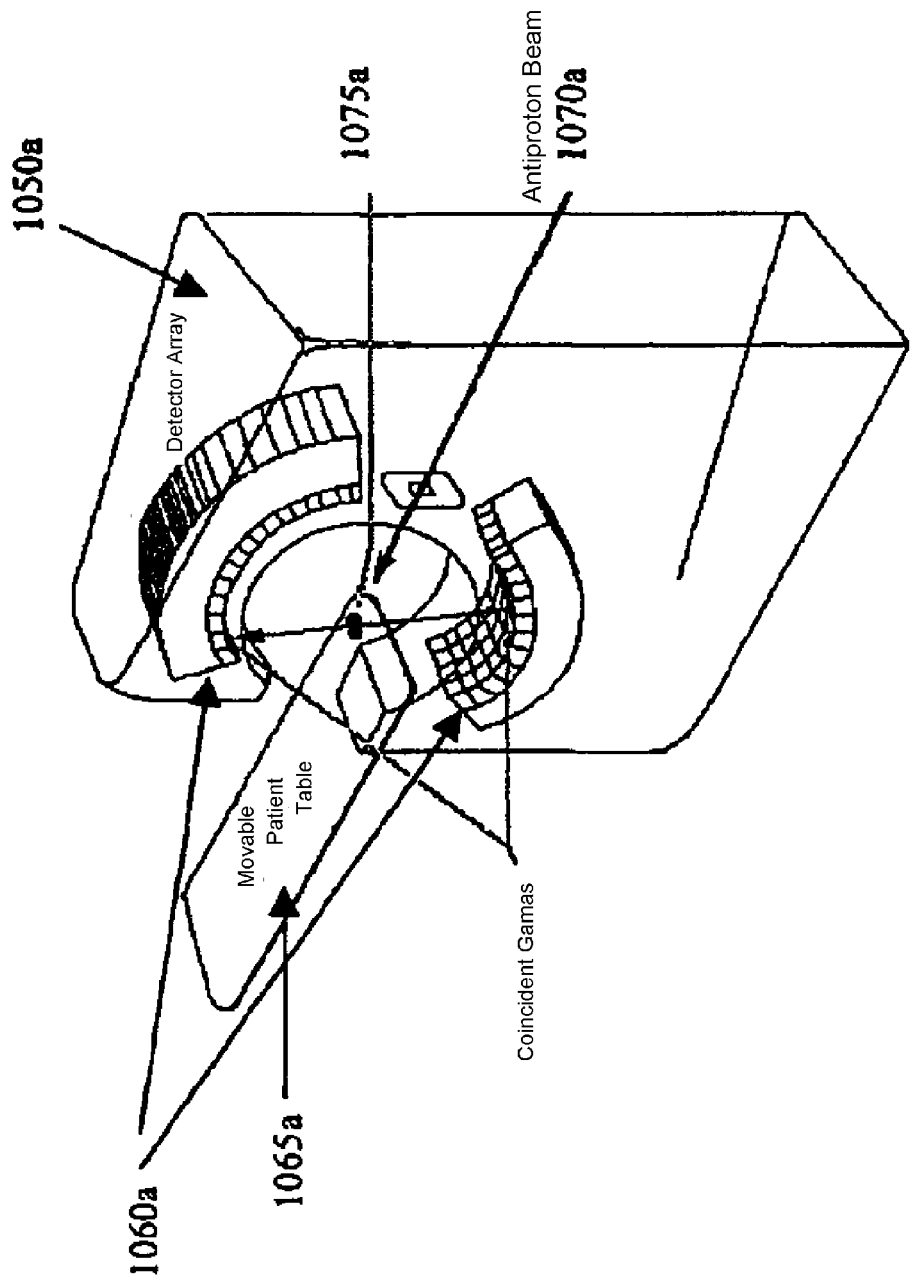
FIG. 10a is a diagram illustrating an example antiproton delivery device combined with a detector array in accordance with another embodiment.

In one example embodiment of the antiproton gantry device, shown in FIG. 10a, the gantry 1050a is combined with a plurality of detectors 1060a that enable the imaging of certain patient tissue areas subjected to antiproton radiation. A patient (not shown) is positioned on a patient table 1065a. Antiproton beam 1070a enters gantry 1050a and is directed toward a target volume 1075a. As previously discussed, a plurality of different configurations can be used to direct beam 1070a toward volume 1075a, and the configuration shown in FIG. 10a is merely an exemplary embodiment. The detectors 1060a are arrayed in a configuration that avoids obstructing beam 1070a while concurrently exposing the detector array 1060a to antiproton annihilation emissions that can be used to conduct real-time imaging, as further discussed below.

Similarly, in another example embodiment of the fixed beam device, shown in FIG. 10b, the fixed beam system 1050b can be combined with a plurality of detectors 1060b, 1062b that enable the imaging of certain patient tissue areas subjected to antiproton radiation. A patient (not shown) is positioned on a rotatable patient table 1065b. An antiproton beam line (not shown) enters gantry 1050b and is directed by action of a plurality of beam magnets toward a target volume 1075b. As previously discussed, a plurality of different configurations 1070b can be used to direct an incoming beam toward volume 1075b, and the configuration shown in FIG. 10b is merely an exemplary embodiment. The detectors 1060b, 1062b are arrayed in a substantially spherical upper detector configuration 1060b and substantially spherical lower detector configuration 1062b that avoids obstructing the plurality of beams 1070b while concurrently exposing the detector array 1060b, 1062b to antiproton annihilation emissions that can be used to conduct real-time imaging, as further discussed below.

The detectors can be made of a high atomic number, high-density material capable of interacting with gamma rays to create an electromagnetic shower. The shower energy is substantially contained inside a volume, each having a radius of two times the Moliere radius and having a length of approximately 20 $X_0$ radiation lengths. In one embodiment, the detector assembly is supported by a carriage, which can be rotated around the target axis running on a bent, nearly semi-circular track. The detector may also be moved radially by a screw arrangement to a specified range of distance from the target to the crystal face.

In specialized high-energy physics experimentation, energetic charged particles and gamma rays, which are produced when an antiproton annihilates at rest on a proton and which then move radially away from that annihilation site, are detected and tracked back to a common point, referred to as the vertex. The process of tracking the energetic charged particles and gamma rays back to their common point of origination is referred to as vertex reconstruction. To effectively perform vertex reconstruction, the detectors used can be designed to detect particles and/or radiation that have the highest likelihood of escaping a patient's body with the least amount of scattering or other perturbations that can complicate determinations of where the particle and/or radiation had originated.

Assuming an antiproton beam penetrates and stops at the center of a sphere of water having a 15 centimeter (cm) radius and annihilates, only those particles having energy greater than given by the stopping range of 15 cm of water will escape the sphere and be capable of being detected. Relative to charged kaons, neutral kaons (short), and neutral kaons (long), muons and charged pions have the highest probability of escaping the 15 cm sphere. Neutral pions decay in less than 0.025 microns from the point of annihilation into a pair of gamma rays that escape with energy carried by the pion.

Charged pions escaping material undergo substantial amounts of scattering, thereby increasing the complexity of vertex reconstruction. When being emitted out of 15 cm of water, charged pions having momenta less than about 160 MeV/c stop in the water and are not detected, while charged pions having momenta in excess of about 150 MeV/c scatter laterally, relative to the direction of the linearly formed track, by a root mean square of approximately 7 millimeters. The change of direction is dependent upon the particle's momentum, the particle's charge, and the material through which the particle is passing.

Although lateral displacement improves as particle momentum increases, even at the higher momenta, pion lateral scattering is at or around 1.5 mm, thereby limiting imaging precision to plus or minus 1.5 mm. This limitation decreases as the site of annihilation approaches the surface.

In one example embodiment, vertex reconstruction is performed using neutral pion decay gamma radiation. Unlike charged pions, gamma rays have a high probability of escaping a material body without undergoing substantial interactions which cause scattering and skew vertex reconstruction calculations. Further, the pair of gamma rays emitted can be traced back to the point where the neutral pion decayed and, because neutral pions decay within 0.025 microns of the annihilation point, can provide a more accurate representation of where the annihilation occurred. In a typical annihilation event, the mean number of gammas emitted for each antiproton annihilation event is four (two for each neutral pion), and can be as high as 10.

Operationally, vertex reconstruction is performed by relying on the detection of multiple points along the shower axis and the use of those multiple points to generate a vector localizing a common origination area. It can be preferred that any heavy inorganic scintillators used to detect gamma rays have one or more of certain desired characteristics, including, high stopping power to maximize the probability of complete absorption of the incident energy, high timing resolution, high energy resolution, minimum dead time, wavelengths of emission that match with the spectral response of the photodetectors, mechanical ruggedness, radiation hardness, chemical stability in normal atmospheric conditions, and reasonable cost. Existing heavy scintillators meet certain of these criteria, including high luminous efficiency measured in photons/MeV (NaI(TI) and CsI(TI)), high density/high atomic number (BGO), short Moliere radius (BGO and $CeF_3$), high initial photon intensity measured in photons/MeV/ns with high timing resolution ($BaF_2$), and high luminous efficiency and wavelength suitable for silicon photodiodes (CsI(TI) and $CdWO_4$). Proper selection of a detector provides for a further benefit of gamma ray shower detection over charged particle detection is speed. Shower detection can be done using a fast scintillator, less than 15 nanoseconds, thereby allowing a faster response than charged particle tracking.

Tungsten (W), sodium iodide doped with thallium (NaI (TI)), and lead tungstate ($PbWO_4$) are three materials that can be used for shower detection. Sodium iodide activated by thallium is a well-known material used for scintillation applications. NaI(TI) has a high luminescence efficiency and spectroscopic performance with minimal significant self absorption of the scintillated light. Lead tungstate is a highly efficient and fast scintillator with one of the shortest radiation lengths and Moliere radii among the known scintillators, satisfactory light yield for this energy range, and high radiation stability. Radiation lengths for NaI(TI), CsI(Ti), $PbWO_4$, BGO, Tungsten (W), and Iridium (Ir) are 2.59 cm, 1.86 cm, 0.89 cm, 1.12 cm, 0.323 cm, and 0.27 cm, respectively. The Moliere Radius for NaI(TI), $PbWO_4$, and W are 4.5 cm, 2.2 cm, and 0.8 cm respectively. The density for NaI(TI), CsI(TI), $PbWO_4$, BGO, Tungsten (W), and Iridium (Ir) are 3.67, 4.53, 8.28, 7.13, 19.4, and 22.4, respectively. The decay time for NaI(TI) is 250 ns while for $PbWO_4$ it is between 5 and 15 ns. For BGO and CsI(TI), the decay times are 300 ns and 0.9/7.0 μS. The light output for NaI(TI), CsI(TI), $PbWO_4$, and BGO are 1.0, 0.85, 0.01, and 0.15, respectively. Another material usable for the present application includes uranium, which has the requisite Moliere radius and material density. However, because it is not actively sensitive to the shower, it will have to be combined with an active scintillator. Using layers of tungsten, for example, in combination with uranium can provide a satisfactory detector device.

When using tungsten, one can employ the sensing element in a matrix, such as a 3.23×3.23×3.23 $mm^3$ matrix, or in a crossed 3.23×3.23×200 $mm^3$ hodoscope plastic scintillator to sample the shower's charged particles passing between sandwich plates. Locating the vertex with a precision on the order of 500 microns is possible using these techniques. When using lead tungstate, one can use a 9×9×9 $mm^3$ matrix or a crossed 9×9×200 $mm^3$ hodoscope sensor array. The radiation length of lead tungstate is 2.7 times greater than tungsten. Although the chosen approach is dependent upon a plurality of technical, as well as economic considerations, one consideration favoring the smaller shower localization of tungsten over lead tungstate is its ability to separate the gamma pair of the neutral pion decay. As the momenta of neutral pions increase, lead tungstate loses efficiency at separating decay gammas relative to a tungsten shower detector.

The detectors can be surrounded by a shielding structure to isolate the detectors from the surrounding environment. In one implementation, NaI(TI) crystals are surrounded by an active plastic shield, a passive LiH shield, and a low activity thick lead shield which, in combination, have a cosmic rejection efficiency around 98%. Further, the detectors can be supported by a carriage structure to enable efficient rotation around a target axis.

Referring to FIGS. 10c through 10r, a plurality of detector configurations is shown particular to each calorimeter imager material used. Imagers for NaI and BGO are not shown because NaI is similar to CsI and BGO is similar to $PbWO_4$. FIGS. 10c and 10d show example detector configurations for brain imaging using $PbWO_4$ as the calorimeter imager material. In FIGS. 10c and 10d, a beam pipe 1083d delivers an antiproton beam to a predesignated area within the patient's brain 1085d. The beam direction and imager 1086d are fixed relative to each other. The patient is positioned on a table 1084d. In use, a patient will first be positioned between detector elements, as shown in FIGS. 10a and 10b, and then the elements are assembled into a portion of a spherical shell sharing the center with the annihilation region, appropriately accounting for straggling and multiple straggling limits. Sufficient resolution can be achieved by having the calorimeter elements point approximately to the annihilation site. When annihilation occurs, a plurality of gamma rays 1087d are emitted, due to the decay of neutral pions generated in the course of the annihilation, which extend from the target region 1085d with an opening angle of approximately 30 degrees taken from the point of annihilation. The gamma radiation may have an opening angle less than 30 degrees, but not more than 30 degrees relative to each other. In one embodiment, the imager length (20 radiation lengths) is 17.8 cm. The inner radius size is 0.89 cm×0.89 cm with the outer radius size being 1.8 cm×1.8 cm. The maximum mass is approximately 1556 kg.

FIGS. 10g and 10h, 10k and 10l, and 10o and 10p show a similar detector configuration using CsI(TI), Ir, and W as calorimeter elements, respectively. A beam pipe 1083h, 1083l, 1083p delivers an antiproton beam to a predesignated area within the patient's brain 1085h, 1085l, 1085p. The beam direction and imager 1086h, 1086l, 1086p are fixed relative to each other at least during detection. The patient is positioned on a table 1084h, 1084l, 1084p. In use, a patient will first be positioned between detector elements, as shown in FIGS. 10a and 10b, and then the elements assembled into a portion of a spherical shell sharing the center with the annihilation region, appropriately accounting for straggling and multiple straggling limits. Sufficient resolution can be achieved by having the calorimeter elements point approximately to the annihilation site. When annihilation occurs, a plurality of gamma rays 1087h, 1087l, 1087p are emitted, due to the decay of neutral pions generated in the course of the annihilation, which extend from the target region 1085h, 1085l, 1085p with an opening angle of approximately 30 degrees taken from the point of annihilation. The gamma radiation may have an opening angle less than 30 degrees, but not more than 30 degrees relative to each other. In one embodiment, or CsI(TI), the imager length (20 radiation lengths) is 37.2 cm, the inner radius size is 1.86 cm×1.86 cm, the outer radius size is 5.7 cm×5.7 cm and the maximum mass is approximately 3172 kg; for Ir, the imager length (20 radiation lengths) is 10.8 cm, the inner radius size is 2.7 cm×2.7 cm, and the maximum mass is approximately 1073 kg; for W, the imager length (20 radiation lengths) is 12.92 cm, the inner radius size is 0.32 cm×0.32 cm, the outer radius size is 5.7 cm×5.7 cm, and the maximum mass is approximately 1137 kg; and for BGO (not shown), the imager length (20 radiation lengths) is 22.4 cm and the inner radius size is 1.12 cm×1.12 cm. For non scintillators, such as Ir and W, preferably approximately 50% of the space in the length is dedicated to a plastic scintillator read out of the shower in a hodoscope's geometry.

FIGS. 10e and 10f show detector configurations for torso imaging using $PbWO_4$ as the calorimeter imager material. A beam pipe 1083f delivers an antiproton beam to a predesignated area within the patient's torso 1085f. The beam direction and imager 1086f can be fixed relative to each other. The patient is positioned on a table 1084f. As previously stated, in use, a patient will first be positioned between detector elements, as shown in FIGS. 10a and 10b, and then the elements are assembled into a portion of a spherical shell sharing the center with the annihilation region, appropriately accounting for straggling and multiple straggling limits. Sufficient resolution may be achieved when the calorimeter elements point approximately to the annihilation site. When annihilation occurs, a plurality of gamma rays 1087f are emitted, due to the decay of neutral pions generated in the course of the annihilation, which extend from the target region 1085f with an opening angle of approximately 30 degrees taken from the point of annihilation. The gamma radiation may have an opening angle less than 30 degrees, but not more than 30 degrees relative to each other. In one embodiment, the imager length (20 radiation lengths) is 17.8 cm, the inner radius size is 0.89 cm×0.89 cm, the outer radius size is 1.8 cm×1.8 cm, and the maximum mass is approximately 3618 kg.

FIGS. 10i and 10j, 10m and 10n, and 10q and 10r show a similar detector configuration using CsI(TI), Ir, and W as calorimeter elements, respectively. A beam pipe 1083j, 1083n, 1083r delivers an antiproton beam to a predesignated area within the patient's torso 1085j, 1085n, 1085r. The beam direction and imager 1086j, 1086n, 1086r are fixed relative to each other. The patient is positioned on a table 1084j, 1084n, 1084r. In use, a patient will first be positioned between detector elements, as shown in FIGS. 10a and 10b, and then the elements are assembled into a portion of a spherical shell sharing the center with the annihilation region, appropriately accounting for straggling and multiple straggling limits. Sufficient resolution may be achieved when the calorimeter elements point approximately to the annihilation site. When annihilation occurs, a plurality of gamma rays 1087j, 1087n, 1087r are emitted, due to the decay of neutral pions generated in the course of the annihilation, which extend from the target region 1085j, 1085n, 1085r with an opening angle of approximately 30 degrees taken from the point of annihilation. The gamma radiation may have an opening angle less than 30 degrees, but not more than 30 degrees relative to each other. In one embodiment for CsI(TI), the imager length (20 radiation lengths) is 37.2 cm, the inner radius size is 1.86 cm×1.86 cm, the outer radius size is 3.8 cm×3.8 cm and the maximum mass is approximately 6328 kg; for Ir, the imager length (20 radiation lengths) is 10.8 cm, the inner radius size is 2.7 cm×2.7 cm, and the maximum mass is approximately 2500 kg; for W, the imager length (20 radiation lengths) is 12.92 cm, the inner radius size is 0.32 cm×0.32 cm, and the maximum mass is approximately 2618 kg. For non scintillators, such as Ir and W, approximately 50% of the space in the length is dedicated to a plastic scintillator read out of the shower in a hodoscope's geometry.

With respect to performance, the angular acceptance achieved in the crystal barrel spectrometer is approximately 6 degrees (100 mrad). Without adjacent cell interpolation, the calorimeter imager materials, operating in the aforementioned brain imager and torso imager configurations, have the following degrees of angular acceptance: for brain imager configurations, the angular acceptance of CsI(TI), $PbWO_4$, BGO, W, and Ir is 103 mrad, 49 mrad, 62 mrad, 18 mrad, and 15 mrad respectively. For torso imager configurations, the angular acceptance of CsI(TI), $PbWO_4$, BGO, W, and Ir is 53 mrad, 25 mrad, 32 mrad, 9.2 mrad, and 7.2 mrad respectively. If interpolation is implemented, a 300% gain in resolution may be achieved for certain calorimeter imager materials operating in certain configurations, upwards of a 1000% gain in resolution for materials such as $PbWO_4$. The highest angular resolution can be achieved with W or Ir, although Ir may be expensive to use.

3. Diagnosis and Treatment Strategy

Cancer is diagnosed using a variety of methods, a few of which are discussed herein. A patient suspected to have cancer maybe imaged using x-ray, CT, MRI, radioactively labeled tracer uptake, thermography, ultra sound and PET scanning. A medical practitioner skilled in the art of cancer diagnosis will understand how to use these technologies to yield an image that can indicate the presence of an unusual mass, and possibly, cancer.

In one example embodiment, a patient is treated in a medical facility in which antiproton radiation therapy can be delivered. A schematic plan layout of an exemplary medical facility is provided in FIG. 11. The exemplary medical facility 1100 comprises a plurality of areas dedicated to standard medical facility functions, including examination rooms, maintenance areas, reception areas, waiting rooms, janitorial rooms, utilities, staircases 1187, elevators 1180, a lobby 1190, and staff areas, such as staff offices, meeting rooms, lunch areas, patient record keeping. Sizeable rooms internal to the facility 1185 are used for staff offices and/or examination rooms, rooms adjacent to the treatment area 1160 are used for patient preparation and changing, larger rooms 1170 are used for meeting or waiting areas, the smaller rooms 1175 are used for utilities or janitorial purposes, and the other rooms 1165 are used for storing patient records, secretarial functions, lunch rooms, smaller staff offices, and at least one dosimetry room and health physics room.

The illustrated medical facility 1100 further comprises areas specialized for the delivery of antiproton therapy. A plurality of treatment rooms 1103 surrounded by heavy shielding 1135 is located in the back of the facility 1100. A control room 1130 is integrally provided with each treatment room 1103. In one room 1003 a MRI 1145 is provided proximate to a CT simulator 1155. In a set of second rooms 1103, a patient table 1120 is situated proximate to a delivery point 1115 integrally attached to a delivery device, such as a fixed beam or gantry device. Additionally, a treatment chair 1140 and an array of detectors (not shown) can also be situated proximate to the delivery point 1115 and patient table 1120. In a third room 1103, a calibration system 1125 is provided that enables an operator to calibrate the operation of the beam transport system 1105 and delivery synchrotron (not shown). Operationally, an antiproton beam is caused to travel through the beam transport system 1105 and bend by force of a plurality of bending magnets 1110, which are housed in a support structure.

Figure 11:
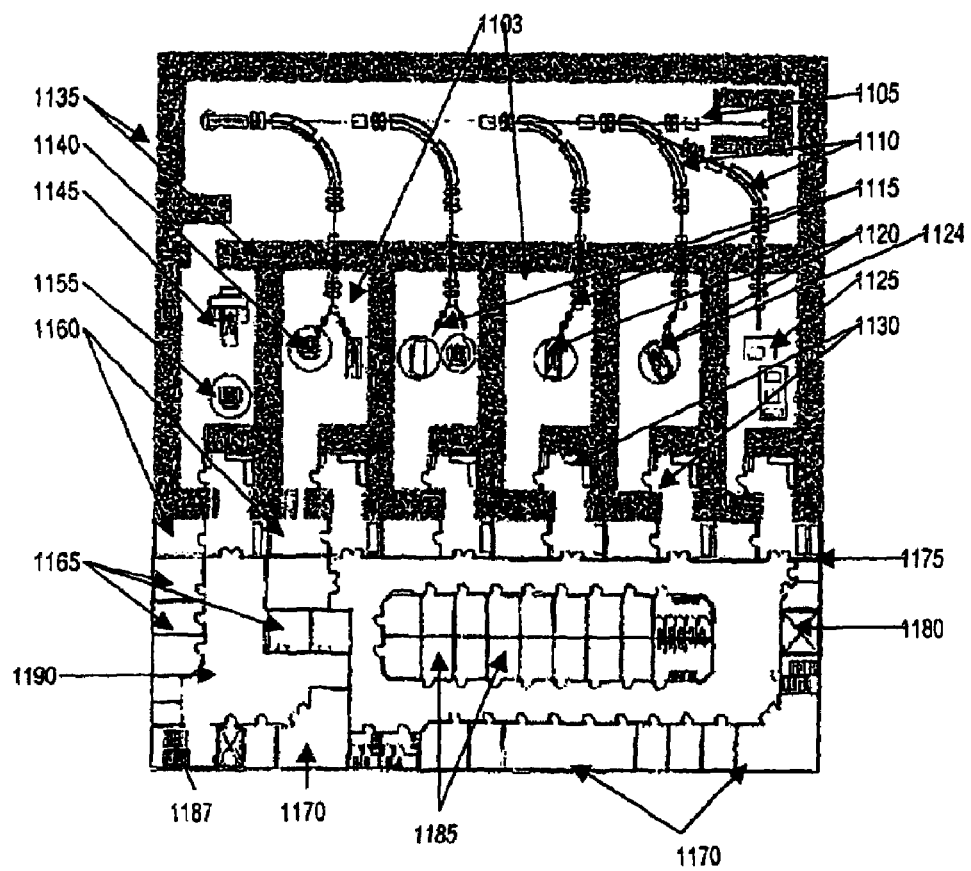
FIG. 11 is a diagram illustrating an example antiproton radiation medical facility configured in accordance with one embodiment.
Figure 11A:
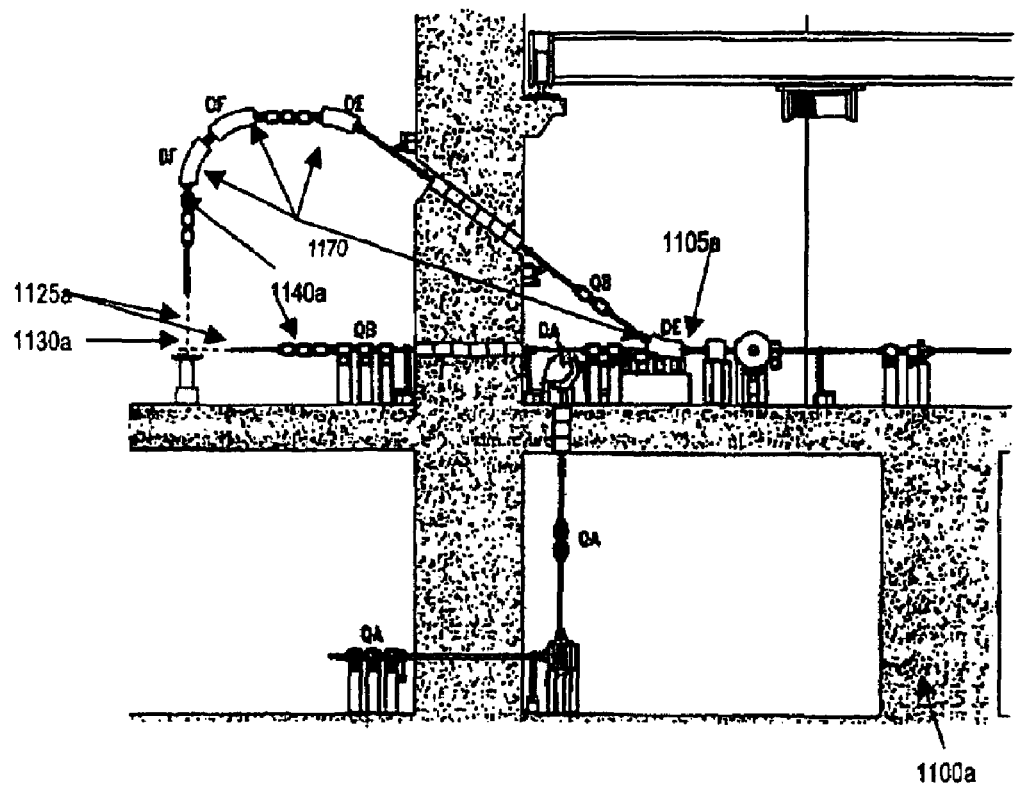
FIG. 11a is a schematic representation of a beam line integrated into the medical facility of FIG. 11.

Depending upon a centralized schedule of operation, one of the plurality of beam lines directed into specific treatment rooms 1103 will be active and delivering a predesignated dose of antiprotons to a patient 1124 positioned on a patent table 1120. Antiprotons traveling through the beam transport 1105 will be directed into the appropriate beam pipe that feeds a particular treatment room 1103. The beam pipe as shown terminates in a gantry or vertical/horizontal beamline. Referring to FIG. 11a, an exemplary beam line 1105a integrated with a medical facility 1100a is shown in the context of delivering an antiproton beam to a fixed beam antiproton delivery device. Two fixed beams 1125a are generated, focused on a target volume 1130a, by action of a plurality of bending magnets selectively bending antiprotons traveling through a beam pipe 1140a. A person familiar with high-energy physics will understand how to produce, collect, cool, decelerate and extract antiprotons through the application of vacuums pumps, magnets, radiofrequency cavities, high voltage instruments and electronic circuits. Antiprotons circulate inside vacuum pipes in order to avoid contact with matter with which they annihilate. The vacuum should be optimal, therefore several vacuum pumps, which extract air, are placed around the pipe. The magnets used include dipoles, which serve to change the direction of antiproton movement and insure they stay within the circular track, and quadrupoles, which are used as lenses or focusing magnets to insure that antiproton beam size is smaller than the vacuum pipe size. Electric fields are used to modify antiproton energy levels and are provided for by radiofrequency cavities that produce high voltages synchronized with the rotation of antiprotons around the ring. While the medical facility 1100, 1100a has been described in relation to a specific design and layout, one of ordinary skill in the art will appreciate that other space configurations can be used, depending upon the particular conditions of the location and the needs of the facility.

A patient is positioned in a diagnosis area that can have one of, or a combination of, several diagnostic devices. One diagnostic device can include a magnetic resonance imaging (MRI) scan in which a patient is subjected to an external, uniform magnetic field and radiofrequency energy that excites protons in the patient's body and subsequently produces signals with amplitudes dependent on relaxation characteristics and spin density. Abnormalities can be detected by identifying unusual signals that indicate a particular region has a different proton density than normally expected. Another diagnostic device that can reveal tissue structure and therefore identify unusual masses is computer tomography (CT) scanning. CT scans are performed by passing x-rays through a patient, at a large number of angles, by rotating the x-ray source around the patient. A plurality of detector arrays, located opposite the x-ray source, collect the transmission projection data in the form of various data points. The data points are synthesized into a tomographic image, or imaged slice, of a patient. The variation in transmission data is indicative of tissue density and can be used to identify unusual masses-in the body.

A third possible diagnostic device is a positron emission tomography (PET) scan in which the patient is administered, through an intravenous injection, a positron-emitting radioactive substance comprising a form of glucose that reacts with tissues in the body, in proportion to metabolic activity. By measuring the different amounts of positrons released by healthy and cancerous tissues, a computer creates an image reflective of the biological activity occurring within the patient. Because cells from many cancers have a higher affinity for certain positron-emitting radioactive substances, such as $F^{18}$ labeled glucose, the tumor area may be imaged. PET scans can be combined with x-ray based scans and MRI scans to confirm that an unusual structure may, in fact, be cancerous. More specifically, PET scans can be overlaid onto, or combined with, MRI or CT images to generate an integrated image that shows tissue structure associated with metabolic activity.

Output from one or more of the aforementioned diagnostic devices can be used by a medical practitioner, including technicians, nurses, radiologists, oncologists, and other medical professionals, to determine whether the patient has cancer and, if so, the location, extent, and stage of the cancer. In one example embodiment, shown in FIG. 12, at least one of the diagnostic scans from the PET scan 1305, MRI scan 1310, and/or CT scan 1315, is stored in an operator workstation 1320, transmitted to an antiproton treatment protocol station 1325, and used to assist in the development of an antiproton based treatment regimen. Alternatively, only the data representing key treatment parameters may be transmitted to the antiproton treatment protocol station.

Referring back to FIG. 11, the patient, once imaged, is taken to an antiproton treatment protocol station. The station can be co-located with the diagnostic machinery, placed in a separate office within the same building, or located in a completely separate facility. The schematic representation in FIG. 11 is provided for example purposes only.

Having identified and quantified the tumor location, a treatment protocol using antiproton radiation is developed. In one example approach, data representing the tumor size and location is transmitted from imaging technologies, as previously described, to an antiproton treatment protocol station. The treatment protocol station applies a set of analyses to determine the amount of antiprotons, antiproton energy sufficient for treatment, and preferred delivery pathways and communicates that protocol to an antiproton radiating and imaging station, as previously described. The antiproton treatment protocol station is in data communication with the imaging station used or, alternatively, is capable of receiving data stored on media, such as a disk or CD-ROM.

Figure 12:
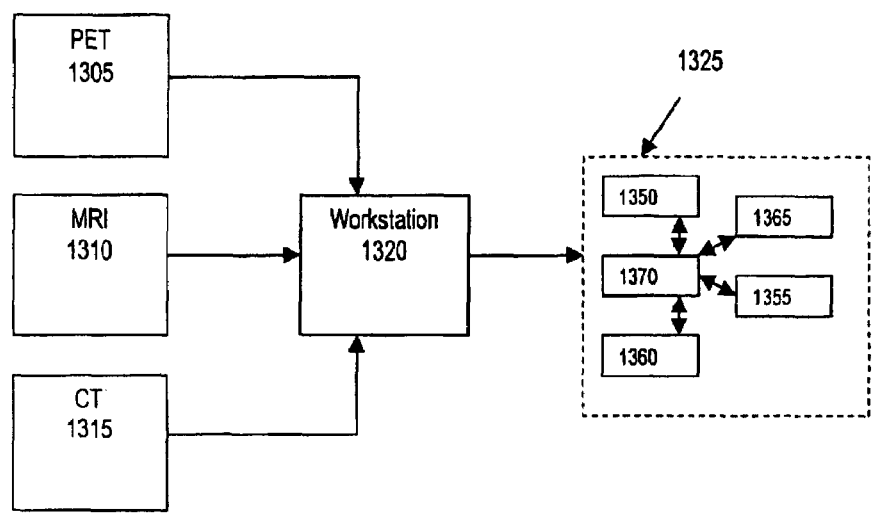
FIG. 12 is a diagram illustrating an example therapy station integrated with an antiproton treatment protocol station in accordance with one embodiment.

In one embodiment, shown FIG. 12, the treatment protocol station comprises a display 1350, print-out device 1355 storage device 1360, modem or network control card 1365, and processor 1370 capable of communicating with the display (any type of monitor), print out device (any type of printer), storage device, and modem/network controller and of implementing a plurality of instruction sets for determining the amount of antiprotons, antiproton energy sufficient for treatment, and preferred delivery pathways given a tumor size and location. The amount of antiproton radiation needed to terminate a mass is calculated, along with the amount of energy needed to deliver an antiproton to the mass depth. Using equations to determine the amount of energy deposited in collateral tissue and the residual energy plus annihilation event radiation effects, such as caused by the emission of particles like alpha particles, the energy deposited in the mass, along with the lateral spreads and Bragg Peak contours, can be determined. Once done, an energy deposition profile can be generated that covers the entire mass with sufficient antiproton induced radiation by summing multiple Bragg Peaks, assuming a plurality of spot scans performed at varying depths within the tumor region. The amount and energy level of antiprotons, for each location to be irradiated, defines the protocol, which is then sent to the antiproton radiation and imaging device, as previously discussed. During operation, a beam monitoring system and range shifter or a delivery synchrotron can be used to measure the actual dosage being delivered to insure it correlates with the desired calculated dosage. To the extent a range shifter is used, antiproton losses, caused by the degradation process, need to be calculated and incorporated into all beam monitoring calculations to insure accurate determination of actual antiprotons delivered to the patient.

As an example, a patient is diagnosed with a 1 cubic centimeter (cc) tumor located 10 centimeters below the skin surface. The diagnosis occurs through a combination of MRI and PET scans, which indicates a mass having a high metabolic rate in the patient's chest cavity. Using the location and tumor size data, the amount of antiprotons to be used to annihilate the target region is determined. One example method of determining the amount of antiprotons needed is by assuming the density of tissue to be around 1 gram per cc, assuming 500 rads will be sufficient to terminate the cancerous cells, and equating the relative biological effect (RBE) of antiproton radiation in the target volume to that of heavy ions having a 30 MeV recoil (RBE=5). This reflects the fact that at least one 30 MeV recoil heavy ion is produced for each antiproton annihilation event. Because 500 rads is approximately equivalent to $30 \times 10^9$ MeV per gram, the total number of antiprotons needed to deliver 500 rads is $10^9$. It should be noted that, if the RBE of the chosen radiation were lower, as with photons, a greater amount of radiation, as measured in rads, will have to be delivered to the same target region in order to terminate the cancerous cells. For example, photon radiation has a RBE of 1, thereby requiring 2500 rads to have the same cell terminating effect as antiprotons, which, when equated to heavy ions, has a RBE of 5.

To determine the amount of energy $10^9$ antiprotons should have in order to reach 10 cm below a surface, one can use a TRIM calculation, as found in Zeigler J. F., Biersack J. P., and Littmark U., "Stopping and Range of Ions in Solids,", Vol. 1, 1985 (Pergamon Press, NY). Applying a TRIM calculation demonstrates that an antiproton beam energy of approximately $10^8$ MeV will achieve an end-of-range position that is 10 cm below the surface in a patient. Given that, like protons, antiprotons are low linear energy transfer particles and that only a small portion of antiprotons annihilate prior to reaching the target region, approximately 30 MeV of the $10^8$ MeV is deposited in the target region, while 78 MeV is deposited in collateral tissue. Assuming the volume of collateral tissue between the skin and target area is 9 cc (1 cm×1 cm×9 cm), the damage inflicted by traveling antiprotons can be defined by a RBE of 1.2 (20% greater than protons), and damage is uniformly spread across the collateral tissue, the collateral damage is equal to approximately 168 rads (($1.2 \times 78$ MeV/antiproton$\times 10^9$ antiprotons)/9 cc), which is tolerable and therefore does not require a multiple pathway dosage profile (although it may be done if desired). Therefore, combined the protocol produces a recommended treatment plan: one exposure of 109 antiprotons having an energy of 108 MeV.

In dealing with tumors having a volume greater than 1 cc, multiple doses, spread across a region, can be preferred to minimize collateral tissue damage in any single location. For example, some lung and prostate cancers are intermediate sized tumors and can range, on average, around 150 cc and 35 cc with average surface depths of 12 and 6 cm, respectively. Head and neck tumors may be irregularly shaped and in some embodiments, multiple doses may be utilized to cover the target region.

In either case, the high degree of localization provided by antiproton radiation therapy can allow for one or more of the following: (1) the termination of cancer cells with minimal fractionation requirements; (2) producing tumor cell injury by causing numerous double strand DNA breaks and by inducing cell membrane injury of trans-membranal surface proteins, i.e. by interfering with EGFR (epidermal growth factor receptor) and VEGF (vascular endothelial growth factor receptor) transduction signaling; (3) sparing injury to tumor-adjacent antigen serving macrophage dendritic cells, which facilitate tumor lysis by T-cells in the tumor microenvironment; (4) avoiding injury in the tumor microenvironment to lymphokine activated killer (LAK) T-cells, which become effector cells causing tumor lysis when served with tumor antigens by dendritic cells, an important immunologic activity in facilitating the body's natural defenses against tumor growth; (5) permitting the progeny of tumor sensitized effector LAK T-cells to provide cell lysis of distant microscopic tumor metastatic implants; and (6) causing less hematopoietic injury, which is common in photon regimens, since the bone marrow will be spared the effects of radiation exit dose and dose fall off. This is of particular importance with the increasing use of simultaneous chemotherapy-photon radiation therapy protocols in a variety of cancers, which often lead to blood count depressions that necessitate interruption of treatment. The highly conformal nature of antiproton radiation will avoid this adverse result.

Figure 13:
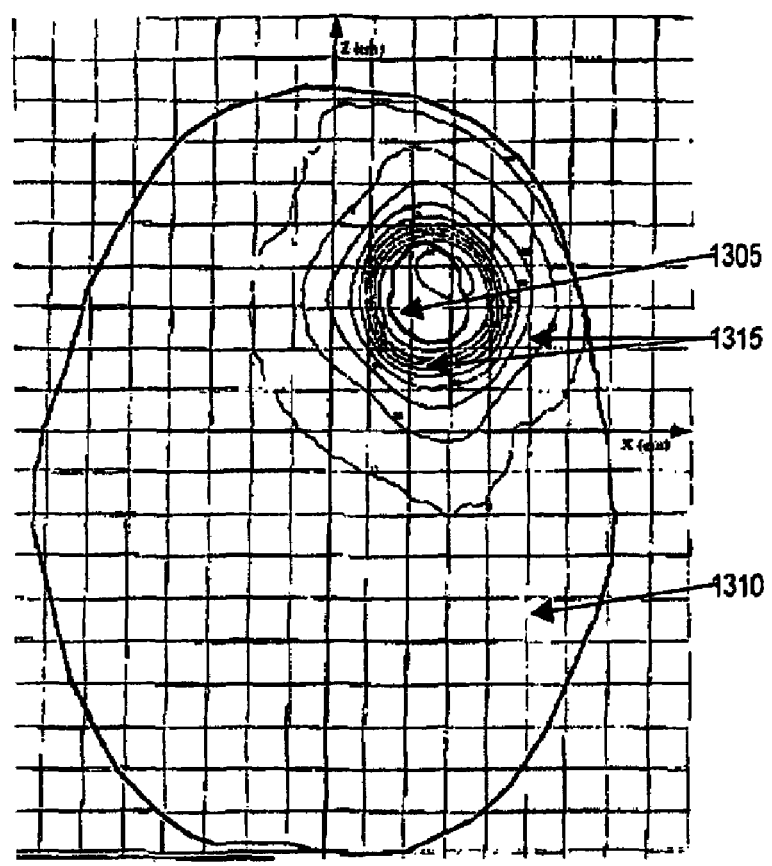
FIG. 13 is a graph illustrating the combination of antiproton dosage ranges with tumor location as imaged by the treatment protocol station of FIG. 12.

In one example embodiment, the treatment protocol station will have a computer-implemented software program capable of taking the requisite input data, namely tumor size and location, and, as shown in FIG. 13, outputting impact graphs superimposed on the scanned images of the patient's tumor, as generated from conventional therapies. A tumor body 1305 is identified and located relative to a patient's anatomy. The tumor body 1305 is positioned in an area within the patient's brain 1310. A plurality of delineated antiproton dosage regions 1315 are defined relative to the tumor body 1305. The dose regions 1315 can be defined in numerous ways, including by percent dosage relative to calculated dose requirements or by absolute dosage amounts, with higher dose regions generally being centered within the plurality of dose regions 1315 and lower dose regions extending to the periphery.

It should be noted that, because of the ability to precisely deliver high amounts of energy into an area without high accompanying collateral damage, a medical practitioner does not need to cover an entire mass with antiproton radiation, but rather, can selectively target highly sensitive areas within a tumor volume to achieve tumor mass destruction with minimal radiation. For example, because tumors rely on fragile blood vessel networks to fuel their rapid growth, it may be possible to kill an entire tumor mass through the directed application of antiproton radiation on areas responsible for providing primary blood supply. By irradiating critical blood vessels one can induce angiolysis, thereby shutting down essential blood supply to a tumor. Similarly, tumors may be killed using antiproton radiation by causing blood vessel swelling such as in AVM's (arteriovenous malformations) which will result in the eventual cut off of a tumor's blood supply. Tumors may also be killed by biologically isolating them through the application of antiproton radiation circumferentially and sparing normal structures interior to the tumor, such as the urethra coursing through a malignant prostate gland. Circumferential antiproton radiation may also induce fibrosis around a tumor mass isolating the tumor and causing it to necrose.

It should further be noted that a substantial number of repeated treatments is not required. Treatment fractionation is required in conventional therapies because of the inability to drive high enough radiation levels to target tissue without causing high collateral damage. Lower target radiation levels, though sufficient to kill dividing cells, are not sufficient to kill resting cells. As a result, multiple treatments have to be applied in order to kill the target cancer cells, and because of the rapid dividing nature of cancer cells, they are more impacted than the collateral cells which have time to repair after radiation exposure. The systems and methods disclosed herein enable the delivery of high radiation levels in target tissue, thereby killing both resting and dividing cancer cells, without causing unacceptable levels of damage to healthy tissue.

Optionally, a patient may also be imaged using a PET scan after the antiproton radiation exposure is completed. Typically, to perform PET scanning, a patient is administered a glucose-tagged radioactive substance that decays inside the body and, in the process, releases positrons which, when detected, can be used to generate an image. Conventional PET scans are limited by the need to have the patient, PET imaging station, and radioactive isotope source (the radiopharmaceutical of appropriate activity) all proximate to each other.

Specifically, PET applications rely on the use of biologically active radiopharmaceuticals where radioactive isotopes in the radiopharmaceutical emit positrons. These isotopes are typically generated through the use of synchrotrons, such as the RDS cyclotron, manufactured by Siemens, which is a frequently used PET device. It incorporates a computer terminal to control the flow of production, and a biosynthesizer unit to carry out the chemical synthesis of radiopharmaceuticals. Using the synchrotron, a stream of charged particles, such as protons or deuterons, bombard a collection of stable, sometimes enriched, isotopes and interact with a subset of those isotopes. Three nuclear reactions are commonly used for the production of C-11 and F-18, the most common PET isotopes. These reactions are: $^{14}N(p,\alpha)^{11}C$, in which the interaction of $^{14}N$ with a proton is then followed by the emission of an alpha particle, resulting in $^{11}C$, $^{18}O(p,n)^{18}F$, in which the interaction of $^{18}O$ with a proton is then followed by the emission of a neutron, resulting in $^{18}F$, and $^{20}Ne(d, \alpha)^{18}F$, in which the interaction of $^{20}Ne$ with a deuteron is then followed by the emission of an alpha particle, resulting in $^{18}F$. Radiopharmaceuticals, made from these radioactive isotopes, are then introduced into a patient's body where the decay of the isotope is monitored.

While many radioactive isotopes can be produced in the cyclotron, the isotopes produced are preferably amenable to human PET use and, therefore; (1) are capable of emitting positrons when they undergo radioactive decay and transform from an unstable isotope into a stable one. (2) Because such isotopes tend to emit positrons relatively quickly, the isotope half-life is preferably long enough to allow for a patient to be administered the substance and placed in a position to be scanned. Furthermore, it can be preferred that the isotopes are readily incorporated into a useful radio-pharmaceutical by chemical synthesis. The most commonly generated isotopes include carbon-11 (half-life 20 minutes), nitrogen-13 (half-life 10 minutes), oxygen-15 (half-life 2 minutes), and fluorine-18 (half-life 110 minutes). Because of these short half-lives, some PET installations have cyclotrons proximate to the PET machine. For example, at the University of Iowa, a compact medical cyclotron is used to generate high energy protons or deuterons by forcing the particles to traverse the cyclotron several hundred times and, during each orbit, receive about 90 keV of energy. When the energies are high enough, the particles are removed through electrostatic deflection and are made to impinge upon small volume hollow metallic cylinders filled with a non-radioactive gas or liquid, causing nuclear reactions to take place within the cylinder and generating the appropriate isotopes.

For certain applications, some of the systems and methods disclosed herein complement the use of PET-specific cyclotron and biosynthesizing stations to perform a PET scan. Conventional PET systems are used to measure and study biological functions, such as glucose uptake. In one embodiment, PET administration is used in combination with certain systems and methods disclosed herein to conduct PET scans. A patient is administered a PET-isotope labeled glucose molecule in order to identify enhanced glucose uptake areas in the body. The detector array incorporated into the antiproton delivery device can be used to monitor resulting decay, thereby repurposing detectors used for antiproton annihilation tracking and measurement for PET scanning. When treating with antiprotons, a medical practitioner can then directly compare PET scanning results with antiproton treatment results. One of ordinary skill in the art will appreciate that, in addition to the aforementioned characteristics, the antiproton delivery detector system for this embodiment should be sufficiently sensitive to differentiate between the decay generated by increased uptake areas of the radiopharmaceutical and the decay generated by the general uptake of the radiopharmaceutical throughout the body.

Additionally, in one example embodiment the in-situ generation of PET isotopes is enabled. The exposure of human tissue to antiproton radiation generates a plurality of unstable isotopes, including, for example, oxygen-15, that are radioactive and emit a positron as a decay product. More specifically, when introduced into a target region, antiproton interactions generate oxygen-15, nitrogen-13, and carbon-11 as by-products. After the appropriate period of time (depending on the half life of the isotope), the generated isotopes decay, emitting positrons. The positrons travel a short distance in the target area before striking an electron. When this collision occurs, two gamma rays are simultaneously produced and travel away from each other at 180 degrees, toward the detector assembly already present for tracking gamma radiation generated from neutral pion decay. Each time two detectors detect a gamma ray simultaneously, the annihilation is recorded and the vertex, or point of gamma production, is determined. One of ordinary skill in the art will appreciate that, by reconstructing the location of the plurality of vertices, one can determine where the highest concentrations of isotope generation occurred, where the highest concentrations of tissue existed, and, by extrapolation, where cancerous tissue was located, assuming correlations between isotope generation, tissue density and cancerous tissue.

Further, because those radioactive by-products are generated through antiproton annihilations in the region of interest, they better image only the region of interest. A difference between conventional PET imaging and the PET imaging aspect of the embodiments disclosed herein is that the conventional PET image reveals regions of enhanced glucose uptake, whereas the image in embodiment disclosed herein reveals a region where antiproton annihilations have occurred. Conventional PET scanning is dependent upon the uptake, by tissue, of radioactively tagged glucose, which may or may not be confined to a particular region of interest. As a result, a substantial amount of gamma radiation is emitted by positron-electron annihilations that are outside the region of interest and the result of the uptake of tagged glucose by healthy tissue elsewhere in the patient. These various emissions represent noise in the form of an undesired background signal relative to the gamma emissions from the areas of interest. In one example embodiment, the signal to noise ratio is greatly enhanced by the elimination of extraneous radiation emissions from areas outside the target region. It should be noted, however, that the intrinsic resolution of the conventional PET image and the resolution of the PET image produced by the embodiments disclosed herein are similar and that both images are degraded in absolute resolution due to diffusion and migration of the PET isotopes in tissue before the radioactive decay occurs that emits the positrons.

Another advantage of the PET imaging aspect of embodiments disclosed herein is that standard PET cameras can be used to collect the image and the same detectors used for conventional PET imaging can be used to detect antiproton-generated PET. As the radioactive decay of the PET isotope does not occur promptly with respect to the antiproton annihilations, computer modeling of the diffusion and migration of the PET isotopes in tissue should be done in order to reconstruct where the annihilation took place. A higher resolution image, relative to PET images, is obtainable by imaging the higher-energy gamma ray emissions that are associated with the decay of the neutral pions that are created in the antiproton annihilation event, as the neutral pions decay nearly instantaneously after the neutral pion is created. It should be noted that, as previously discussed, the detection of the gamma rays from neutral pion decays generally uses a different type of detector than the gamma ray detectors used in a standard PET camera.

In another aspect, the use of the low background noise characteristic of antiproton-produced radioisotopes, coupled with the short half lives of the radioisotopes, to image flow and/or diffusion characteristics within vessels or through tissue is enabled. Antiproton annihilations in blood or other fluids create short-lived radioisotopes within the blood or fluids. The most common radioisotopes that are produced in human fluids are $^{11}C$, $^{13}N$, and $^{15}O$, which have half lives of 20, 10, and 2 minutes, respectively. Circulatory blockages or hemorrhages can be imaged using standard PET imaging equipment to follow the diffusion of small volumes of blood or fluid that is initially irradiated with a low-intensity, highly localized pulse of antiprotons. A low-intensity pulse of antiprotons creates a small volume of radioisotopes that will flow with the blood or fluid in the local region. The path of the flow is readily imaged from the emitted radiation because the background intensity is negligible, as described above, and the resulting signal-to-noise is high. The short half lives of the radioisotope species result in large signals relative to background levels for ease of detection and short total lifetimes for low residual effects.

4. A Bi-Polar Accelerator System

Referring back at FIG. 7, delivery pipe 1005 is configured to deliver an anti-proton beam to the anti-proton radiating and imaging device illustrated in FIG. 7. Often, as described above, a periodic accelerator is used to accelerate the anti-proton beam for delivery to the anti-proton radiating and imaging device via delivery pipe 1005. For example, a periodic accelerator such as a cyclotron, synchrotron, synchrocyclotron, or a Fixed-Field Alternating Gradient (FFAG), accelerator can be used to accelerate an anti-proton beam for delivery to the radiating and imaging device illustrated in FIG. 7. Linear accelerators such as Linacs, Radio Frequency Quadrupoles (RFQs) and pulse-forming systems using Blumlein Technology to repetitively form an electrostatic accelerating potential, e.g., a dielectric wall accelerator, can also be used for the same purpose.

The same type of accelerators can also be used to accelerate protons for delivery to a proton radiating and imaging device. Existing accelerator systems, however, are designed to accelerate positively charged ions in one direction in the accelerator system and negatively charged ions in the opposite direction to the accelerator system. In other words, conventional accelerators are not capable of accelerating both negative and positive ions in the same direction. For example, accelerator systems have been built and used to create, cool, and store anti-particles, such as anti-protons. Such systems are included in large physics facilities in Europe (CERN), Japan (KEK), and the United States (FermiLab). Each of these facilities has an accelerator and a collection and cooling system, and some of these accelerators include both positive and negatively charged ions, and/or electrons, in the same accelerator. But the oppositely charged particles travel in opposite directions through the accelerator systems.

In certain instances, it can be beneficial for a single system to be able to deliver either a negatively charged, or positively charged beam. Using conventional technology, however, this would require the inclusion of two different accelerators and beam delivery units, one to accelerate positively charged ions in one direction and one to accelerate negatively charged ions in the other direction. Since these devices and the facilities designed to house them are quite large, it is impractical to have two separate systems to deliver both positively and negatively charged ion beams in the same direction.

In the embodiments described below, however, a single accelerator can be used to accelerate either positively or negatively charged ions in the same direction. For example, in certain embodiments, a system as described herein can deliver either positively charged or negatively charged ions for treatment of a patient as described above. In order to provide a beam of either positively or negatively charged ions using a single accelerator, a configurable power source for supplying a current to bending magnets in the accelerator is included in the system. The power source must be configurable so that the direction of the current supplied can be changed in order to change the polarity of the bending magnets. This allows a single accelerator to accelerate positive and negatively charged ions in the same direction.

Further, a controllable injection port for injecting either negative or positively charged ions into the accelerator should also be included in the system. For example, the injection port can be controlled via magnets so as to select either positively or negatively charged ions for injection into the accelerator. As mentioned above, the accelerator can either be a cyclotron, synchrotron, synchrocyclotron, or a FFAG. In other embodiments, the accelerator can be a linear accelerator such as a Linac, or a RFQs, or a pulsed-forming system using Blumlein Technology.

Figure 14:
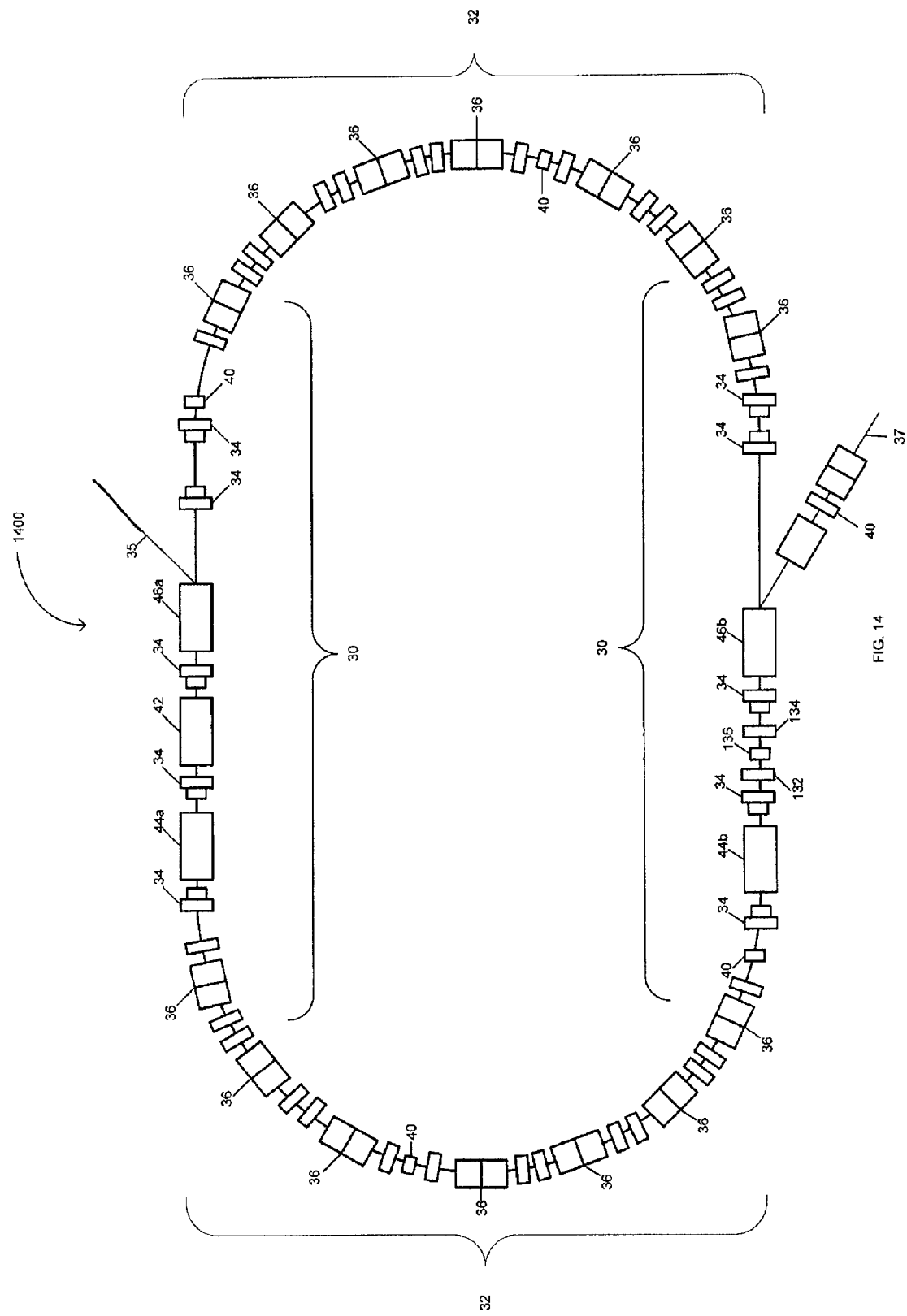
FIG. 14 is a diagram illustrating an example bi-polar accelerator configured in accordance with one embodiment.

FIG. 14 is a diagram illustrating a synchrotron 1400 for use in a bipolar accelerator system that can provide either positively charged or negatively charged ions in the same direction. It will be understood, however, that the synchrotron depicted, and described in relation to FIG. 14 is by way of example only and should not be seen as limiting the systems and methods described herein to any particular type of synchrotron or to any particular type of accelerator. In fact, it will be understood that the systems and methods described herein can be extended to other types of accelerators, such as cyclotrons, synchrocyclotrons, and FFAG's.

Synchrotron 1400 generally consists of two straight sections 30 and two 180 degree arc sections 32. Each straight section 30 can include five half-cells 34, without bending magnets, and each arc section 32 can include seven half-cells 36 with combined function magnets (FODO magnets). The straight sections 30 accommodate the functions of injection, extraction, and acceleration. The primary physical and optical parameters for the synchrotron are listed in Table 1.

TABLE 1

| | |
|---|---|
| Circumference, C [m] | 30.65 |
| Number of FODO cells in the arcs | 7 |
| Half-cell length in the arc [m] | 1.1 |
| Maximum distance between quadrupoles [m] | 1.8 |
| Bend magnetic length [m] | 0.760 |
| Quadrupole magnetic length [m] | 0.14 |
| Injection pulse length, $\Delta t$ [ns] | 25-100 |
| Injection pulse current [mA] | 0.06-2.72 |
| Normalized rms emittance, e [μm] | 0.15 |
| Momentum width at injection (rms), $\sigma p/p$ | 0.001 |
| Total momentum width at injection, $\Delta p/p$ | +/−0.0023 |

TABLE 1-continued

| | |
|---|---|
| Total kinetic energy width at injection, ΔK [keV] | +/−32 |
| Horizontal tune, Qx | 3.38 |
| Vertical tune, Qy | 3.36 |
| Average phase advance per cell, Horizontal (Arcs) [deg] | 108 |
| Average phase advance per cell, Vertical (Arcs) [deg] | 92.16 |
| Max. horizontal beta function, βxmax [m] | 5.79 |
| Max. vertical beta function, βymax [m] | 6.23 |
| Max. dispersion function, ηmax [m] | 2.01 |
| Natural horizontal chromaticity, ξx | −1.48 |
| Natural vertical chromaticity, ξy | −4.14 |
| Transition gamma, T | 2.72 |

The half-cell magnets 34 used in the straight sections can be short quadrupole magnets for beam focusing. The combined function main magnets 36 can be the sole optical component of the arcs. As will be discussed in further detail below, the combined function magnets both bend the beam and focus/defocus the beam. In particular, the combined function magnets 36 can be bent in a chevron shape, with respect to a magnet center of curvature, for bending the proton beam. These magnets can be further designed in either a focusing (F) or defocusing (D) style that differ only slightly in the 2-D cross section of the magnet laminations. The optical lattice can also include a modest number of dipole correctors 38 and Beam Position Monitors (BPMs) 40. Each BPM is integrated into a vacuum pipe near the RCMS quadrupoles 34. In certain embodiments, only one type of each of these magnets (and diagnostics) is used, simplifying the design and reducing the required number of spares. In certain embodiments, one half-cell in one of the straight sections 30 is occupied by a radio frequency cavity 42. Moreover, each straight section 30 further includes a fast kicker 44a and 44b and a septum magnet 46a and 46b separated by one half-cell.

Variation of the extraction energy can be achieved by adjusting a trigger based on the RF frequency to control the extraction time. This avoids the necessity for energy degraders, delivering a high quality beam with good energy resolution and few losses. Although the excitation of the transport line magnets needs to change in proportion to the extraction momentum, the transport lines are designed to be insensitive to momentum matching errors and magnet settling effects, since they are achromatic and (mostly) dispersionless.

The dispersion at the entrance and exit points of the arcs 32 is zero, so the straight sections 30 are dispersion free. The dispersion matching in the arcs 32 can be performed by choosing suitable values for the quadrupole components of the two different kinds of combined function magnet 36. The quadrupole components of the combined function magnet 36 can also been chosen to make the beam size as small as possible. Since the half cells 34 in the straight sections 30 are longer than those in the arcs 32, it can be necessary to match the beta functions between the arcs and the straight sections.

Table 3 lists the expected beams sizes and other parameters at 3 times corresponding to injection, minimum extraction energy, and maximum extraction energy, using the beam parameters from Table 2.

TABLE 2

| | Injection | minimum | maximum |
|---|---|---|---|
| Kinetic energy, K [MeV] | 7.0 | 60.0 | 250.0 |
| Momentum, p [MeV/c] | 114.8 | 340.87 | 729.1 |
| Lorentz | 1.0075 | 1.0639 | 1.2664 |

TABLE 2-continued

| | Injection | minimum | maximum |
|---|---|---|---|
| Lorentz | 0.122 | 0.3415 | 0.614 |
| Revolution frequency, Frev [MHz] | 1.188 | 3.340 | 6.002 |
| Revolution period, Trev [μs] | 0.842 | 0.300 | 0.166 |
| Rigidity, Bρ [Tm] | 0.383 | 1.137 | 2.432 |
| Dipole field, B [T] | 0.226 | 0.671 | 1.436 |
| Normalized rms emittance [μm] | 0.15 | 0.15 | 0.15 |
| Unnormalized RMS emittance εu [μm] | 1.22 | 0.413 | 0.193 |
| Max vertical rms beam size [mm] | 2.76 | 1.60 | 1.10 |
| Max horizontal rms beam size [mm] | 2.66 | 1.55 | 1.06 |
| Max dispersive (horz) size, HWFM [mm] | 6.50 | 2.67 | 0.97 |

A single resonant power supply can be configured to drive all of the synchrotron bending magnets in series, combining a sinusoidal alternating current of amplitude $I_{AC}$ with a constant direct current $I_{DC}$, so that the total bending magnet current is:

$$I(t)=I_{DC}-I_{AC}\cos(2\pi f_{rep}t)$$

Injection occurs at t=0 when the current $I=I_{DC}-I_{AC}$ is at its minimum. Extraction can occur at any time between t=7 ms and t=16.7 ms, when the kinetic energy K is in the range 20 to 300 MeV, for example in the range 60 to 250 MeV. The magnetic field B in the bending magnets, and the beam momentum P are both proportional to the main magnet current (except for small saturation effects).

The energy for the beam acceleration is supplied by a single Radio Frequency (RF) cavity 42, with a voltage that varies sinusoidally during the acceleration half of the magnetic cycle. The RF system and beam performance in longitudinal phase space are discussed at greater length below Beam injector module 35 can be a conventional tandem Van de Graaf injector. While the incoming beam from injector 35 into the synchrotron 1400 is always in the same horizontal plane as the circulating beam, the horizontal angle and displacement between the two must be reduced to zero. This is the function of the electrostatic injection inflector 46a and the injection kicker 44a, shown in FIG. 14. The electrostatic injection inflector 46a generates a constant electrostatic field and, at the end of the inflector both beams are in the same beam pipe for the first time. The injection kicker 44a, which is a pulsed magnet, completes the task of injection. Example key parameters of the electrostatic inflector 46a and the injection kicker 44a are summarized in Table 3.

TABLE 3

| | |
|---|---|
| Electrostatic inflector | |
| Bend angle, Φ | 6.5° |
| Radius of curvature, ρ [m] | 11.5 |
| Active length, D + d [m] | 1.4 |
| Septum thickness [mm] | 1 |
| Gap, g| [mm] | 18 |
| Voltage, V [kV] | 22 |
| Electric field [kV/cm] | 12 |
| Injection Kicker | |
| Kick angle, ΦK [mrad] | 5.3 |
| Magnetic length [m] | 0.2 |
| Magnetic field, B [G] | 100 |
| Gap, $g_K$ [mm] | 30 |
| Current, NI [A] | 240 |
| Rise time [ms] | <16 |
| Flat top [ns] | >100 |
| Fall time [ns] | <600 |
| (Revolution, Period [ns] | 840) |

Turning to the extraction side of the synchrotron 1400, the fast kicker magnet on this side is termed an extraction kicker 44b and the septum magnet is termed an extraction septum 46b. The injection and extraction interfaces of the synchrotron 1400 are similar in many ways. The extraction kicker 44b begins the extraction process by quickly turning on a vertical magnetic field during a selected turn number, thereby selecting the energy of the extracted beam. The angle is sufficient to move the beam horizontally across a current sheet at the upstream end of the extraction septum magnet 46b, which also bends the beam horizontally. The positions of the extraction kicker 44b and the extraction septum 46b are shown schematically in FIG. 14.

Example parameters of the extraction kicker 44b and the septum magnet 46b are summarized in Table 4.

TABLE 4

| Extraction Kicker | |
|---|---|
| Bend Angle [mrad] | 5.48 |
| Magnetic strength [Gm] | 133 |
| Magnetic length [m] | 0.8 |
| Magnetic field [G] | 167 |
| Gap [mm] | 30 |
| Current [A] | 398 |
| Rise time [ns] | <100 |
| Flat top [ns] | >70 |
| Fall time [ns] | <16 |
| (Revolution Period [ns] | 167) |
| Septum Magnet | |
| Bend angle | 6.5° |
| Radius of curvature [m] | 12.268 |
| Length [m] | 1.481 |
| Magnetic field [G] | 1983 |
| Gap [mm] | 12 |
| Septum (Cu) thickness [mm] | 4 |
| Current [A] | 1893 |
| Half-sine pulse length [μs] | 10 |
| Ripple | <2% |

In order for, e.g., synchrotron 1400 to accelerate both positively charged and negatively charged ions, e.g., protons and anti-protons, in the same direction, the magnetic field for bending magnets 36 must be reversed. It will be understood that for linear accelerators, where the ions are accelerated in a straight line, accelerating both positively charged and negatively charged ions is not such an issue, since the ions are being accelerated by an electromagnetic wave. Accordingly, positive ions will be accelerator in one direction, e.g., in the crest of the wave, while negative ions can be accelerated in the same direction in the trough of the wave.

But if the ions must travel around a bend, e.g. sections 32 of synchrotron 1400, then the magnetic field polarity of, e.g., magnets 36 should be reversed for negative ions versus positive ions. This can be achieved by reversing the current supplied by the main magnet power supply.

Figure 15:
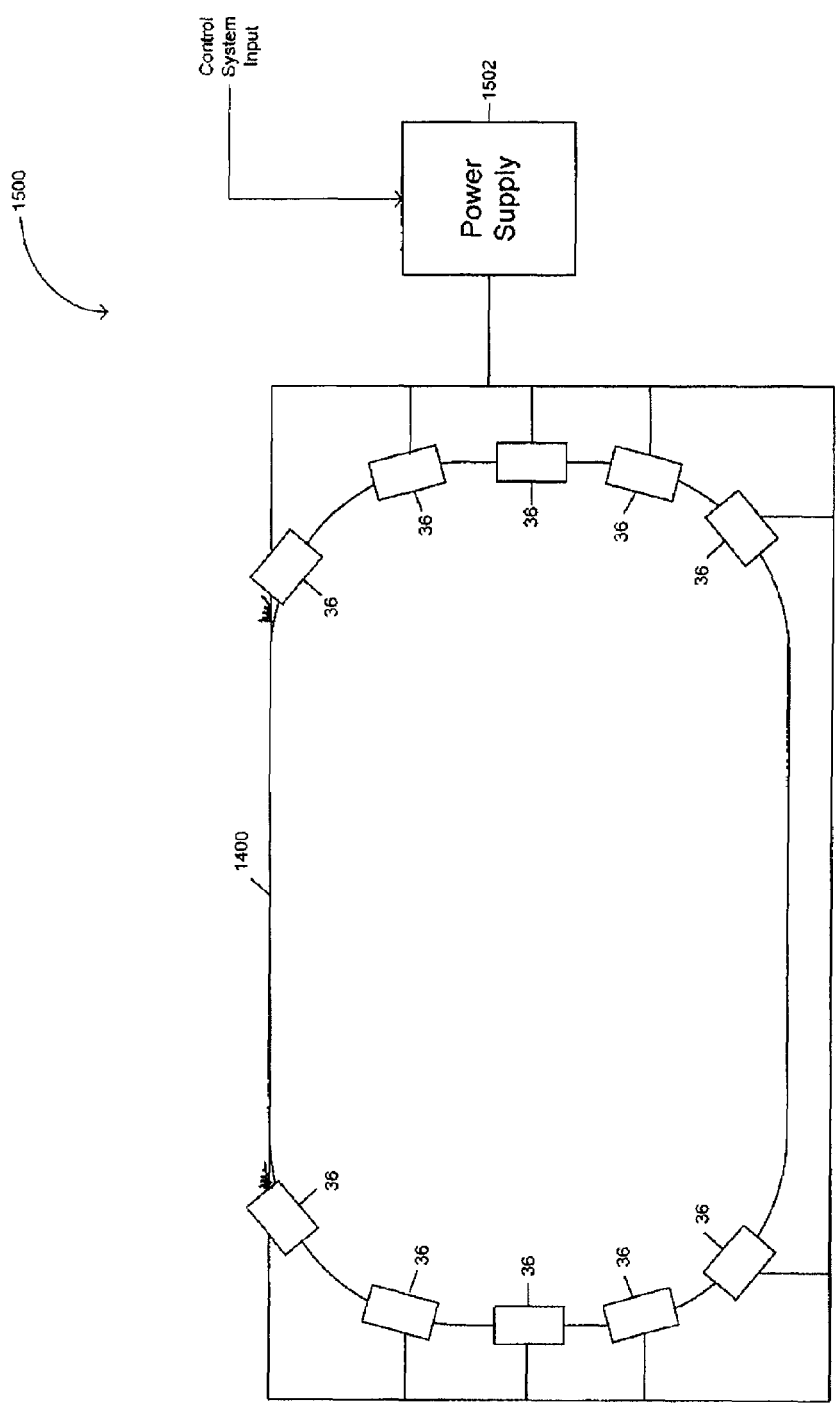
FIG. 15 is a diagram illustrating an example beam delivery system that cab comprise the accelerator of FIG. 14 and includes a configurable power supply in accordance with one embodiment.

FIG. 15 is a diagram illustrating a an example beam delivery system 1500 comprising a synchrotron 1400 and a configurable power supply 1502 in accordance with one embodiment. In system 1500, the current supplied by main magnet power supply 1502 can be reversed, which can cause the polarity of the magnetic field generated by bending magnets 36 to be reversed. Thus, synchrotron 1400 can accelerate both positively charged and negatively charged particles in the same direction.

It should be noted that the magnetic fields generated by bending magnets 36 can, in certain embodiments, also be re-phased for optimum performance. Further, in certain embodiments, the polarity of the magnetic field produced by magnets 34 can also be reversed, and the field re-phased, in unison with that of magnets 36.

Configurable power supply 1502 can be controlled by an input form a control system interfaced with system 1500. For example, a computerized control system, such as the treatment protocol station illustrated in FIG. 12, can be interfaced with system 1500 and configured to cause power supply 1500 to reverse the direction of the current provided as required to accelerate either positive or negative ions. Alternatively, power supply 1502 can be configured for manual configuration.

In embodiments that use both positive and negative ions, the treatment protocol station can be configured to determine the amount of negative ion radiation and/or positive ion radiation needed to terminate the target mass in a similar manner as described above for antiproton treatments.

Thus, the protocol treatment facility can be configured to use equations, this time for positive and/or negative ions as required, to determine the amount of energy deposited in collateral tissue and the residual energy plus annihilation event radiation effects, such as caused by the emission of particles like alpha particles. The energy deposited in the mass, along with the lateral spreads and Bragg Peak contours, can also be determined. Once done, an energy deposition profile can be generated that covers the entire mass with sufficient positive ion and/or negative ion induced radiation by summing multiple Bragg Peaks, assuming a plurality of spot scans performed at varying depths within the tumor region. The amount and energy level of ions, positive and/or negative, for each location to be irradiated, defines the protocol, which can then be sent to the antiproton radiation and imaging device, as previously discussed.

During operation, a beam monitoring system and range shifter can be used to measure the actual dosage of negative ions being delivered to insure it correlates with the desired calculated dosage. To the extent a range shifter is used, negative ion losses, caused by the degradation process, need to be calculated and incorporated into all beam monitoring calculations to insure accurate determination of actual negative ions delivered to the patient. More conventional techniques can be used for real-time imaging and dosage analysis for the positive ions.

Figure 16:
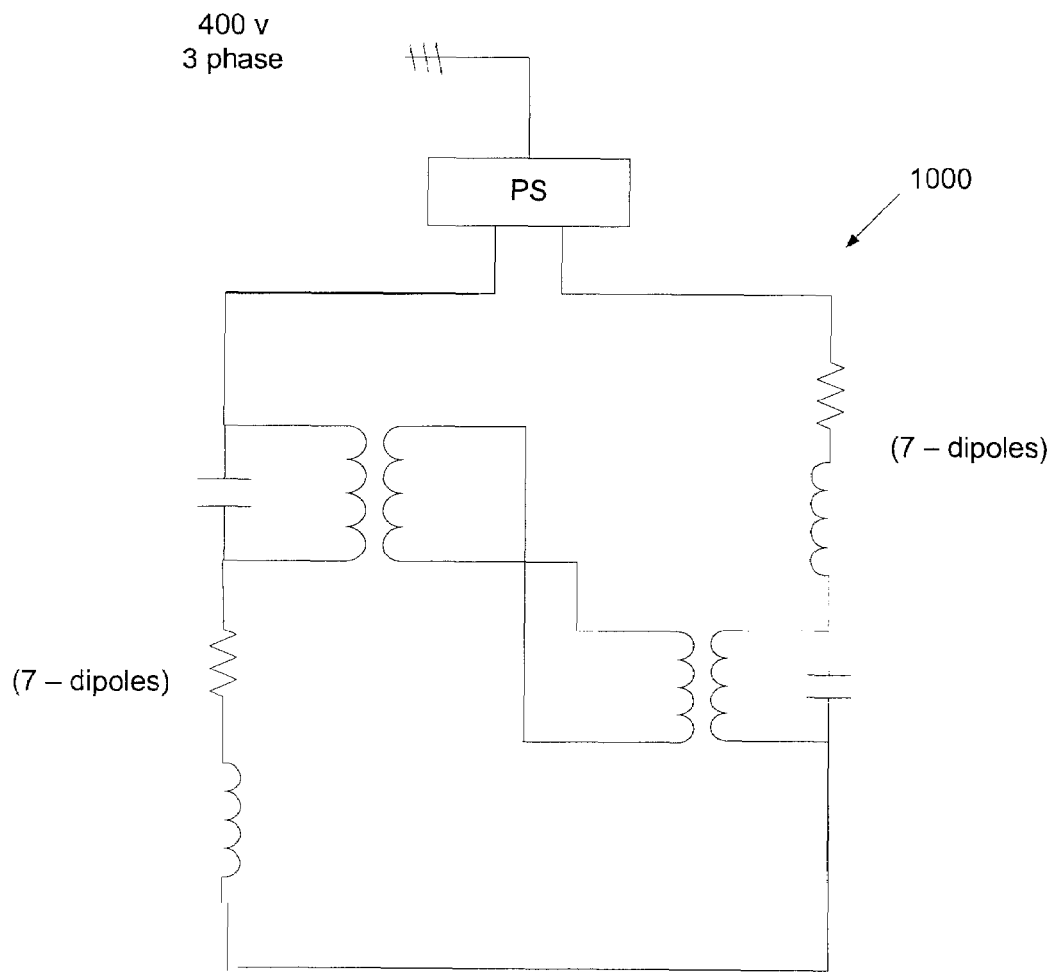
FIG. 16 is diagram illustrating an example configurable power supply for use in the system of FIG. 15 configured in accordance with one embodiment.

An example main magnet power supply system 1600 that can be configured to perform the functions required for controllable power supply 1502 is illustrated in FIG. 16. In this example embodiment, power supply system 1600 comprises a single 30 Hz series resonant power supply that drives, e.g., the 14 combined function magnets 36 in series. Such systems are extremely reliable because of their simplicity. Besides their simplicity, resonant power supplies have the major advantage of continuously exchanging stored energy between the magnets and capacitors, with the power supply providing only the losses. This makes them very economical to operate. It also greatly reduces the power line swing, when compared to a rapid cycling programmable power supply. The large variations in reactive power flow that otherwise occur cause voltage flicker problems, which can be very costly to solve.

The power supply generates a current of the form:

$$I_m(t) = I_{dc} - I_{ac} \cos(2\pi f t),$$

where a direct current bias of $I_{dc}$=1480 Amps is added to the sinusoidal alternating current ($I_{ac}$=1090 Amps) to ensure that the minimum current matches the required field at injection. The beam can be injected into the ring at t=0 when I=390 Amps. The beam can be extracted sometime before t=16.66 ms when $I_m(t)=2570$ Amps. Except for iron saturation effects, the beam momentum is directly proportional to the plain magnet current.

Figure 17:
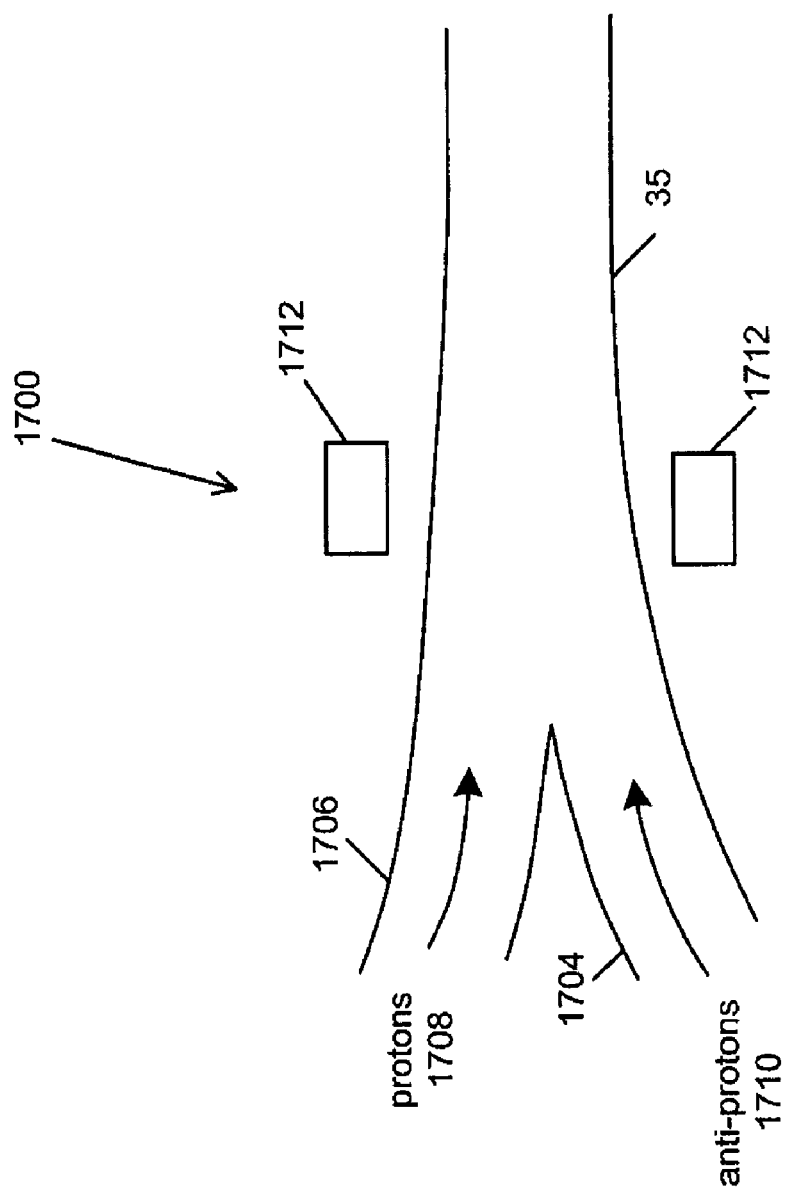
FIG. 17 is a diagram illustrating an example ion injection port that can be used in conjunction with the accelerator of FIG. 14.

Referring to FIG. 17 power supply system 1600 can comprise two capacitor banks with DC bypass chokes are used in series with the magnets of the synchrotron. The resonant circuit can be driven by one programmable excitation power supply. In a series resonant topology, the excitation power supply can deliver the full magnet current, but at a significantly reduced voltage when compared to a non-resonant system. The chokes can be designed with secondary windings, which can be connected to provide coupling between the individual resonant circuits. Table 5 shows example parameters for one embodiment of the main magnet power supply system 1600.

TABLE 5

| | |
|---|---|
| Repetition Rate, $f_{rep}$ [Hz] | 30 |
| Topology | Series Resonant |
| Number of excitation power supplies | 1 |
| Excitation power supply voltage [V] | +/−250 |
| Maximum power supply current [A] | 3000 |
| Nominal peak current | 2700 |
| Injection current [A] | 390 |
| Direct current, $I_{DC}$ [A] | 1480 |
| Alternating current, $I_{AC}$ [A] | 1090 |
| Number of capacitance banks | 2 |
| Number of bypass chokes | 2 |
| Number of main magnets | 14 |
| Capacitance per bank [mF] | 10.58 |
| Inductance of choke [mH] | 5.32 |
| Inductance of main magnet [mH] | 0.76 |
| Resistance of choke [mΩ] | 10 |
| DC resistance per main magnet [mΩ] | 1 |
| Quality factor | 28 |
| Magnet stored energy [kJ] | 39.0 |
| Capacitor stored energy [kJ] | 12.8 |
| Choke stored energy [kJ] | 26.2 |
| Maximum reactive power [MW] | 4.5 |
| Capacitor losses [kW] | 7.4 |
| Choke losses [kW] | 98 |
| Magnet losses (total) [kW] | 53 |
| TOTAL losses [kW] | 163 |

Referring back to FIG. 14, ions can be injected into synchrotron 1400 via injection port 35. FIG. 17 is a diagram illustrating a dual function injection port 1700 configured to inject both positive and negative ions in accordance with one embodiment. Dual function injection port 1700 comprises a positive ion, e.g., proton, pathway 1706 configured to supply positive ions 1708 to injection port 35. Dual function injection port 1700 also comprises a negative ion, e.g., anti-proton, pathway 1704 configured to supply negative ions 1710 to injection port 35.

A magnet, or magnets 1712 can be included and configured to control whether positive or negative ions are supplied to injection port 35. In other words, the polarity of the magnetic filed produced by magnet(s) 1712 can be controlled so as to allow positive ions 1708 to flow from path 1706 to injection port 35, while blocking negative ions 1710, when synchrotron 1400 is configured to accelerate positive ions. Conversely, when synchrotron 1400 is configured to accelerate negative ions, then the polarity of the magnetic field produced by magnet(s) 1712 can be controlled in manner designed to block positive ions 1708, while allowing negative ions 1710 to flow to injection port 35.

In certain embodiments, magnet(s) 1712 can be supplied by the same power supply, e.g., power supply 1502 that is configured to supply power to bending magnets 36. In other embodiments, magnet(s) 1712 can be supplied by a separate, controllable power supply. Such a separate controllable power supply can be controlled either by a control system or manually, depending on the embodiment. Further, the magnetic field produced by magnet(s) 1712 may need to be re-phased when switching between positive and negative ions, depending on the requirements of a particular embodiment.

The positive and negative ions can be supplied from a storage container, such as a magnetic containment bottle. Examples of containers for antiprotons are described in U.S. Pat. No. 5,977,554 entitled "Container for Transporting Antiprotons," filed Nov. 2, 1999, U.S. Pat. No. 6,160,263 entitled "Container for Transporting Antiprotons," filed Dec. 12, 2000, U.S. Pat. No. 6,414,331 entitled "Container for Transporting Antiprotons and Reaction Trap," filed Jul. 22, 2002, and U.S. Pat. No. 6,576,9161 entitled "Container for Transporting Antiprotons and Reaction Trap," filed Jun. 10, 2003, each of which is incorporated herein by reference as if set forth in full. Thus for example, antiprotons can be produced using the system illustrated in FIG. 5. The antiprotons can then be accumulated and stored in a container, such as described in the above patents. As described above, the trapped antiprotons are inserted into, e.g., a linear accelerator or synchrotron, accelerated to appropriate energy levels, and then formed into a beam for use in treatment.

In other embodiments, the antiprotons produced by the system in FIG. 3 can be directly input to injector port 1700. In still other embodiments, ions can be supplied by some other system such, or including a small cyclotron or synchrotron.

Referring back to FIG. 7, the ions can then be supplied via delivery pipe 1005 to a gantry. As explained, the gantry may include magnets 1030 configured to guide the antiproton beam through bends in the gantry and ultimately to nozzle 1035. In certain embodiments that gantry can also be configured to supply both positive and negative ions. Accordingly, the polarity of the magnetic field produced by magnets 1030 can also be reversed as required to accelerate either positive or negative ions. In certain embodiments, magnets 1030 can be supplied by power supply 1502. In other embodiments, magnets 1030 can be supplied by a separate controllable power supply. Such a separate controllable power supply can be controlled either by a control system or manually, depending on the embodiment. Further, the magnetic field produced by magnets 1030 may need to be re-phased when switching between positive and negative ions, depending on the requirements of a particular embodiment.

It will be understood that the gantry or delivery system can comprise other magnets configured to guide the positive or negative ion around bends. It will be further understood that the polarity of the magnetic fields produced by any such magnets may need to be reversed based on whether a positive or negative ion beam is being generated in the system.

In fact, the beam can be delivered to multiple treatment rooms, such as treatment rooms 1103 illustrated in FIG. 11. In which case, bending magnets 1110 may need to be controlled so as to direct positive or negative ions as required.

Figure 18:
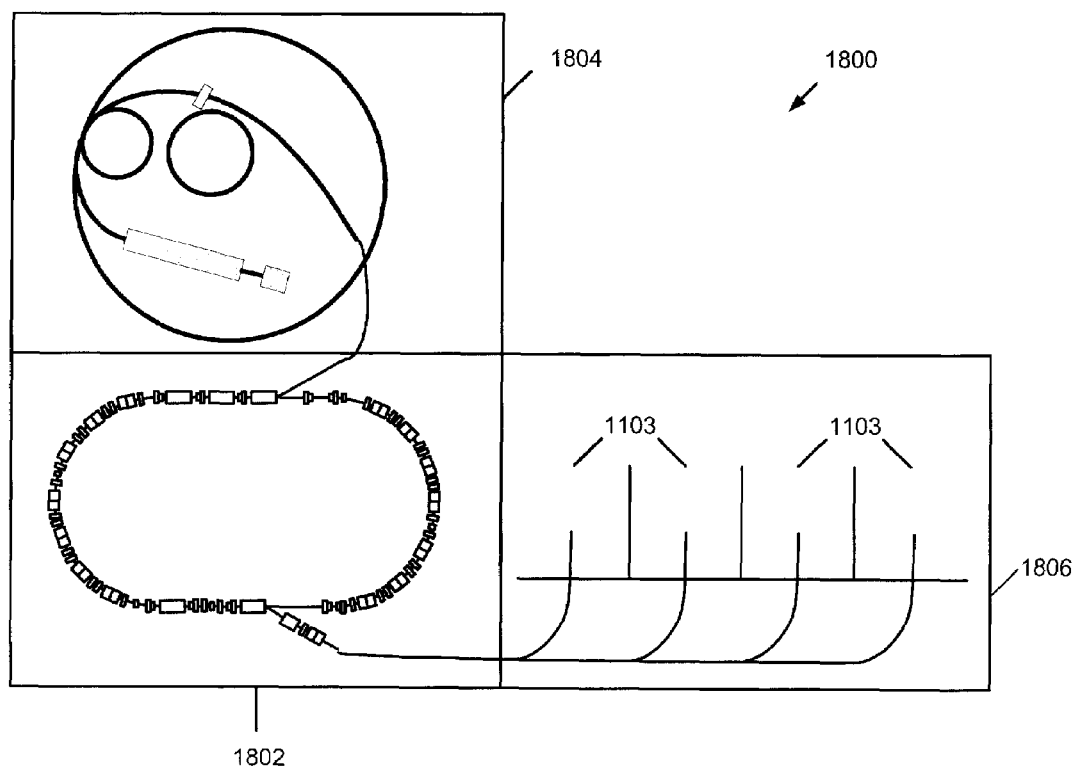
FIG. 18 is a diagram illustrating an example treatment facility that can comprise a bi-polar accelerator such as that illustrated in FIG. 14 in accordance with one embodiment.

FIG. 18 is a diagram illustrating an example treatment facility 1800 that comprises a medical facility 1806 that includes multiple treatment rooms 1103. Treatment rooms 1103 can include gantries or other devices configured to deliver positive or negative ion treatments. Treatment facility 1800 can also comprise an ion beam generation facility 1802, comprising, e.g., a synchrotron 1400, adjacent to medical facility 1806. Synchrotron 1400 can be configured to provide positive or negative ion beams for use in treatment rooms 1103 as required. Treatment facility 1800 can also comprise an ion production facility adjacent to beam generation facility 1802. ion production facility can be configured to produce positive or negative ions, which can then be provided to beam generation facility 1804. As described above, the ions produced in ion production facility 1804 can be directly interfaced, e.g., with synchrotron 1400, or they can be trapped and stored in a container for transport to beam generation facility 1802.

While certain embodiments of the inventions have been described above, it will be understood that the embodiments described are by way of example only. Accordingly, the inventions should not be limited based on the described embodiments. Rather, the scope of the inventions described herein should only be limited in light of the claims that follow when taken in conjunction with the above description and accompanying drawings.

What is claimed is:

1. A bi-polar charged particle beam delivery system, comprising:
    a bi-polar accelerator configured to accelerate positive and negative ions in the same direction, the bi-polar accelerator comprising:
        a plurality of arced sections, and
        a plurality of bending magnets configured to direct the positive and negative ions around the arced section in the same direction; and
    a configurable power supply coupled with the plurality of bending magnets, the configurable power supply configured to supply a reversible current to the bending magnets.

2. The bi-polar beam delivery system of claim 1, wherein the plurality of bending magnets are configured to use the current supplied by the configurable power supply to generate a magnetic field.

3. The bi-polar beam delivery system of claim 2, wherein the configurable power supply comprises a control input configured to receive an input and cause the configurable power supply to reverse the direction of the current supplied to the bending magnets, which in turn causes a polarity associated with the magnetic fields generated by the plurality of bending magnets to be reversed.

4. The bi-polar beam delivery system of claim 1, wherein the bi-polar accelerator is a synchrotron.

5. The bi-polar beam delivery system of claim 1, wherein the bi-polar accelerator is a cyclotron.

6. The bi-polar beam delivery system of claim 1, wherein the bi-polar accelerator is a synchrocyclcotron.

7. The bi-polar beam delivery system of claim 1, wherein the bi-polar accelerator is a Fixed Field Alternating Gradient (FFAG) accelerator.

8. The bi-polar beam delivery system of claim 1, wherein the bi-polar accelerator comprises a dual function injection port configured to supply both positive and negative ions to the bi-polar accelerator.

9. The bi-polar beam delivery system of claim 8, wherein the dual function injector port comprises a positive ion pathway; a negative ion pathway and a magnetic control configured to allow positive ions or negative ions to be injected into the bi-polar accelerator as required.

10. The bi-polar beam delivery system of claim 9, wherein the negative ion pathway is configured to receive negative ions from a negative ion production facility.

11. The bi-polar beam delivery system of claim 9, wherein the positive ion pathway is configured to receive positive ions from a positive ion production facility.

12. The bi-polar beam delivery system of claim 9, wherein the negative ion pathway is configured to receive negative ions from a negative ion containment device.

13. The bi-polar beam delivery system of claim 9, wherein the positive ion channel is configured to receive positive ions from a positive ion containment device.

14. The bi-polar beam delivery system of claim 1, wherein the negative ions are antiprotons.

15. The bi-polar beam delivery system of claim 1, wherein the positive ions are protons.

16. A bi-polar treatment facility, comprising:
    a bi-polar beam delivery system, the bi-polar beam delivery system comprising:
        a bi-polar accelerator configured to accelerate positive and negative ions in the same direction, the bi-polar accelerator comprising:
            a plurality of arced sections, and
            a plurality of bending magnets configured to direct the positive and negative ions around the arced sections in the same direction and form a beam comprising the positive or negative ions, and
        a configurable power supply coupled with the plurality of bending magnets, the configurable power supply configured to supply a reversible current to the bending magnets; and
    a radiating and imaging device, the radiating and imaging device comprising:
        a beam delivery gantry configured to deliver the beam to a target area.

17. The bi-polar treatment facility of claim 16, wherein the gantry comprises a particle beam delivery pipe coupled with the bi-polar accelerator.

18. The bi-polar treatment facility of claim 17, wherein the gantry further comprises a gantry head configured to direct the beam to the target area.

19. The bi-polar treatment facility of claim 17, wherein the gantry head comprises a monitoring system configured to monitor how many positive or negative ions are delivered to the target area.

20. The bi-polar treatment facility of claim 17, wherein the gantry further comprises one or more bending magnets configured to direct the beam around bends in the delivery pipe.

21. The bi-polar treatment facility of claim 20, wherein the plurality of bending magnets in the gantry are configured to produce a magnetic field, and wherein the plurality of bending magnets in the gantry are configured so that the polarity of the magnet field can be reversed as required to direct positive or negative ions around the bends.

22. The bi-polar treatment facility of claim 16, wherein the radiating and imaging device further comprises real-time imaging systems for imaging the application of positive and negative ions to a target mass in the target area.

23. The bi-polar treatment facility of claim 16, wherein the radiating and imaging device further comprises a range shifter configured to control the depth of a dose applied to the target area.

24. The bi-polar treatment facility of claim 16, wherein the radiating and imaging device is configured to scan at least one of the positive and negative ions across a patient's body, to vary a dose as a function of position in a plane perpendicular to the forward motion of the ions as they are being scanned.

25. The bi-polar treatment facility of claim 22, wherein the real-time imaging system comprises a plurality of detectors configured to image the target area during treatment.

26. The bi-polar treatment facility of claim 25, wherein the plurality of detectors are configured to image the treatment area during the application of negative ions by being exposed to annihilation emissions from the treatment area that occur during the delivery of negative ions to the target area.

27. The bi-polar treatment facility of claim 16, further comprising a treatment protocol station configured to determine a treatment protocol defining the application of positive and negative ions to the treatment area.

28. The bi-polar treatment facility of claim 27, wherein the treatment protocol station is configured to control the configurable power supply so as to reverse the current supplied by the configurable power supply as required to accelerate positive or negative ions in the bi-polar accelerator.

29. The bi-polar treatment facility of claim 27, wherein the treatment protocol station is configured to receive real-time information related to the application of positive and negative ions to the treatment area, and wherein the treatment protocol station is configured to use the real-time information to adjust the treatment protocol.

30. The bi-polar treatment facility of claim 29, wherein the real-time information is related to the number of positive ions being delivered to the treatment area during an application.

31. The bi-polar treatment facility of claim 30, wherein the real-time information is related to the number of negative ions being delivered to the treatment area during an application.

32. The bi-polar treatment facility of claim 29, wherein the real-time information is real-time image information of the treatment area.

* * * * *